United States Patent
Chivukula et al.

(10) Patent No.: US 12,083,224 B2
(45) Date of Patent: Sep. 10, 2024

(54) LIPID PARTICLES FOR NUCLEIC ACID DELIVERY

(71) Applicant: Arcturus Therapeutics, Inc., San Diego, CA (US)

(72) Inventors: Padmanabh Chivukula, San Diego, CA (US); Priya Karmali, San Diego, CA (US); Christine Esau, San Diego, CA (US); Jerel Vega, San Diego, CA (US); Yanjie Bao, San Diego, CA (US); Rajesh Mukthavaram, San Deigo, CA (US); Samantha Murphy, Carlsbad, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 960 days.

(21) Appl. No.: 17/042,848

(22) PCT Filed: Apr. 1, 2019

(86) PCT No.: PCT/US2019/025246
§ 371 (c)(1),
(2) Date: Sep. 28, 2020

(87) PCT Pub. No.: WO2019/191780
PCT Pub. Date: Oct. 3, 2019

(65) Prior Publication Data
US 2023/0149310 A1    May 18, 2023

Related U.S. Application Data

(60) Provisional application No. 62/651,020, filed on Mar. 30, 2018.

(51) Int. Cl.
| | | |
|---|---|---|
| *A61K 31/7088* | (2006.01) | |
| *A61K 9/127* | (2006.01) | |
| *A61K 31/7105* | (2006.01) | |
| *A61K 31/711* | (2006.01) | |
| *A61K 39/12* | (2006.01) | |

(52) U.S. Cl.
CPC ........ *A61K 9/1272* (2013.01); *A61K 31/7105* (2013.01); *A61K 31/711* (2013.01); *A61K 39/12* (2013.01)

(58) Field of Classification Search
None
See application file for complete search history.

(56) References Cited

U.S. PATENT DOCUMENTS

| | | |
|---|---|---|
| 8,314,227 B2 | 11/2012 | Wengel |
| 9,051,570 B2 | 6/2015 | Wengel |
| 9,297,009 B2 | 3/2016 | Wengel |
| 9,303,260 B2 | 4/2016 | Wengel |
| 9,340,789 B2 | 5/2016 | Templin |
| 9,365,610 B2 | 6/2016 | Hoge |
| 9,567,296 B2 | 2/2017 | Payne |
| 9,580,711 B2 | 2/2017 | Payne |
| 9,593,077 B2 | 3/2017 | Payne |
| 9,670,152 B2 | 6/2017 | Payne |
| 10,487,105 B2 | 11/2019 | Chivukula |
| 2016/0168567 A1 | 6/2016 | Wengel |
| 2017/0114010 A1 | 4/2017 | Payne |
| 2017/0190661 A1 | 12/2017 | Payne |
| 2020/0368173 A1* | 11/2020 | Hatanaka ................ A61P 35/00 |

FOREIGN PATENT DOCUMENTS

| | | | |
|---|---|---|---|
| WO | WO 2006007712 | * | 1/2006 |
| WO | WO-2016081029 | | 5/2016 |
| WO | WO-2017019523 | | 2/2017 |
| WO | WO-2018119163 | | 6/2018 |

OTHER PUBLICATIONS

Zimmermann, et al., RNAi-mediated gene silencing in non-human primates, Nature, 2006, pp. 111-114, 441(7089).

* cited by examiner

*Primary Examiner* — Maria Marvich
(74) *Attorney, Agent, or Firm* — Mintz Levin Cohn Ferris Glovsky and Popeo, P.C.

(57) ABSTRACT

Nucleic acid immunization is achieved by delivering a nucleic acid (NA), e.g., a mRNA or a DNA, encapsulated within a lipid-NA nanoparticle. The NA encodes an immunogenic compound of interest. The lipid-NA nanoparticle is effective for in vivo delivery of NA to a vertebrate cell, including upon administration to a subject. The lipid-NA nanoparticle are incorporated in pharmaceutical compositions for immunizing subjects against various diseases.

17 Claims, 16 Drawing Sheets

LIPID PARTICLES FOR NUCLEIC ACID DELIVERY

BACKGROUND

Lipids are used as materials for ribonucleic acid (RNA) delivery owing to their ability to form lipid-NA nanoparticles that encapsulate siRNA for delivery to target cells upon parenteral administration. Zimmermann, 2006, Nature, doi:10.1038/nature04688.

The delivery of nucleic acids for immunizing subjects has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines and, in particular, for improved ways of delivering nucleic acid vaccines.

SUMMARY

What is disclosed herein is a pharmaceutical composition, comprising
  a lipid-NA nanoparticle comprising lipids, a nucleic acid, and pharmaceutically acceptable excipients;
  wherein the lipids comprise a cationic lipid, a non-cationic lipid, a PEG-lipid, and a lipid of formula I

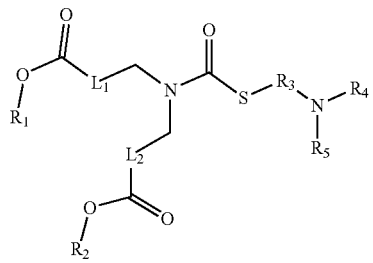

I wherein
  $R_1$ and $R_2$ are the same or different, each independently a linear or branched alkyl or alkenyl consisting of 3 to 31 carbons,
  $R_3$ is a linear or branched alkylene consisting of 1 to 6 carbons,
  $R_4$ and $R_5$ are the same or different, each a hydrogen or a linear or branched alkyl consisting of 1 to 6 carbons;
  $L_1$ and $L_2$ are the same or different, each a linear alkylene of 1 to 20 carbons or a linear alkenylene of 2 to 20 carbons, and wherein the nucleic acid encodes an antibody or an immunogenic peptide.

In preferred embodiments, the cationic lipid of the lipid-NA nanoparticle is a phospholipid; the non-cationic lipid is cholesterol; or the PEG-lipid is a PEG-diacylglycerol (PEG-DAG) or a PEG-dialkyloxyalkyl (PEG-DAA). In other preferred embodiments, $R_3$ consists of ethylene or propylene; $R_4$ and $R_5$ separately are methyl or ethyl; $L_1$ and $L_2$ are each an alkane consisting of 1, 2, 3, 4, 5, 6, 7, 8, 9, or 10 carbons; $R_1$ or $R_2$, or both is an alkenyl; $R_2$ is an alkenyl consisting of 9 carbons; or $R_1$ is a branched alkane.

The lipid of formula I preferably is selected from the group consisting of a compound of formula ATX-43, ATX-57, ATX-58, ATX-61, ATX-63, ATX-64, ATX-81, ATX-82, ATX-83, ATX-84, ATX-86, ATX-87, and ATX-88.

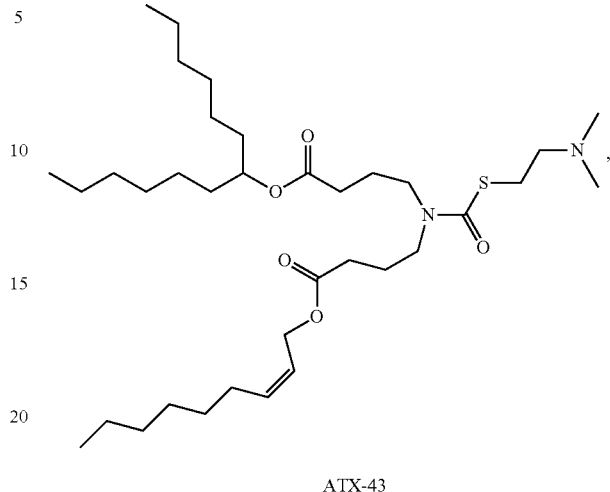

ATX-43

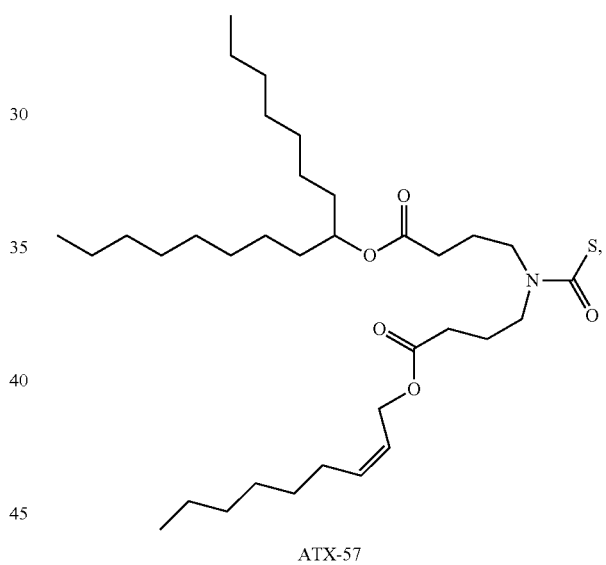

ATX-57

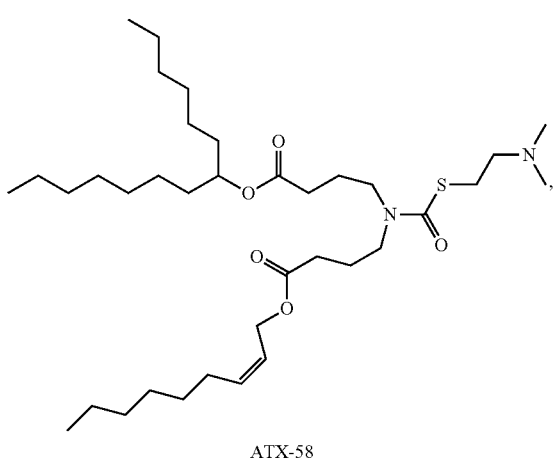

ATX-58

-continued
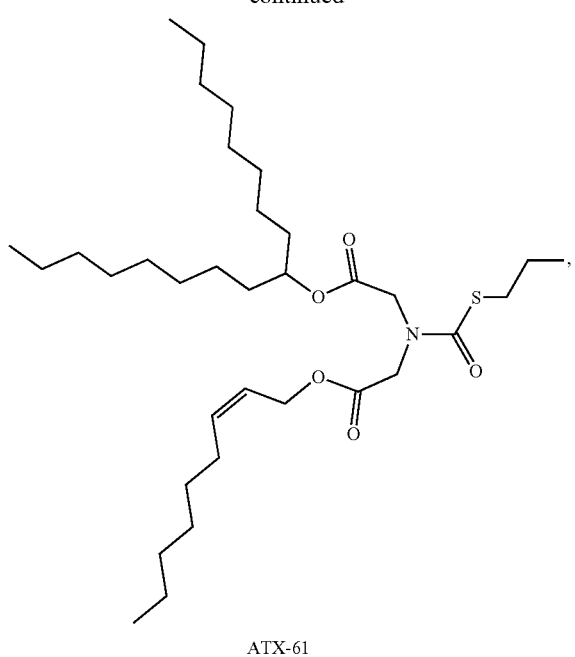
ATX-61
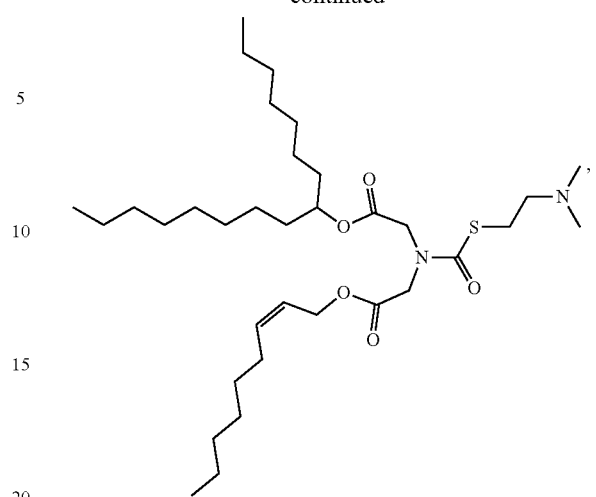
ATX-64
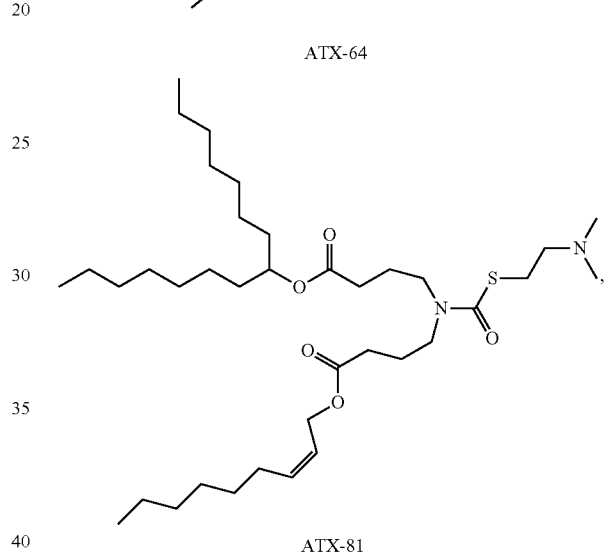
ATX-81
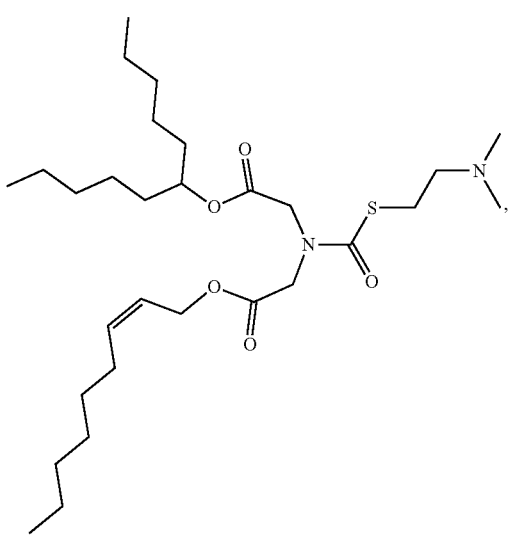
ATX-63
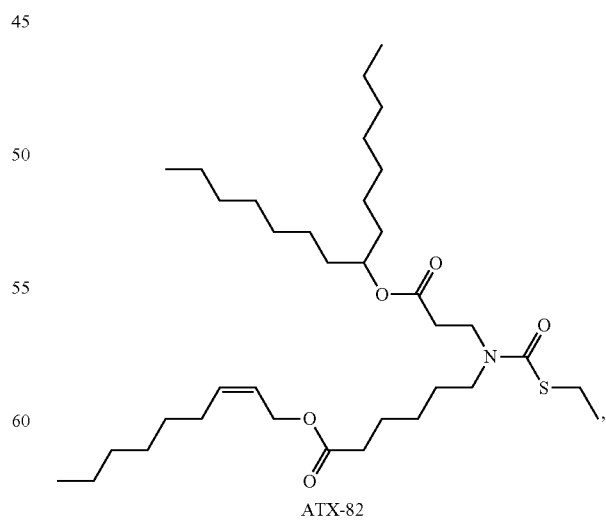
ATX-82

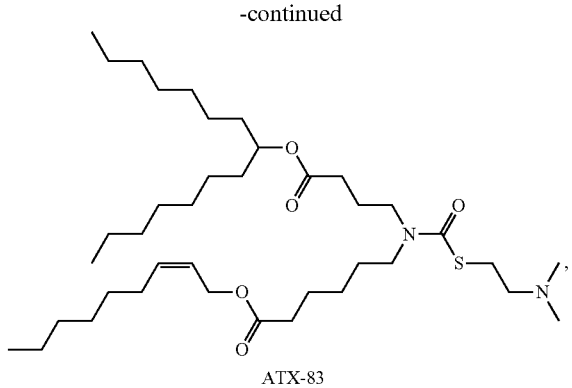
ATX-83
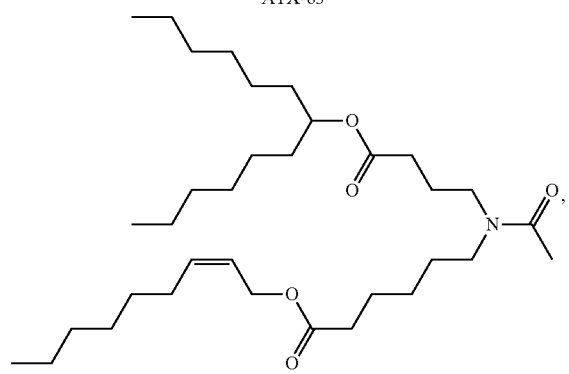
ATX-84
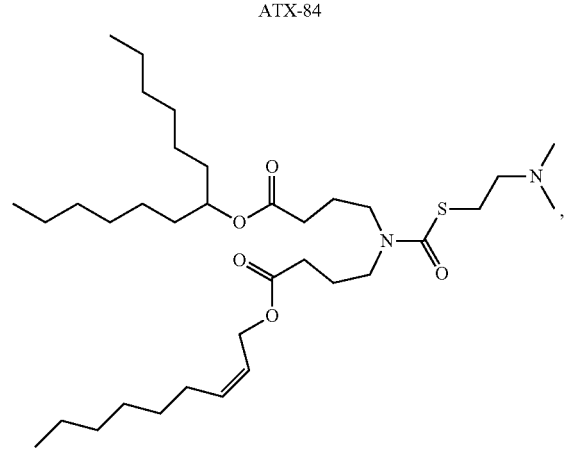
ATX-86
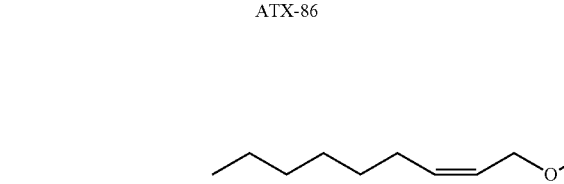
ATX-87
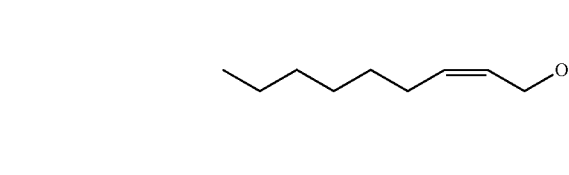
ATX-88
The lipid of formula I is preferably selected from the group consisting of a compound of formula ATX-002, ATX-003, ATX-009, ATX-010, ATX-011, ATX-012, ATX-013, ATX-015, ATX-017, ATX-026, and ATX-029
ATX-002

-continued
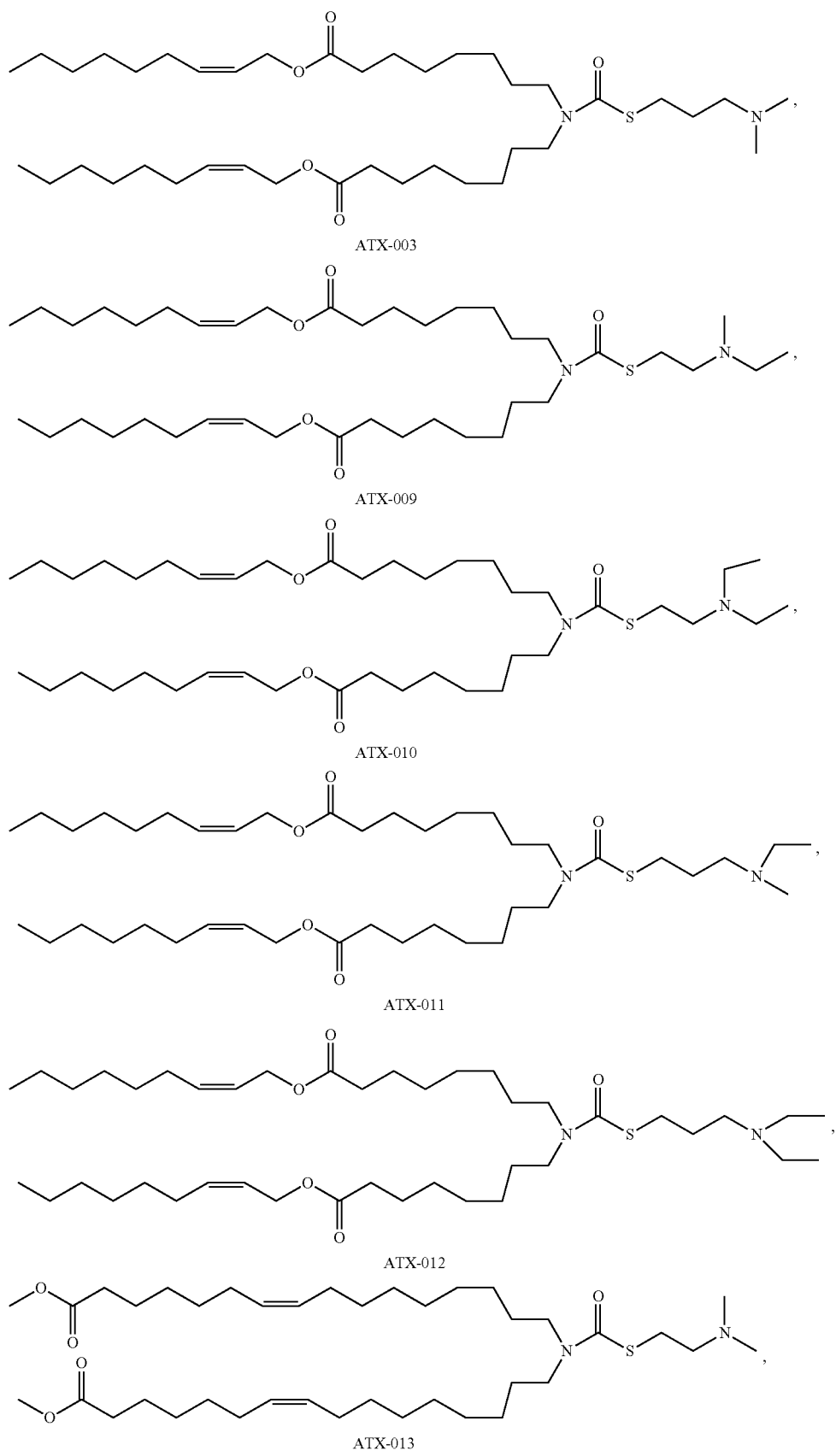
ATX-003
ATX-009
ATX-010
ATX-011
ATX-012
ATX-013

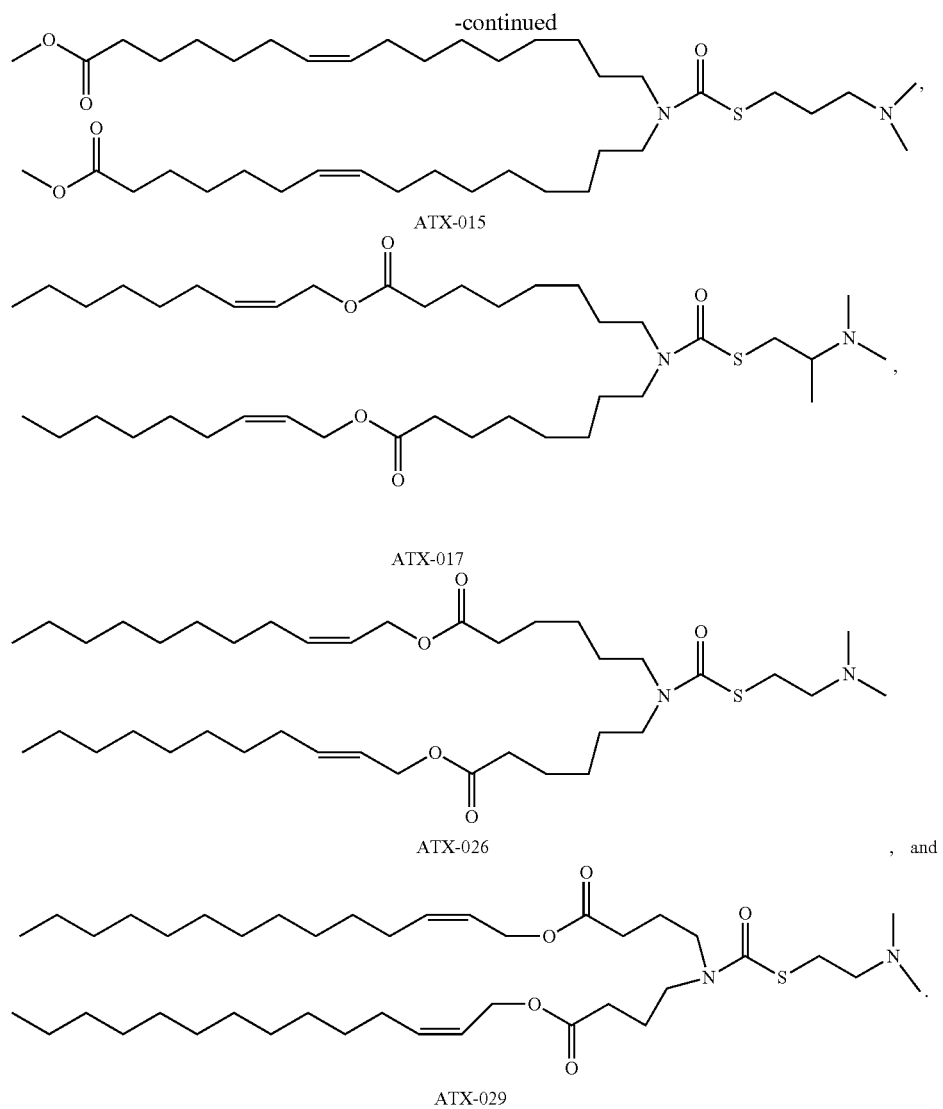

In other preferred embodiments, the lipid-NA nanoparticle encapsulates the nucleic acid; the lipid-NA nanoparticle has a size less than 100 nm; or the nucleic acid as a nucleotide length (nt) of 200-1000 nt, 1000-5000 nt, 5000-10,000 nt, or 10,000-25,000 nt. In other preferred embodiments, the nucleic acid is an mRNA; the nucleic acid is an DNA; the nucleic acid is self-replicating; or the nucleic acid encodes a viral protein.

Another aspect of the description is a method of treating a subject, comprising administering the pharmaceutical composition comprising a nucleic acid encoding a viral protein to the subject in an amount sufficient to cause production of antibody in serum of the subject. In preferred embodiments, the amount of the composition administered is sufficient to produce circulating antibodies; or to produce viral-specific CD8+ T cells in spleen of the subject; or to produce antigen-specific antibody detectable in a hemagglutination assay. In other preferred embodiments, administration is parenterally, most preferably by subcutaneous injection, intradermal injection, or intramuscular injection; or the pharmaceutical composition is administered at least twice. In another preferred embodiment, the method further comprising the step of measuring antibody titer or CD8+ T cells.

In another preferred embodiment, the pharmaceutical composition described herein comprises a nucleic acid that encodes an antibody. In another preferred embodiment, the antibody is capable of binding to a viral particle. Another aspect of the description is a method of treating a subject, comprising administering the pharmaceutical composition comprising a nucleic acid encoding the antibody to the subject to the subject in an amount sufficient to cause production of the antibody in serum of the subject.

DETAILED DESCRIPTION

Figure 1:
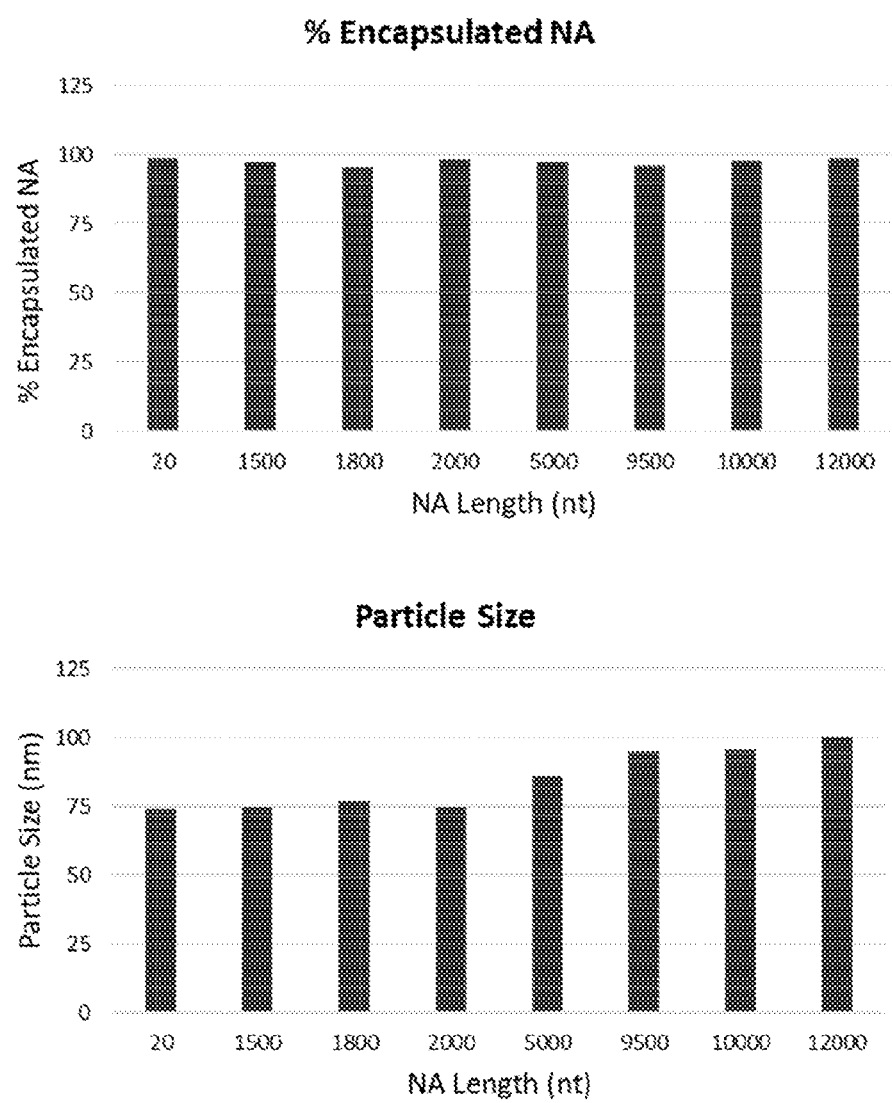
FIG. 1 shows lipid-NA nanoparticles successfully encapsulate nucleic acids (NA) of varying sizes. The percentage encapsulated nucleic acid (left) and particle diameter size in nm (right) is measured as disclosed herein. The NA length is given in nucleotides (nt).
Figure 2:
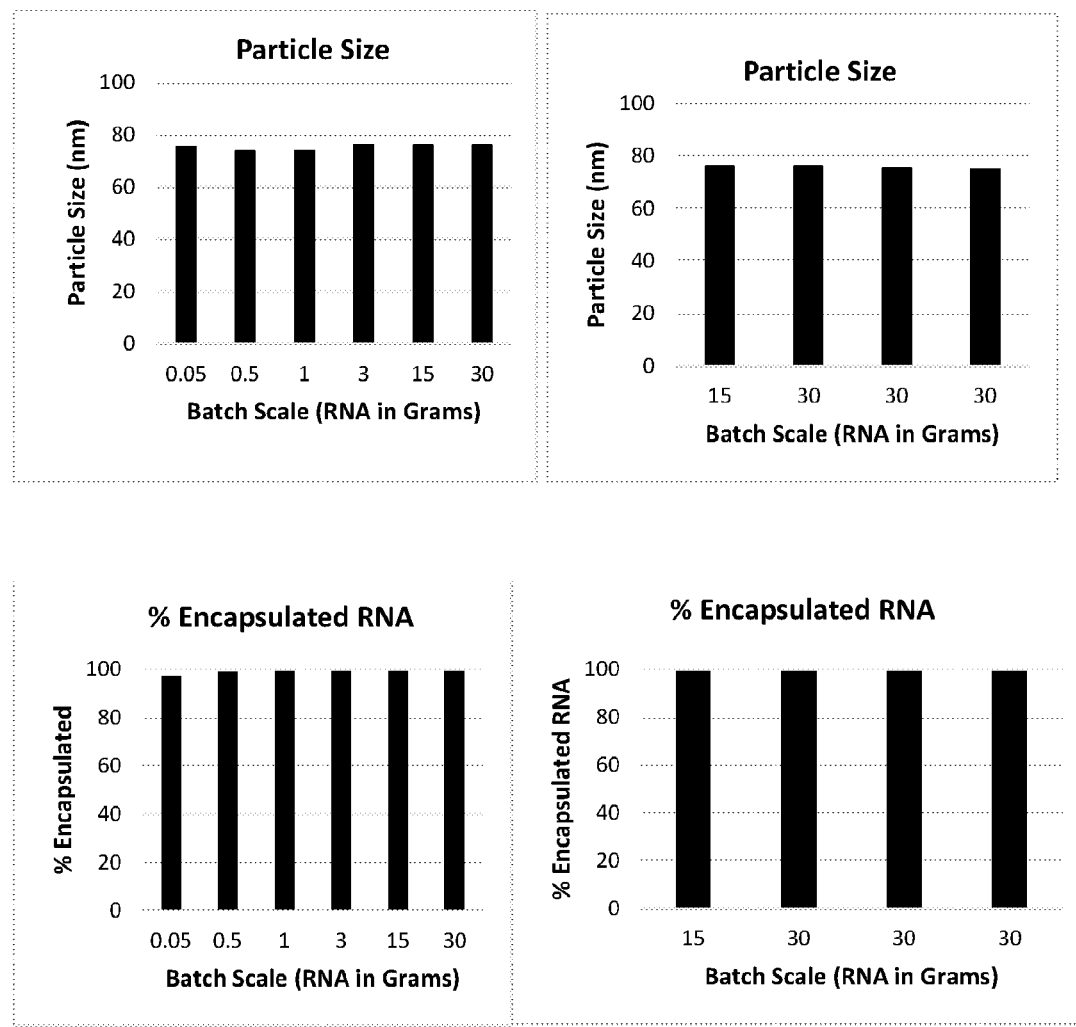
FIG. 2 shows the scalability and the reproducibility of the process of making the lipid-NA nanoparticles disclosed herein. The scalability is shown for particle size (nm) and percentage (%) encapsulation for batch sizes of 0.05 g, 0.5 g, 1 g, 3 g, 15 g, and 30 g RNA (see upper and lower left panels). The inter-batch reproducibility is shown for 15 g and 30 g batches (see upper and lower right panels).
Figure 3:
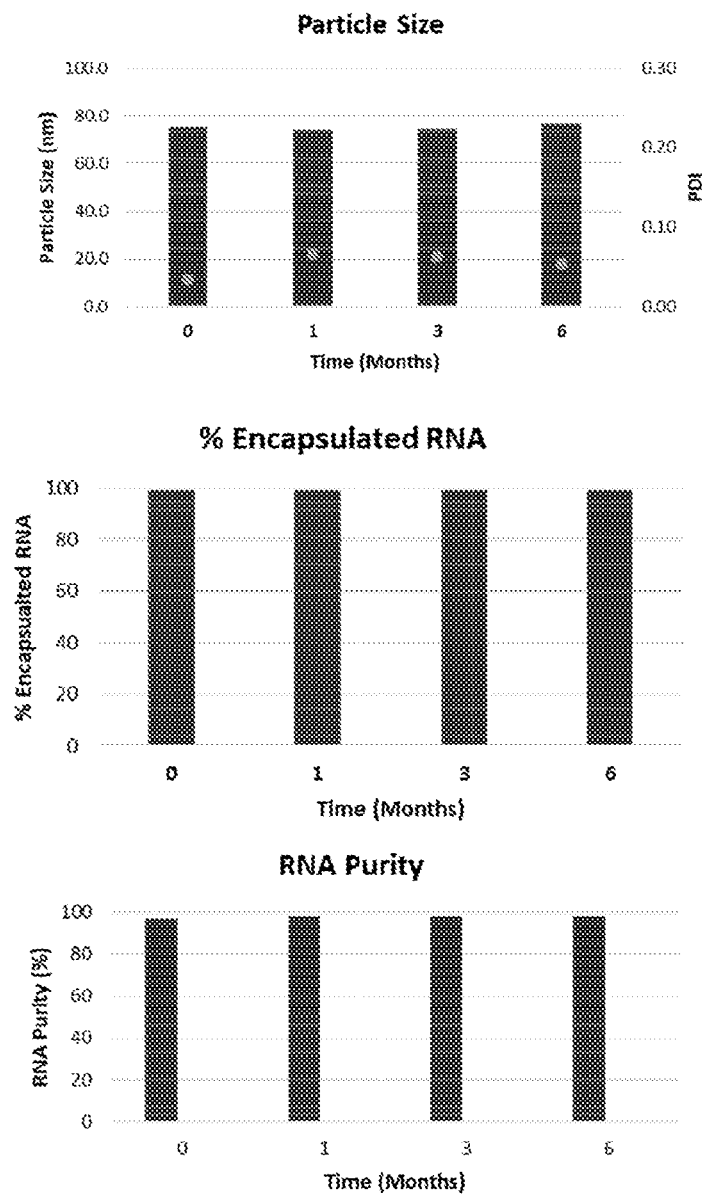
FIG. 3 shows the stability of the lipid-NA nanoparticles under frozen conditions, with respect to particle size (top left panel, diameter in nm), percentage encapsulation (top right panel) and percentage nucleic acid purity (bottom panel), initially (0), 1 month, 3 months, and six months.

Applicants have discovered a formulation comprising lipid-encapsulated nucleic acid nanoparticles for producing immunity. The nucleic acid encodes either an antibody or a viral antigen. Upon injection into a subject the nanoparticles cause accumulation of antigen-specific antibodies in the circulation. Further, when nanoparticles encapsulating nucleic acid encoding viral antigens are injected into a subject, antibodies positive in a hemagglutination reaction and antigen-specific CD8+ T cells are produced.

Definitions

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, ail numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

By "agent" is meant any small molecule chemical compound, antibody, nucleic acid molecule, or polypeptide, or fragments thereof.

A nucleic acid (NA, e.g., a polynucleotide or oligonucleotide) encoding a peptide may be used to produce an antigenic peptide in vitro. The NA may be, e.g., DNA, cDNA, PNA, CNA, RNA, either single- and/or double-stranded, or native or stabilized forms of polynucleotides, such as e.g., polynucleotides with a phosphorothioate backbone, or combinations thereof and it may or may not contain introns so long as it codes for the peptide. In one embodiment in vitro translation is used to produce the peptide. Many exemplary systems exist that one skilled in the art could utilize.

A lipid-NA nanoparticle preferably comprises a mRNA or an expression vector capable of expressing a polypeptide. Expression vectors for different cell types are well known in the art and can be selected without undue experimentation. Generally, the DNA is inserted into an expression vector, such as a plasmid, in proper orientation and correct reading frame for expression, if necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) MOLECULAR CLONING, A LABORATORY MANUAL, Cold Spring Harbor Laboratory, NY).

The term "nucleic acid encoding a polypeptide" encompasses a NA that includes only coding sequences for the polypeptide as well as a NA that includes additional coding and/or non-coding sequences. NA can be in the form of RNA or in the form of DNA. DNA includes cDNA, genomic DNA, and synthetic DNA; and can be double-stranded or single-stranded, and if single stranded can be the coding strand or non-coding (anti-sense) strand.

The NA may comprise the coding sequence for the peptide, either an antibody or an antigen, fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide.

A NA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. An oligomer containing a NA sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding antibodies or antigenic peptides. Recombinant expression vectors are replicable DNA constructs having synthetic or cDNA-derived DNA fragments operatively linked to suitable transcriptional or translational regulator elements derived from mammalian, microbial, viral or insect genes. A transcriptional unit generally comprises an assembly of a genetic element or elements having a regulatory role in gene expression, for example, transcriptional promoters or enhancers, a structural or coding sequence which is transcribed into mRNA and translated into protein, and appropriate transcription and translation initiation and termination sequences, as described in detail herein. Such regulatory elements can include an operator sequence to control transcription. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

"Ribonucleic acid" or "RNA" refers to a polymer containing at least two ribonucleotides. "Ribonucleotides" contain a sugar ribose, a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkyl halides.

RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), self-replicating RNA, ribozymes, chimeric sequences, or derivatives of these groups.

The RNA can include (in addition to any 5' cap structure) one or more nucleotides having a modified nucleobase, including m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms216A (2-methylthio-N6isopentenyladenosine); io6A (N6-(cis-hydroxyisopentenyl)adenosine); ms2106A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O- methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cmnm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide.

The RNA may comprise one or more UNA molecules, e.g., as disclosed in U.S. Pat. Nos. 8,314,227, 9,051,570, 9,303,260, 9,297,009, and 9,340,789, and U.S. Patent Publication No. 2016/0168567, incorporated herein in their entirety.

The RNA or self-replicating RNA can include one or more modified pyrimidine nucleobases, such as pseudouridine and/or 5-methylcytosine residues.

The RNA may include a 5' cap comprising a 7'-methylguanosine, and the first 1, 2 or 3 5' ribonucleotides may be methylated at the 2' position of the ribose. The RNA can contain a 5' trinucleotide cap structure as described by Tanis, et al., U.S. application Ser. No. 15/788,742, filed Oct. 19, 2017, herein incorporated by reference in its entirety.

Natural RNA have a phosphate backbone, RNA as described herein may contain other types of backbones and bases including peptide nucleic acids, phosphothionates, phosphoramidate, phosphorothioate, and/or methylphosphonate linkages.

"Antisense" is a polynucleotide that interferes with the function of DNA and/or RNA. This may result in suppression of expression.

"Gene" refers to a nucleic acid (e.g., DNA) sequence that comprises coding sequences necessary for the production of a polypeptide or precursor (e.g., herpes simplex virus). The polypeptide can be encoded by a full length coding sequence or by any portion of the coding sequence so long as the desired activity or functional properties (e.g., enzymatic activity, ligand binding, signal transduction, and the like) of the full-length polypeptide or fragment thereof are retained.

"Aqueous solution" refers to a composition comprising in whole, or in part, water.

"Organic lipid solution" refers to a composition comprising in whole, or in part, an organic solvent having a lipid. The organic lipid solution preferably comprises an alkanol, most preferably ethanol.

"Lipid" refers to a group of organic compounds that are esters of fatty acids and are characterized by being insoluble in water but soluble in many organic solvents, e.g., fats, oils, waxes, phospholipids, glycolipids, and steroids.

"Amphipathic lipid" comprises a lipid in which hydrophilic characteristics derive from the presence of polar or charged groups such as carbohydrates, phosphato, carboxylic, sulfato, amino, sulfhydryl, nitro, hydroxy and other like groups, and hydrophobic characteristics can be conferred by the inclusion of a polar groups that include, but are not limited to, long chain saturated and unsaturated aliphatic hydrocarbon groups and such groups substituted by one or more aromatic, cycloaliphatic or heterocyclic group(s). Examples include phospholipids, aminolipids and sphingolipids. Phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Amphipathic lipids also can lack phosphorus, such as sphingolipid, glycosphingolipid families, diacylglycerols and β-acyloxyacids.

"Anionic lipid" is any lipid that is negatively charged at physiological pH, including phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, and other anionic modifying groups joined to neutral lipids.

"Cationic lipid" carry a net positive charge at a selective pH, such as physiological pH, including N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN®, LIPOFECTAMINE®, and TRANSFECTAM®.

An "ionizable cationic lipid" carry a charge that is pH-dependent. Ionizable cationic lipids include those disclosed in U.S. Pat. Nos. 9,593,077, 9,365,610, 9,567,296, 9,580,711, and 9,670,152, and U.S. Patent Application Publication Nos. 2017/0190661 and 2017/0114010, incorporated herein by reference in their entirety. Ionizable cationic lipids may include a lipid selected from the following Tables 1, 2, 3, or 4.

TABLE 1
ATX-001
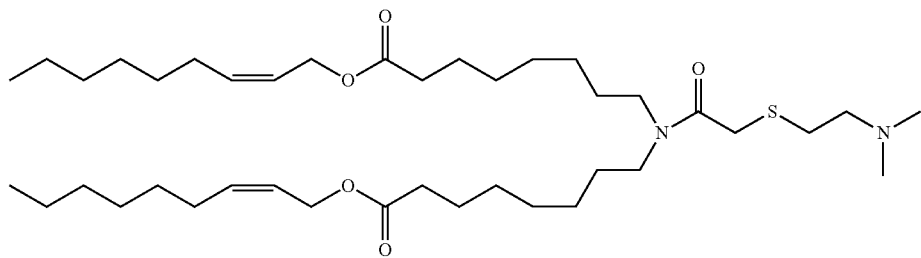 [SMILES: CCCCCC/C=C\COC(=O)CCCCCCCN(CCCCCCCC(=O)OC/C=C\CCCCCC)C(=O)CSCCN(C)C]
ATX-002
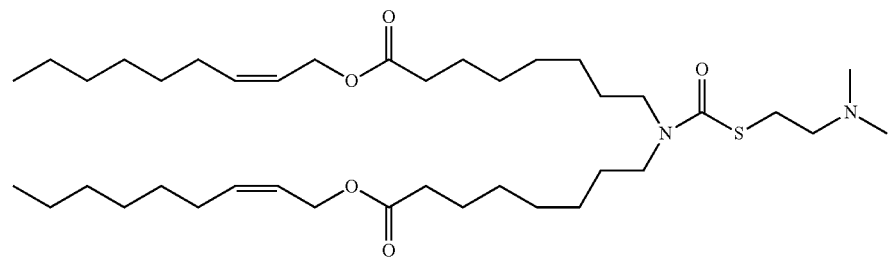 [SMILES: CCCCCC/C=C\COC(=O)CCCCCCCN(CCCCCCCC(=O)OC/C=C\CCCCCC)C(=O)SCCN(C)C]
ATX-003
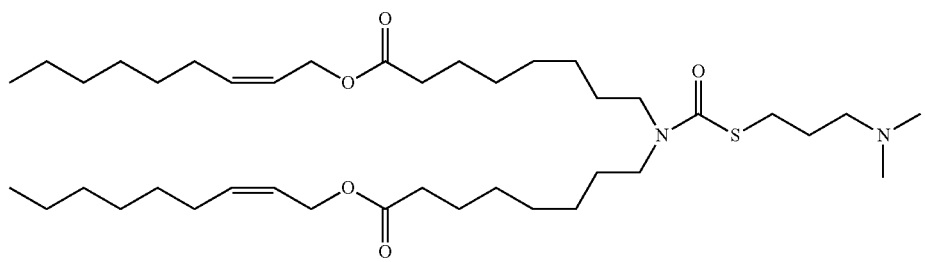 [SMILES: CCCCCC/C=C\COC(=O)CCCCCCCN(CCCCCCCC(=O)OC/C=C\CCCCCC)C(=O)SCCCN(C)C]
ATX-004
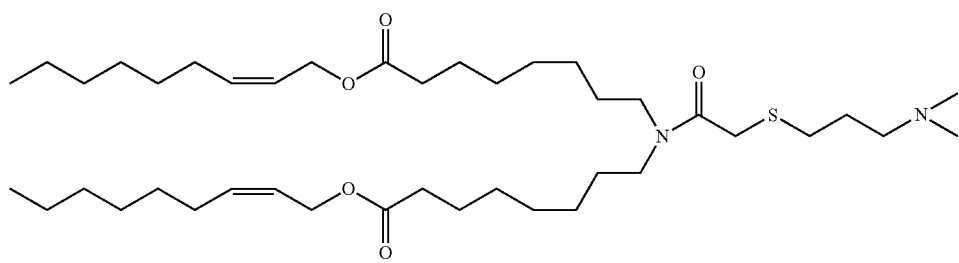 [SMILES: CCCCCC/C=C\COC(=O)CCCCCCCN(CCCCCCCC(=O)OC/C=C\CCCCCC)C(=O)CSCCCN(C)C]
ATX-005
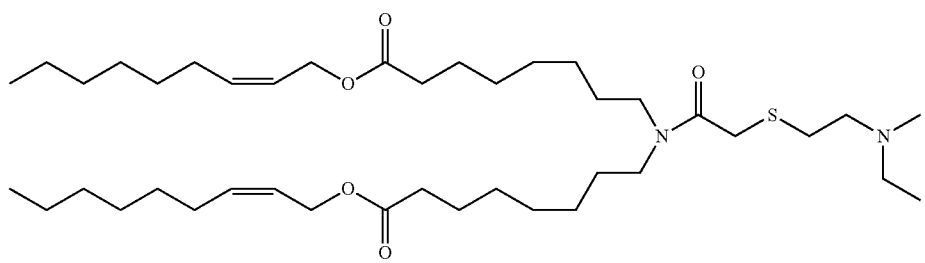
ATX-006
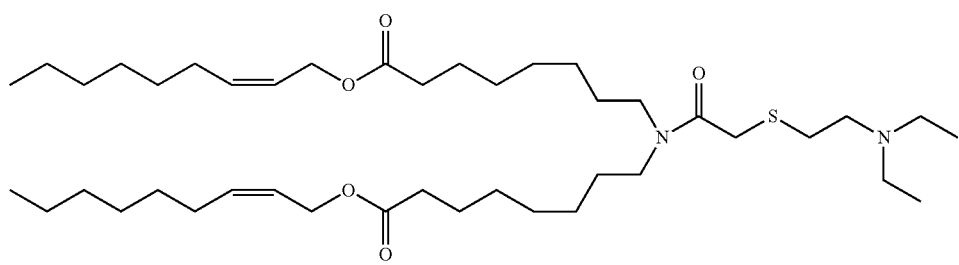 [SMILES: CCCCCC/C=C\COC(=O)CCCCCCCN(CCCCCCCC(=O)OC/C=C\CCCCCC)C(=O)CSCCN(CC)CC]

TABLE 1-continued
ATX-007
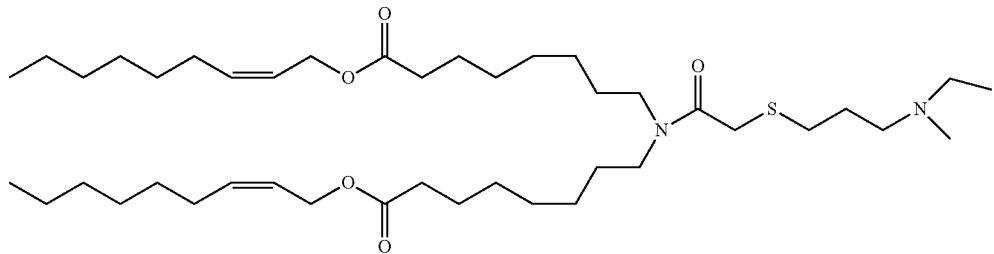 [SMILES: CCCCCC/C=C\COC(=O)CCCCCCCN(CCCCCCCC(=O)OC/C=C\CCCCCC)C(=O)CSCCCN(C)CC]
ATX-008
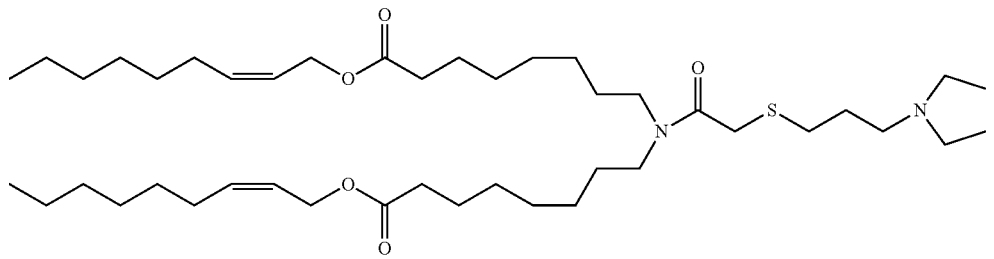 [SMILES: CCCCCC/C=C\COC(=O)CCCCCCCN(CCCCCCCC(=O)OC/C=C\CCCCCC)C(=O)CSCCCN(CC)CC]
ATX-009
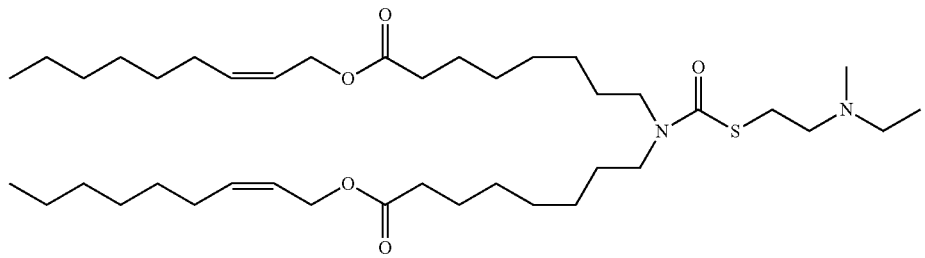 [SMILES: CCCCCC/C=C\COC(=O)CCCCCCCN(CCCCCCCC(=O)OC/C=C\CCCCCC)C(=O)SCCN(C)CC]
ATX-010
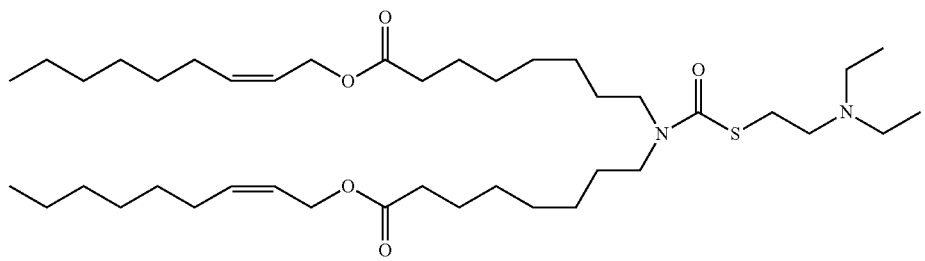 [SMILES: CCCCCC/C=C\COC(=O)CCCCCCCN(CCCCCCCC(=O)OC/C=C\CCCCCC)C(=O)SCCN(CC)CC]
ATX-011
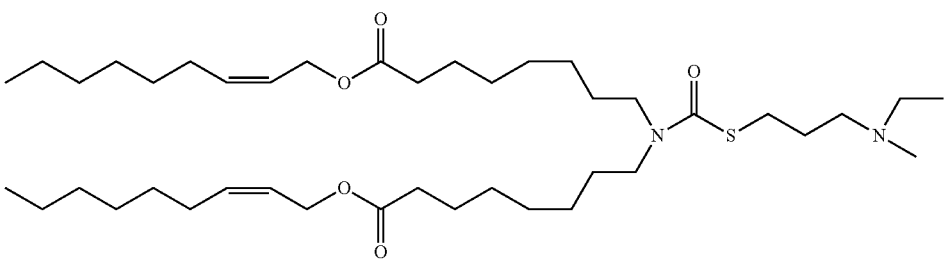 [SMILES: CCCCCC/C=C\COC(=O)CCCCCCCN(CCCCCCCC(=O)OC/C=C\CCCCCC)C(=O)SCCCN(C)CC]
ATX-012
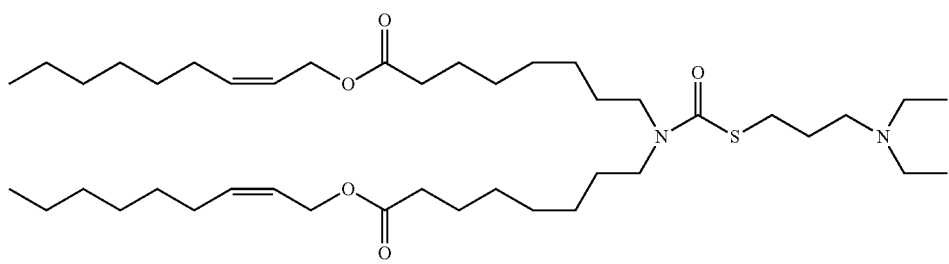 [SMILES: CCCCCC/C=C\COC(=O)CCCCCCCN(CCCCCCCC(=O)OC/C=C\CCCCCC)C(=O)SCCCN(CC)CC]

TABLE 1-continued
ATX-013
ATX-014
ATX-015
ATX-016
ATX-017
ATX-018
ATX-019
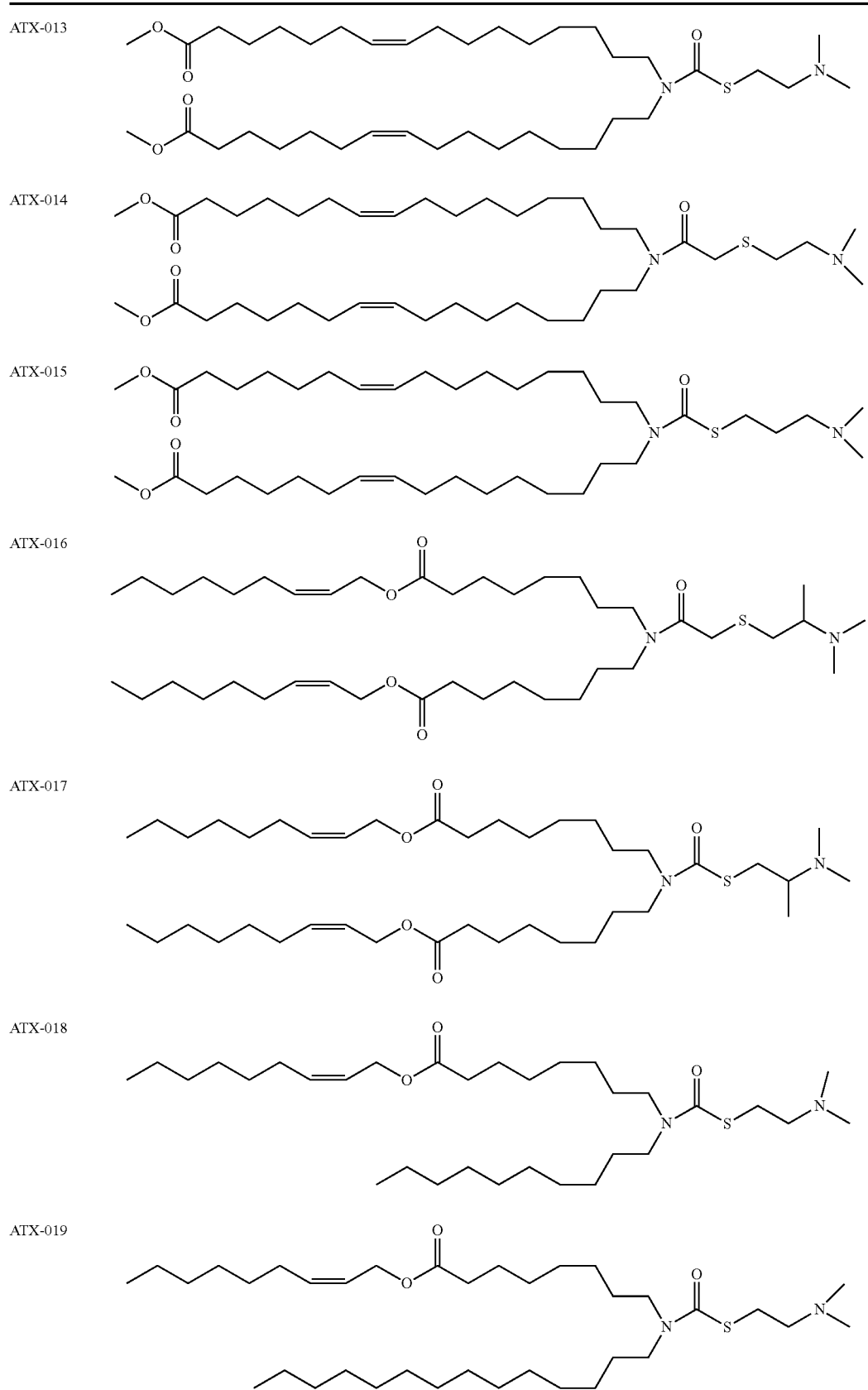

TABLE 1-continued
ATX-020
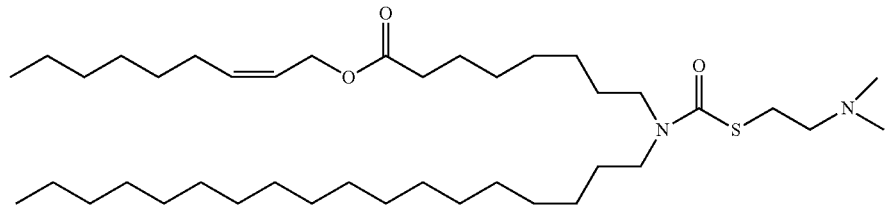 [SMILES: CCCCCC/C=C\COC(=O)CCCCCCCN(CCCCCCCCCCCCCCCCCC)C(=O)SCCN(C)C]
ATX-021
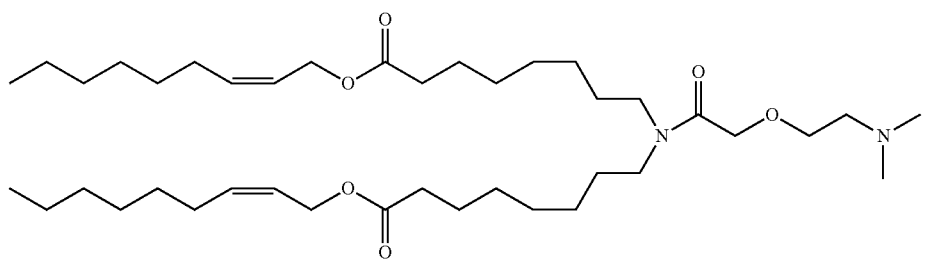 [SMILES: CCCCCC/C=C\COC(=O)CCCCCCCN(CCCCCCCC(=O)OC/C=C\CCCCCC)C(=O)COCCN(C)C]
ATX-022
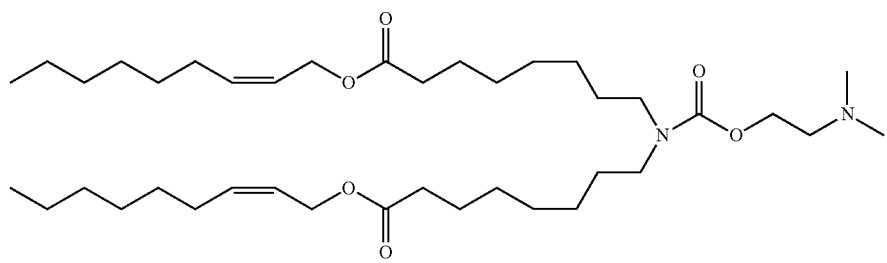 [SMILES: CCCCCC/C=C\COC(=O)CCCCCCCN(CCCCCCCC(=O)OC/C=C\CCCCCC)C(=O)OCCN(C)C]
ATX-023
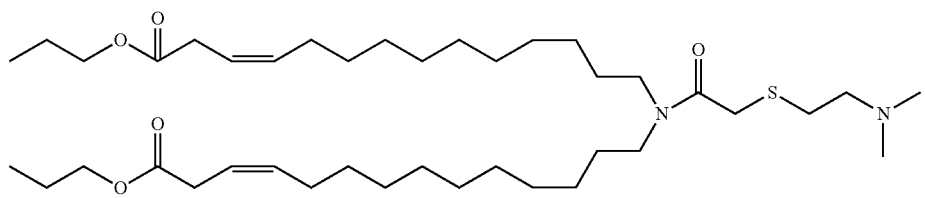 [SMILES: CCCOC(=O)C/C=C\CCCCCCCCCCN(CCCCCCCCCC/C=C\CC(=O)OCCC)C(=O)CSCCN(C)C]
ATX-024
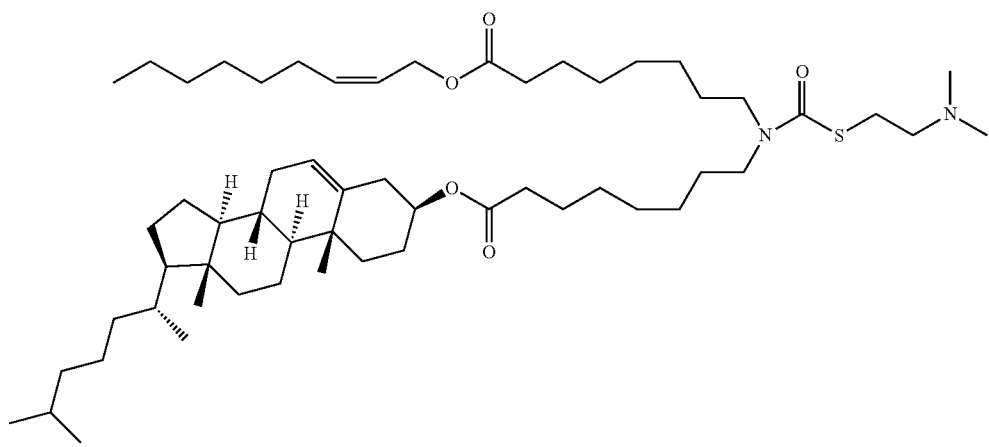

TABLE 1-continued
ATX-025
ATX-026
ATX-027
ATX-028
ATX-029
ATX-030
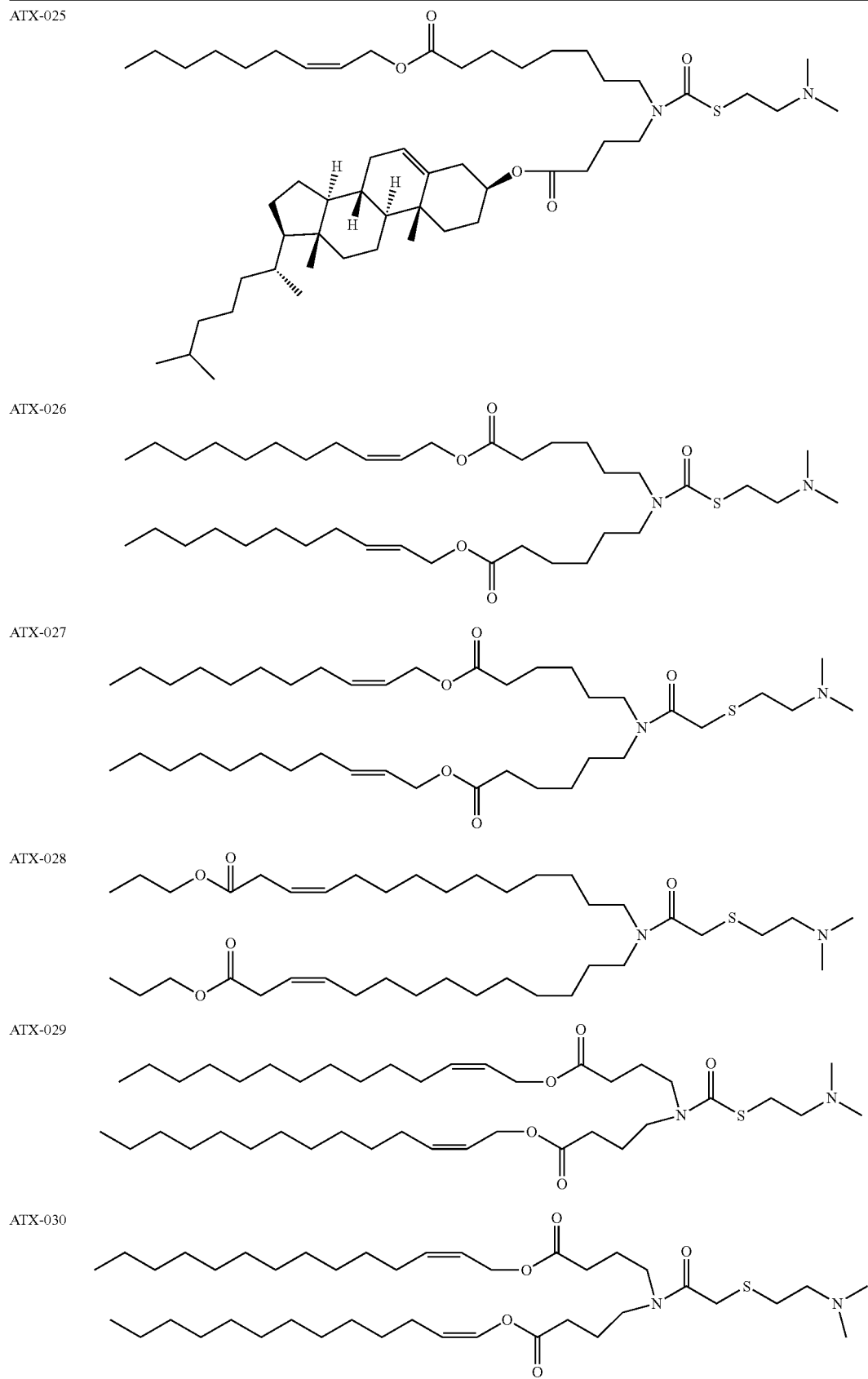

TABLE 1-continued
ATX-031
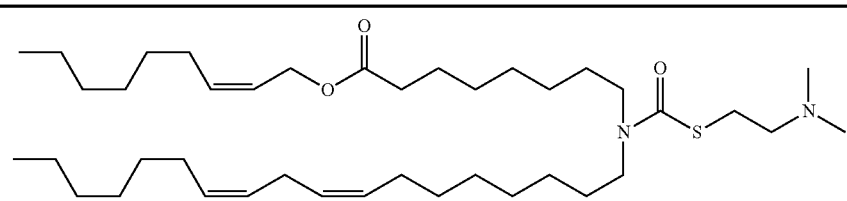
ATX-032
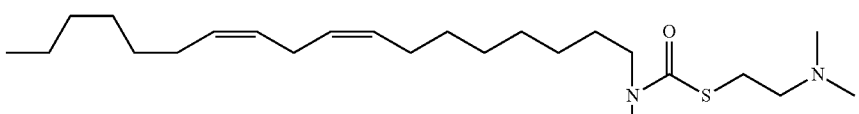
TABLE 2
ATX-B-1
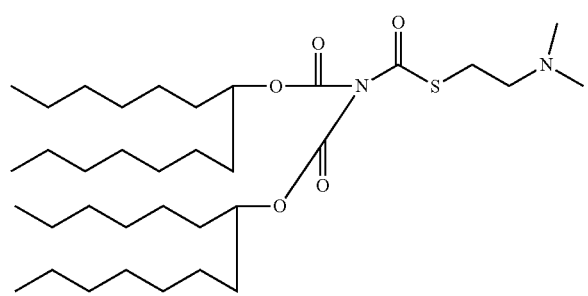 [SMILES: CCCCCCCCC(CCCCCC)OC(=O)N(C(=O)OC(CCCCCC)CCCCCCCC)C(=O)SCCN(C)C]
ATX-B-2
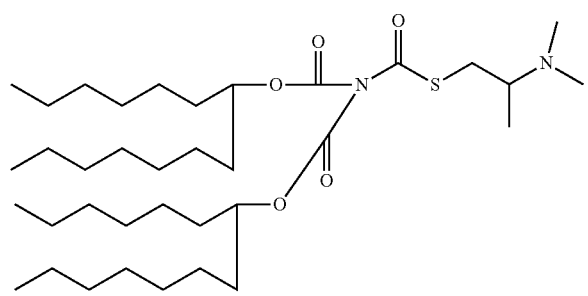 [SMILES: CCCCCCCCC(CCCCCC)OC(=O)N(C(=O)OC(CCCCCC)CCCCCCCC)C(=O)SCC(C)N(C)C]
ATX-B-3
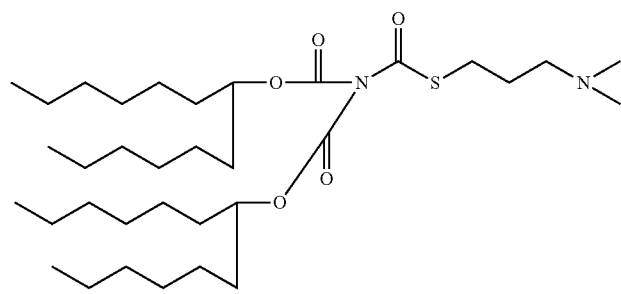 [SMILES: CCCCCCCC(CCCCCC)OC(=O)N(C(=O)OC(CCCCCC)CCCCCCC)C(=O)SCCCN(C)C]

TABLE 2-continued
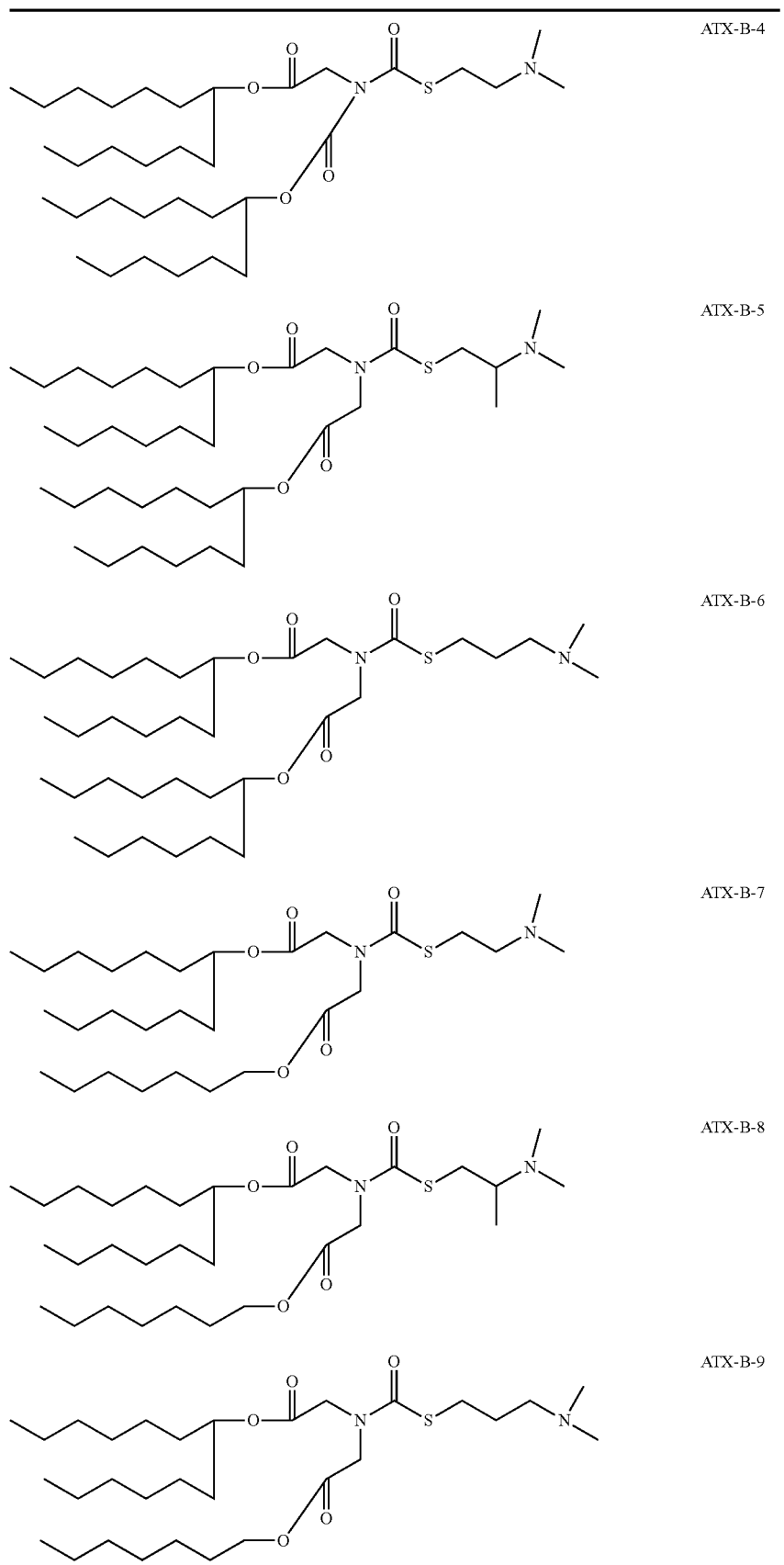

TABLE 2-continued
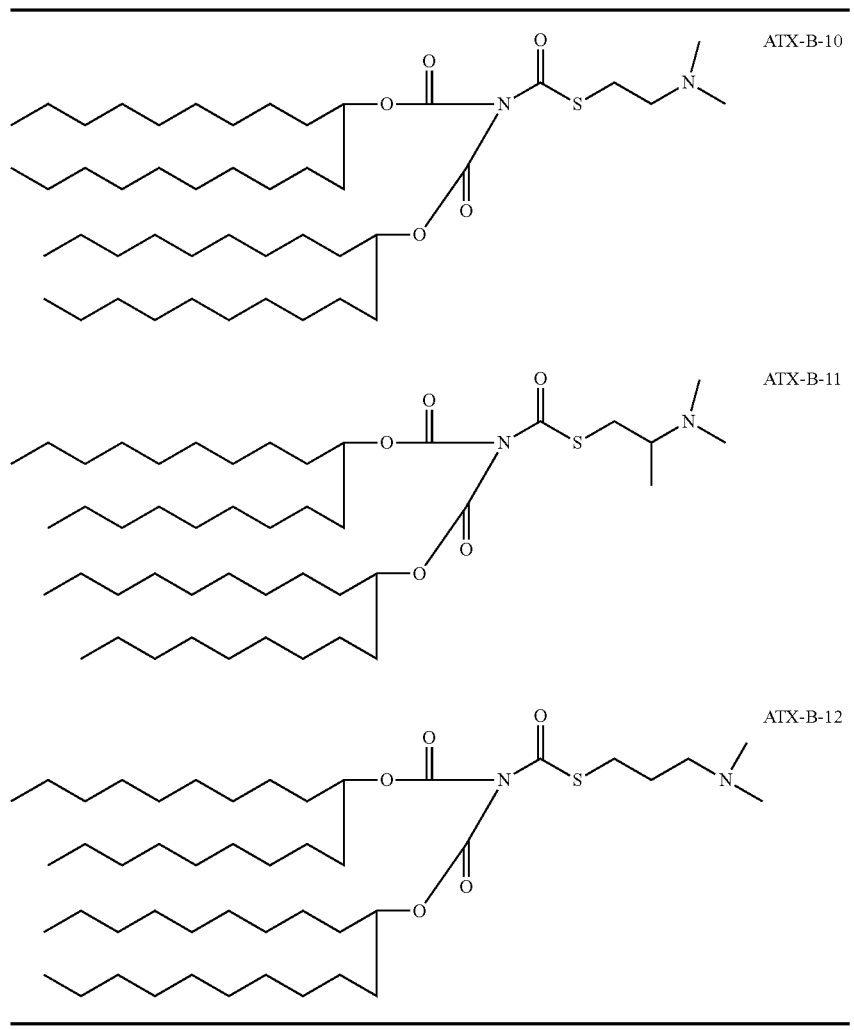
TABLE 3
| Compound | ATX-# |
|---|---|
| | 0063 |

TABLE 3-continued

| Compound | ATX-# |
|---|---|
| [structure] | 0130 |
| [structure] | 0131 |
| [structure] | 0044 |

TABLE 3-continued
| Compound | ATX-# |
|---|---|
| 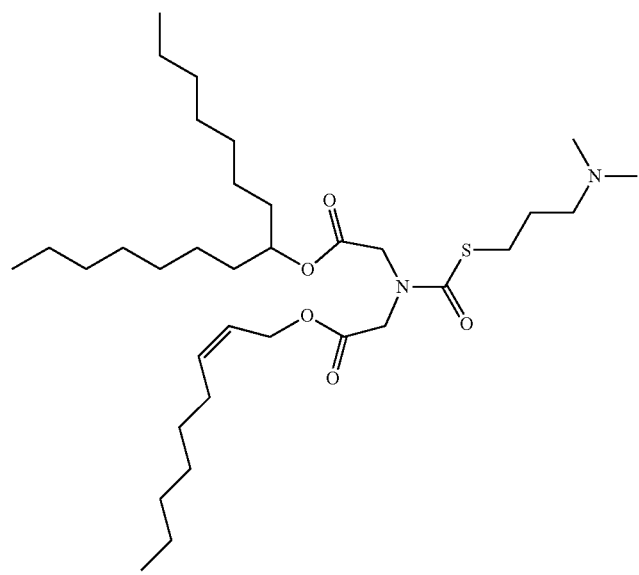 [SMILES: CCCCCC/C=C\COC(=O)CN(CC(=O)OC(CCCCCCC)CCCCCCC)C(=O)SCCCN(C)C] | 0111 |
| 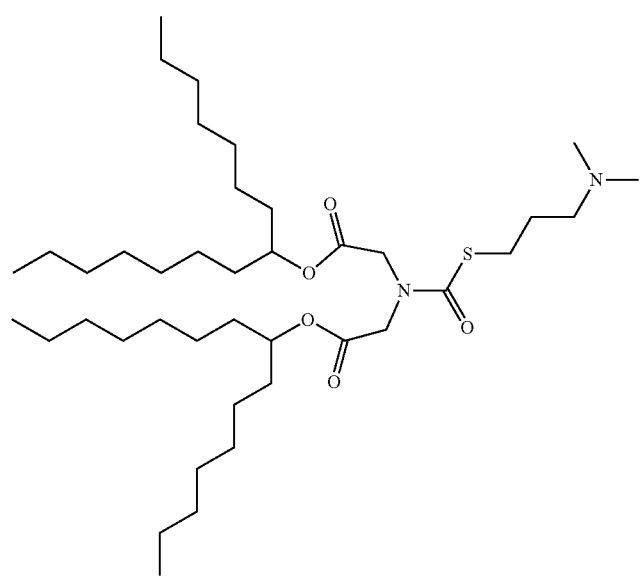 [SMILES: CCCCCCCC(CCCCCCC)OC(=O)CN(CC(=O)OC(CCCCCCC)CCCCCCC)C(=O)SCCCN(C)C] | 0132 |

TABLE 3-continued
| Compound | ATX-# |
|---|---|
| 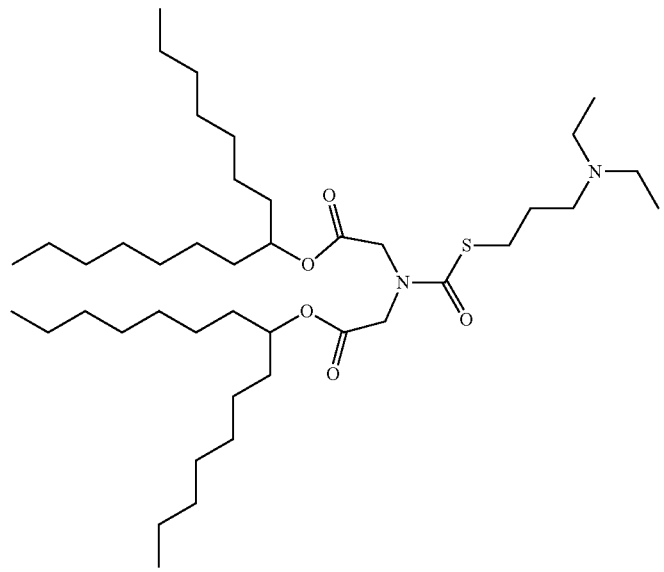 [SMILES: CCCCCCCC(CCCCCCC)OC(=O)CN(CC(=O)OC(CCCCCCC)CCCCCCC)C(=O)SCCCN(CC)CC] | 0134 |
| 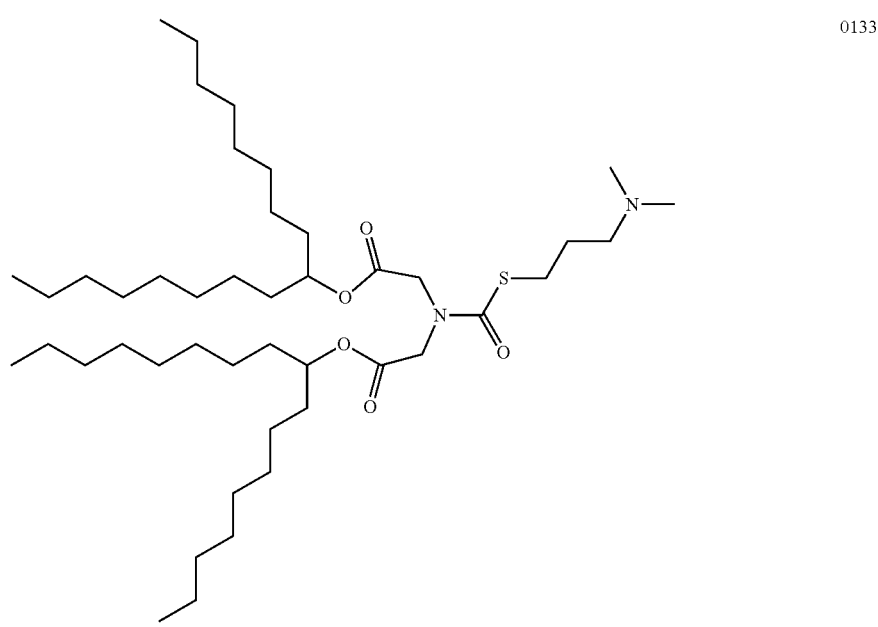 | 0133 |

TABLE 3-continued
| Compound | ATX-# |
|---|---|
| 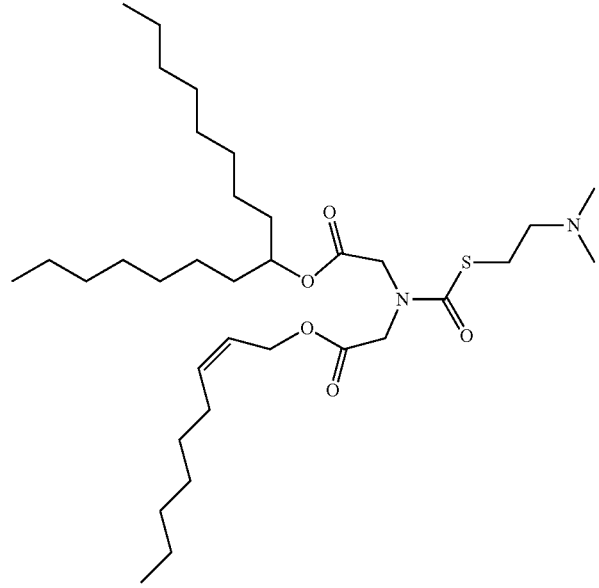 [SMILES: CCCCCC/C=C\COC(=O)CN(CC(=O)OC(CCCCCCC)CCCCCCCC)C(=O)SCCN(C)C] | 0064 |
| 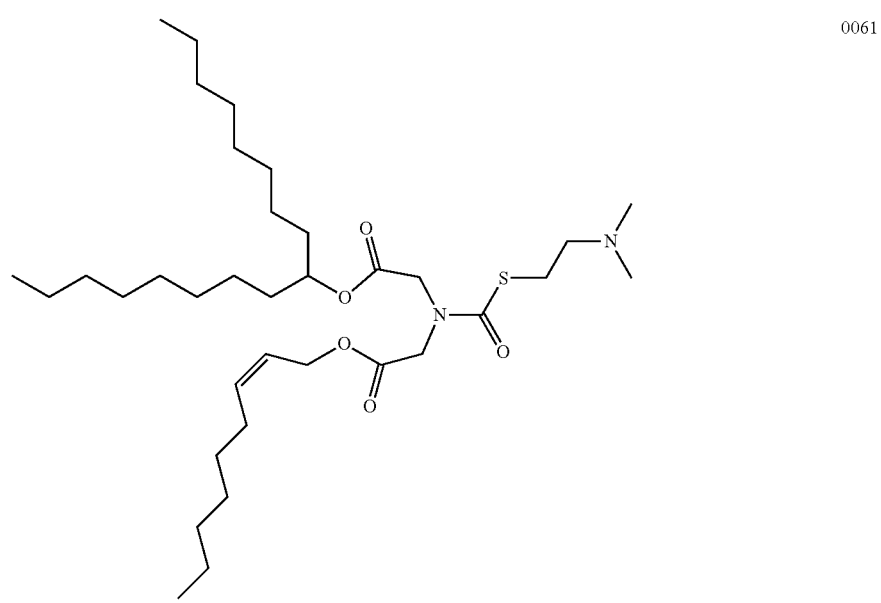 | 0061 |

TABLE 3-continued
| Compound | ATX-# |
|---|---|
| 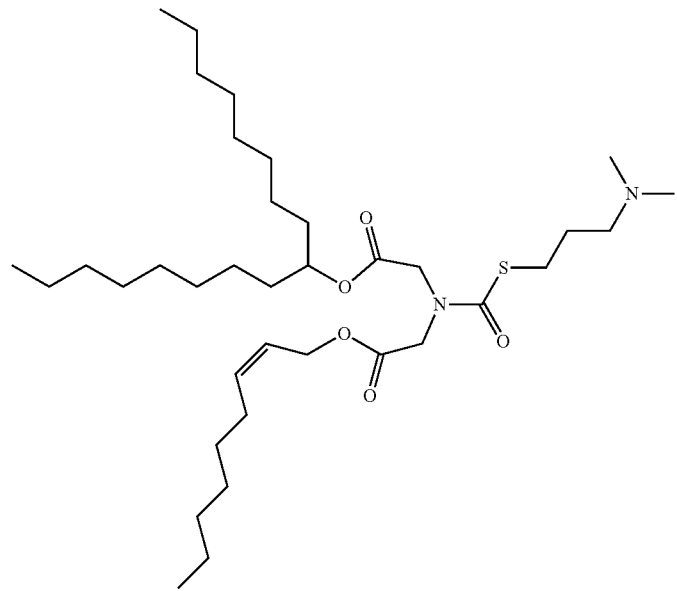 [SMILES: CCCCCC/C=C\COC(=O)CN(CC(=O)OC(CCCCCCCC)CCCCCCCC)C(=O)SCCCN(C)C] | 0100 |
| 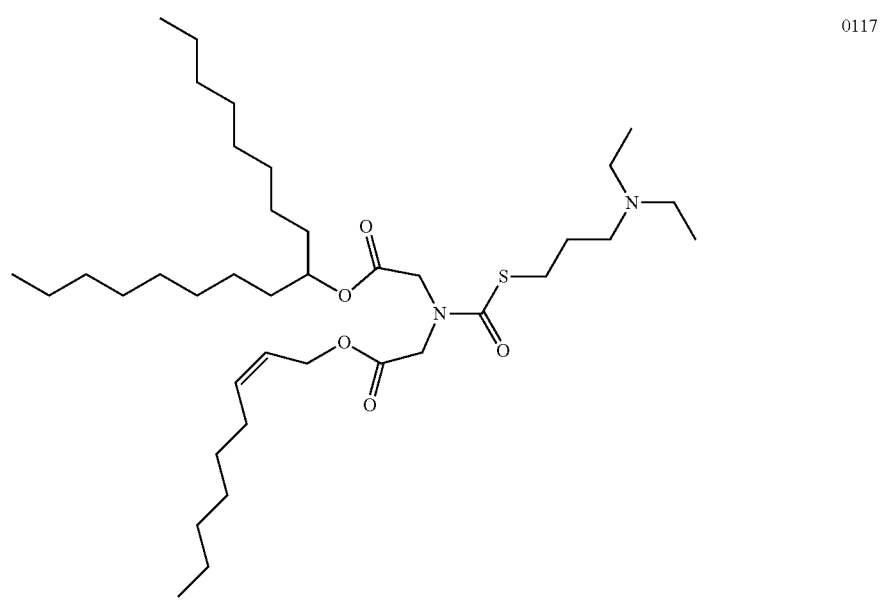 | 0117 |

TABLE 3-continued
| Compound | ATX-# |
|---|---|
| 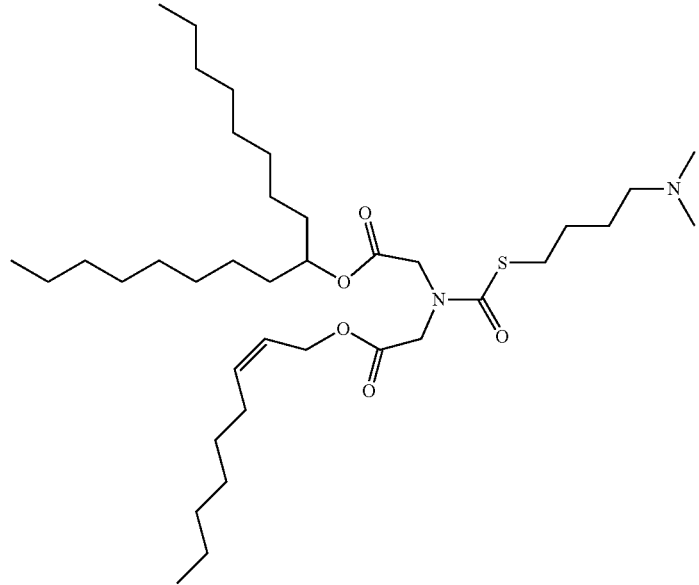 [SMILES: CCCCCC/C=C\COC(=O)CN(CC(=O)OC(CCCCCCCC)CCCCCCCC)C(=O)SCCCCN(C)C] | 0114 |
| 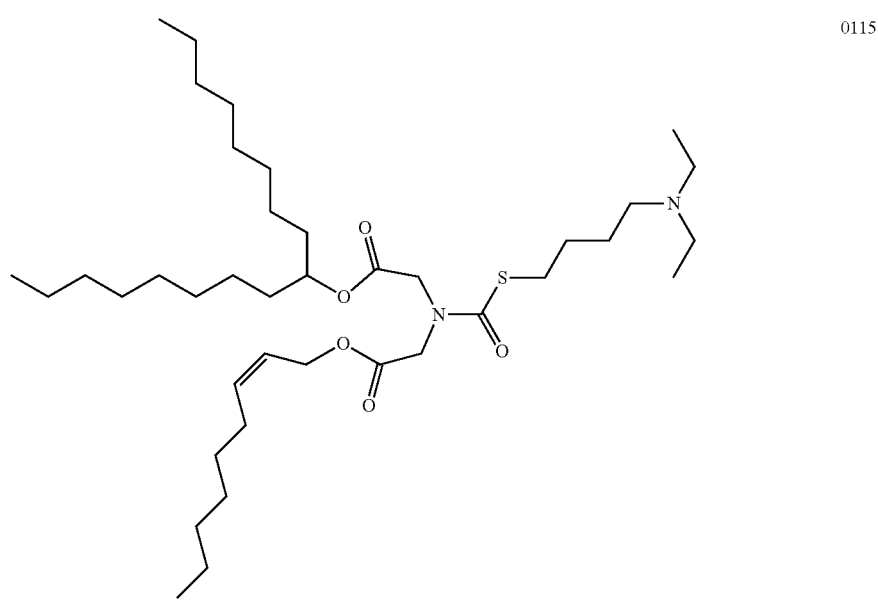 | 0115 |

TABLE 3-continued
| Compound | ATX-# |
|---|---|
| 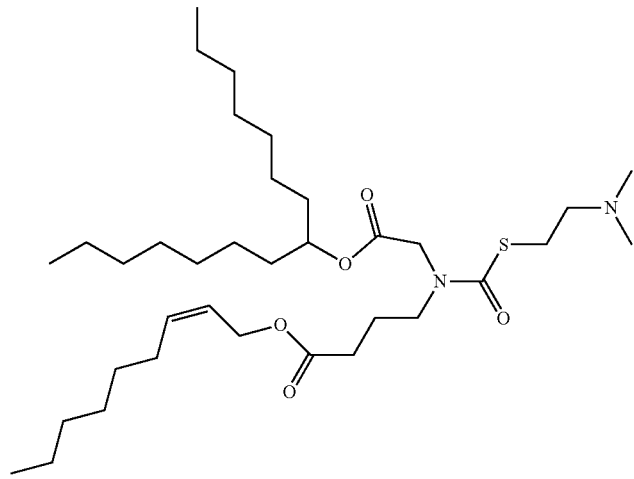 [SMILES: CCCCCC/C=C\COC(=O)CCCN(CC(=O)OC(CCCCCCC)CCCCCCC)C(=O)SCCN(C)C] | 0101 |
| 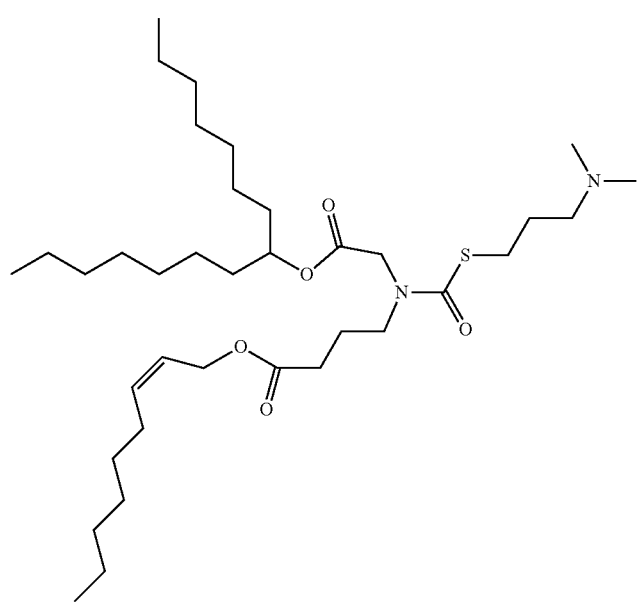 [SMILES: CCCCCC/C=C\COC(=O)CCCN(CC(=O)OC(CCCCCCC)CCCCCCC)C(=O)SCCCN(C)C] | 0106 |

TABLE 3-continued
| Compound | ATX-# |
|---|---|
| 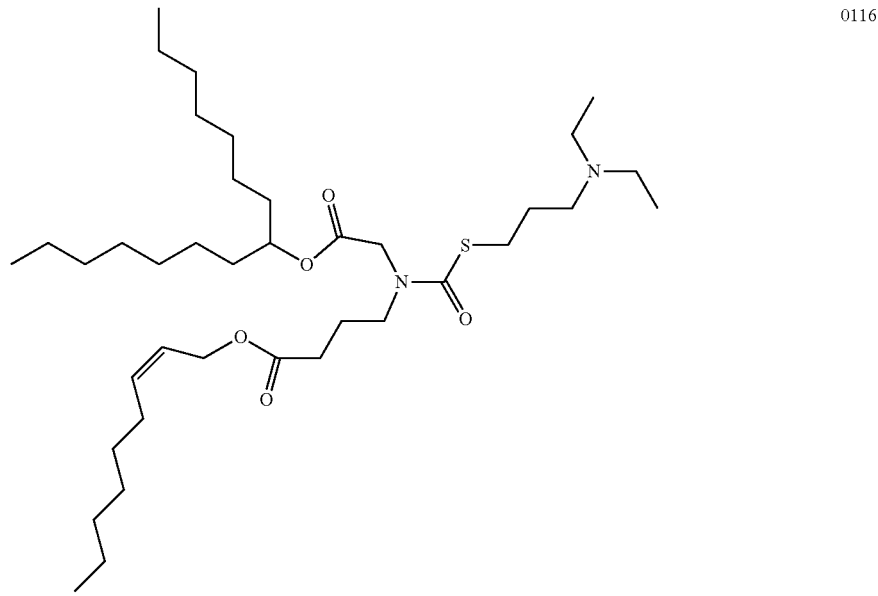 | 0116 |
| 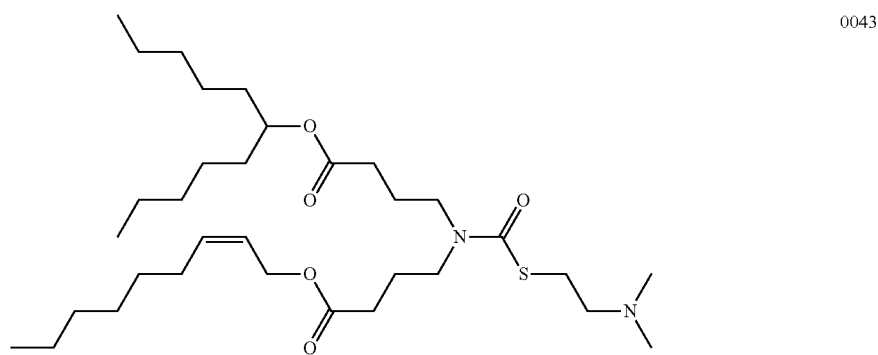 | 0043 |
| 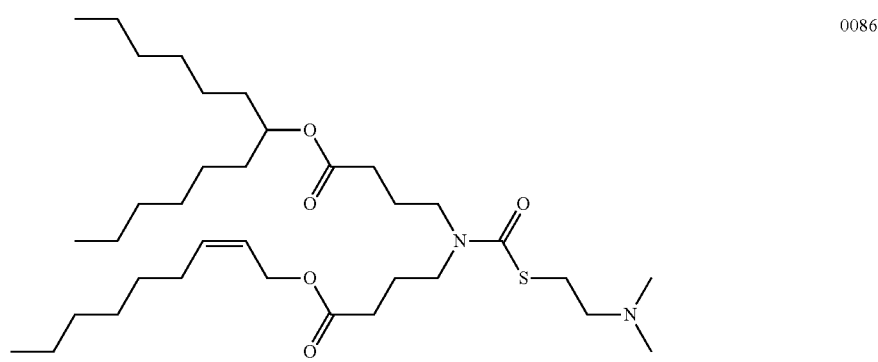 | 0086 |

TABLE 3-continued
| Compound | ATX-# |
|---|---|
| 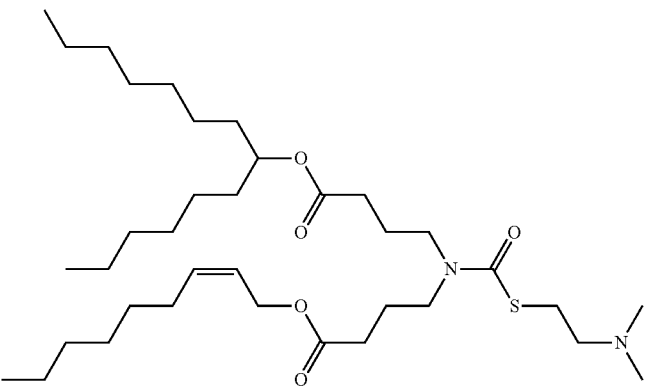 [SMILES: CCCCCC/C=C\COC(=O)CCCN(CCCC(=O)OC(CCCCCC)CCCCCCC)C(=O)SCCN(C)C] | 0058 |
| 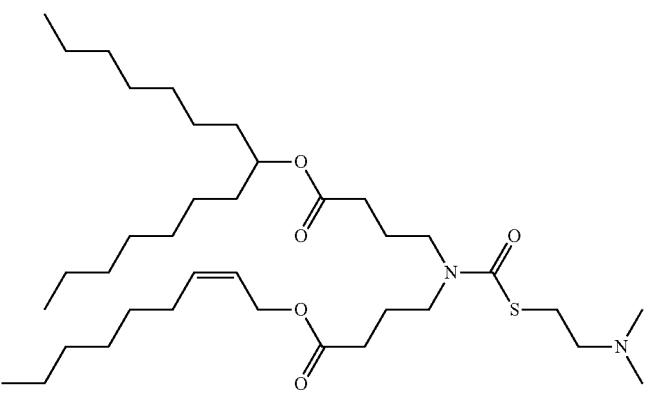 [SMILES: CCCCCC/C=C\COC(=O)CCCN(CCCC(=O)OC(CCCCCCC)CCCCCCC)C(=O)SCCN(C)C] | 0081 |
| 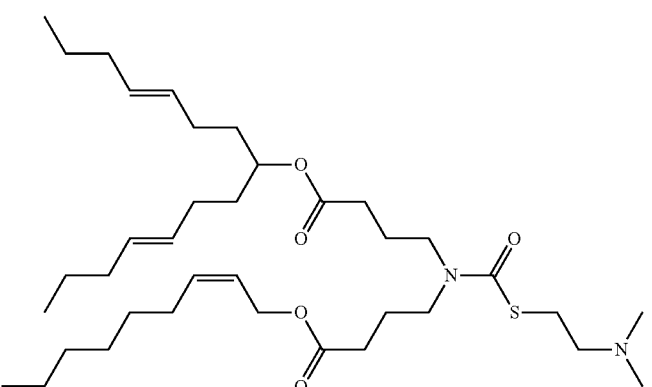 | 0123 |
| 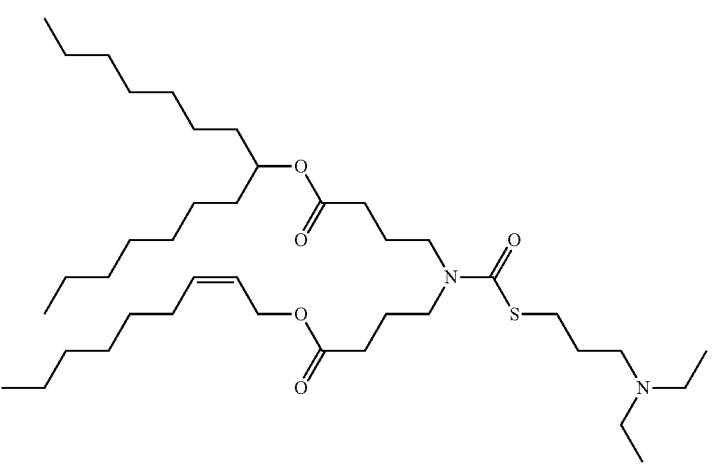 [SMILES: CCCCCC/C=C\COC(=O)CCCN(CCCC(=O)OC(CCCCCCC)CCCCCCC)C(=O)SCCCN(CC)CC] | 0122 |

TABLE 3-continued
| Compound | ATX-# |
|---|---|
| 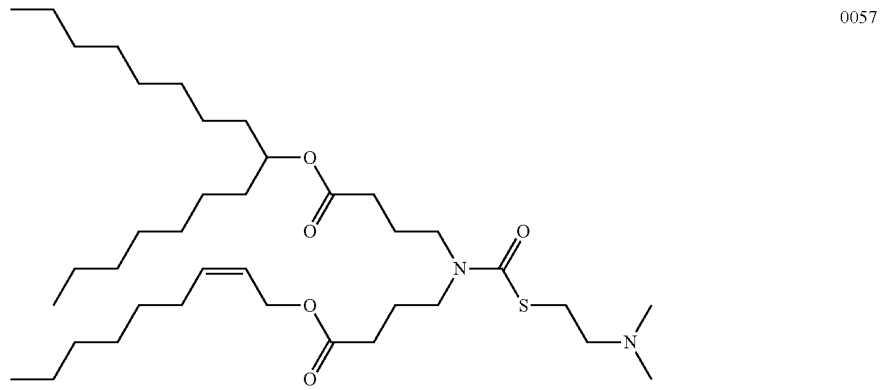 | 0057 |
| 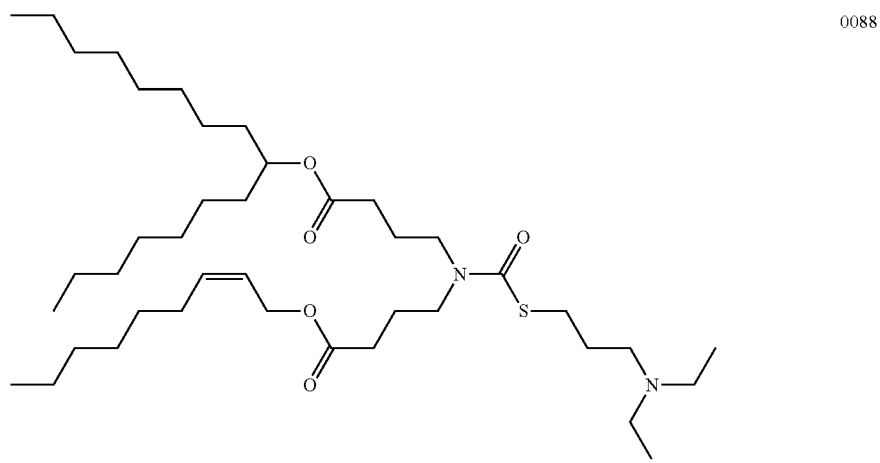 | 0088 |
| 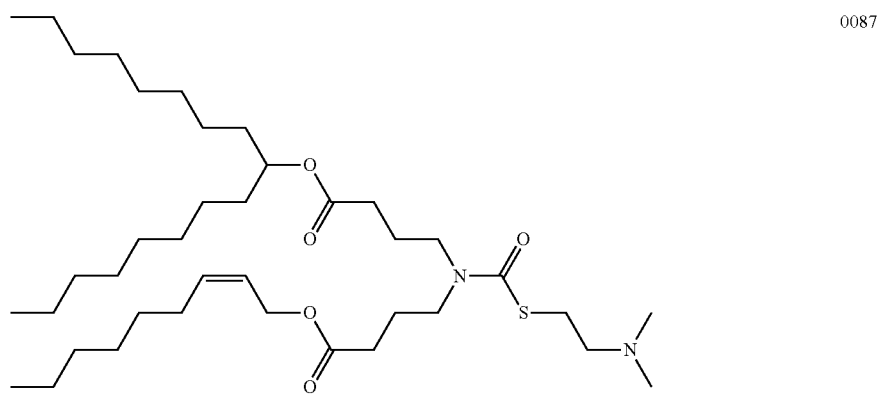 | 0087 |

TABLE 3-continued

| Compound | ATX-# |
|---|---|
| | 0124 |
| | 0128 |
| | 0127 |

TABLE 3-continued
| Compound | ATX-# |
|---|---|
| 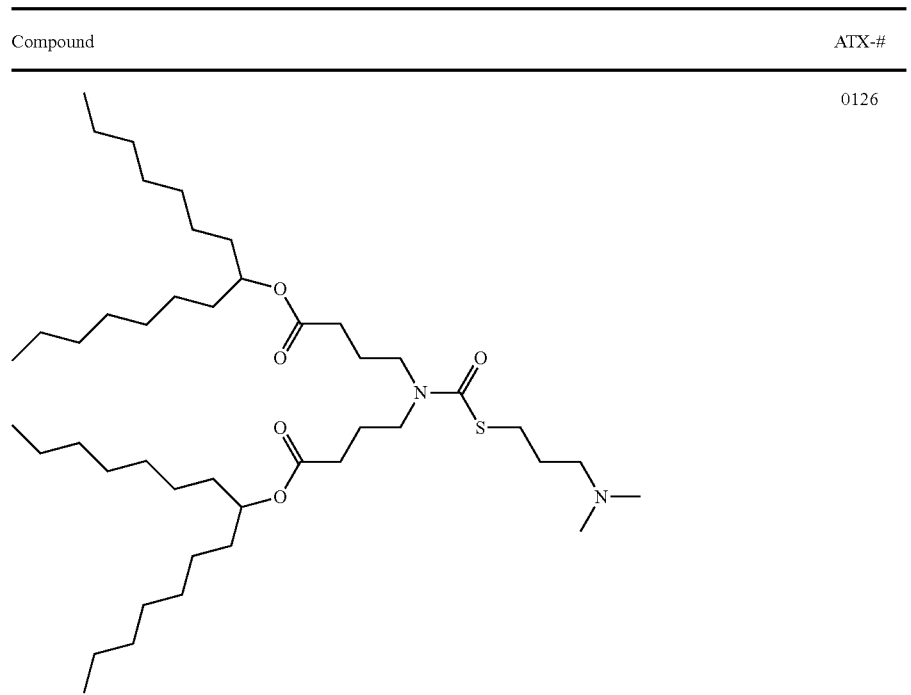 | 0126 |
| 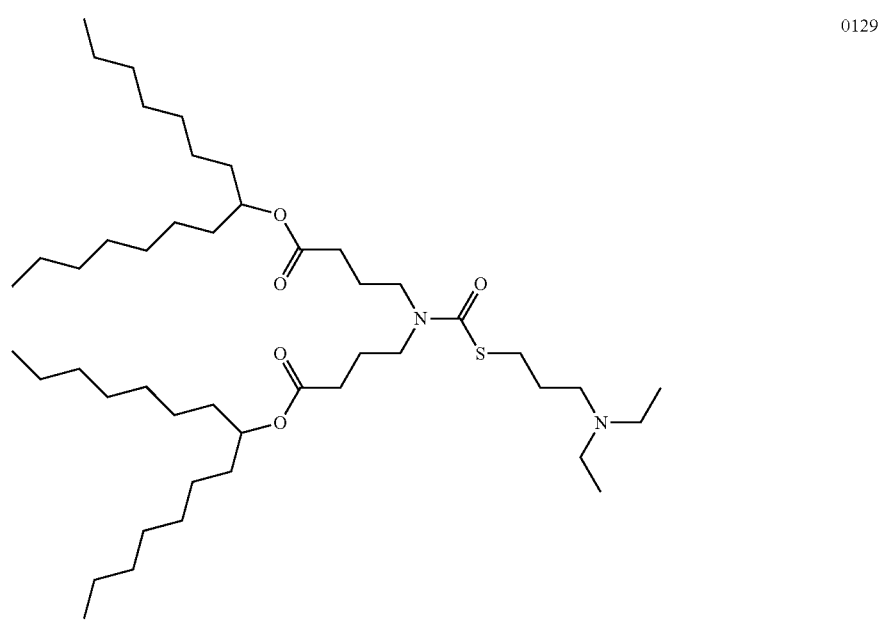 | 0129 |

TABLE 3-continued
| Compound | ATX-# |
|---|---|
| 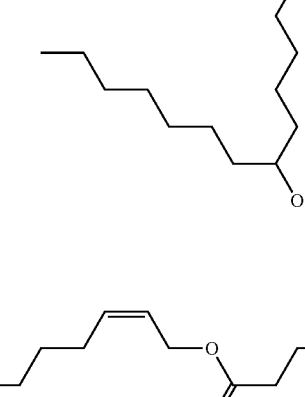 | 0082 |
| 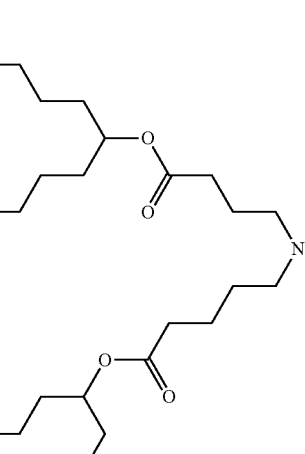 | 0085 |
| 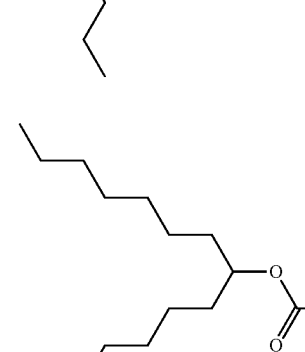 | 0083 |

TABLE 3-continued
| Compound | ATX-# |
|---|---|
| 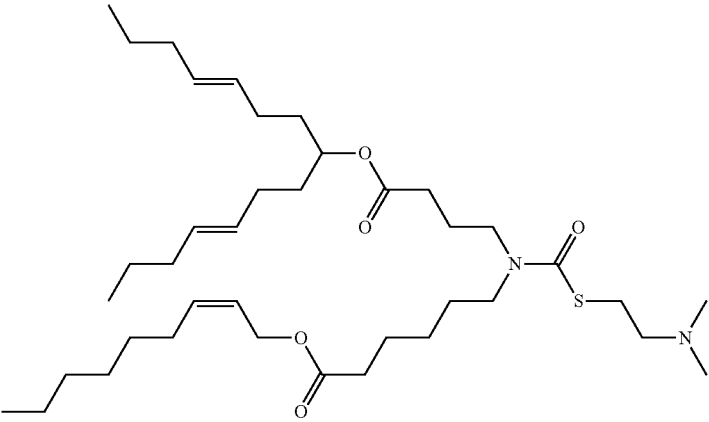 [SMILES: CCC/C=C/CCC(CC/C=C/CCC)OC(=O)CCCN(CCCCCC(=O)OC/C=C\CCCCCC)C(=O)SCCN(C)C] | 0121 |
| 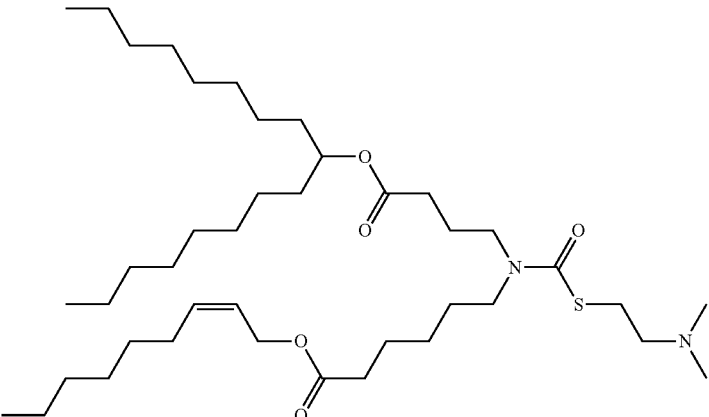 | 0091 |
| 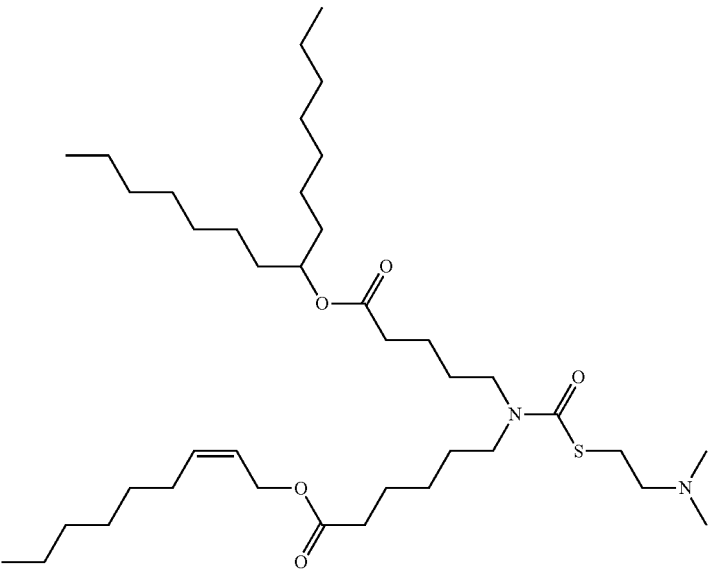 [SMILES: CCCCCC/C=C\COC(=O)CCCCCN(CCCCC(=O)OC(CCCCCCC)CCCCCCC)C(=O)SCCN(C)C] | 0102 |

TABLE 3-continued
| Compound | ATX-# |
|---|---|
| 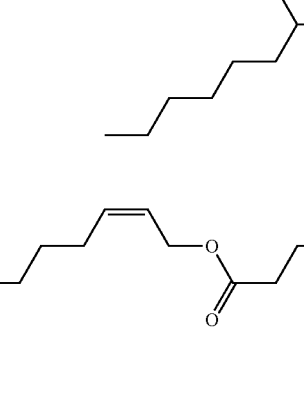 | 0098 |
| 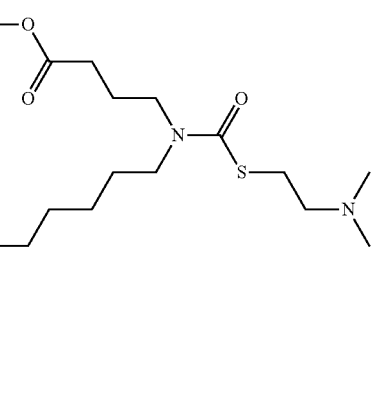 | 0092 |
| 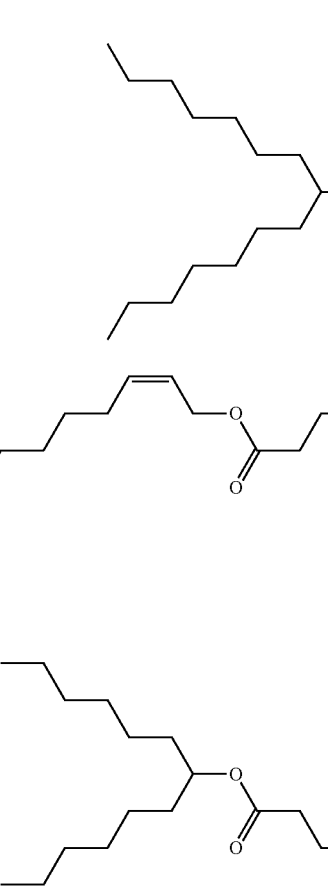 | 0084 |

TABLE 3-continued

| Compound | ATX-# |
|---|---|
| | 0095 |
| | 0125 |
| | 0094 |

TABLE 3-continued
| Compound | ATX-# |
|---|---|
| 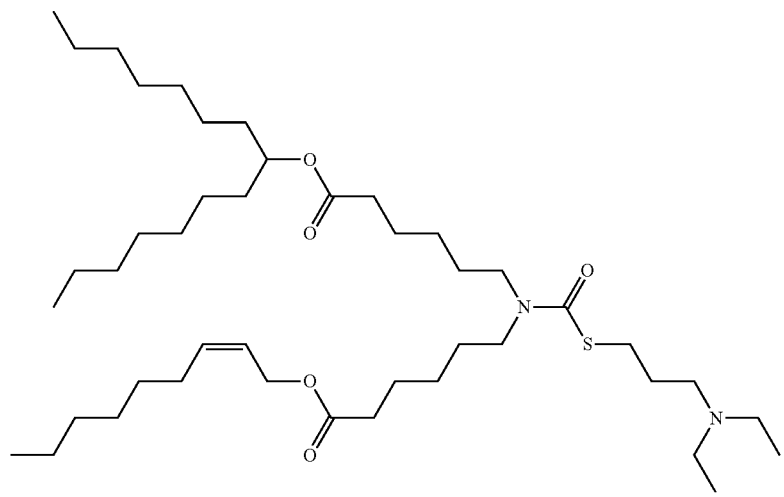 [SMILES: CCCCCC/C=C\COC(=O)CCCCCN(CCCCCC(=O)OC(CCCCCCC)CCCCCCC)C(=O)SCCCN(CC)CC] | 0109 |
| 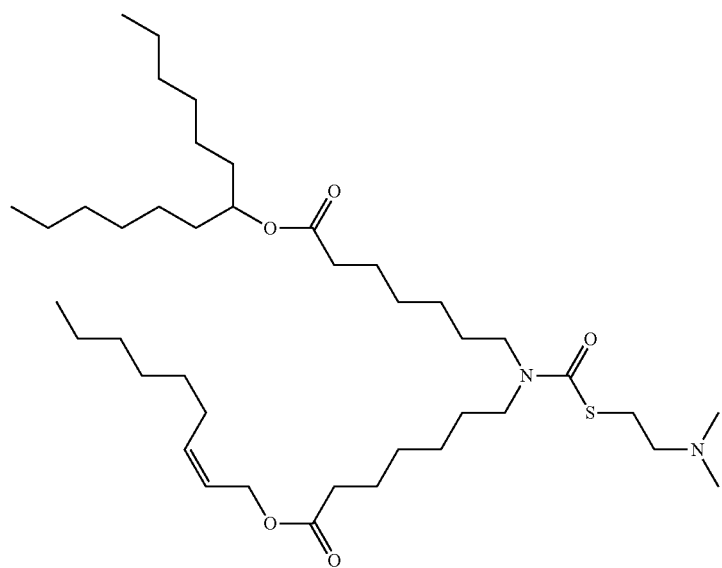 [SMILES: CCCCCC/C=C\COC(=O)CCCCCCN(CCCCCCC(=O)OC(CCCCCC)CCCCCC)C(=O)SCCN(C)C] | 0110 |

TABLE 3-continued
| Compound | ATX-# |
|---|---|
| 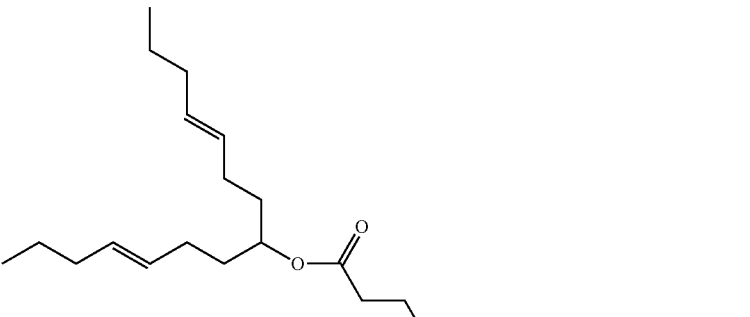 | 0118 |
| 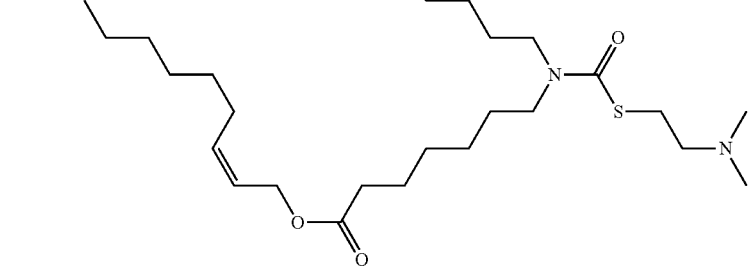 | 0108 |
| 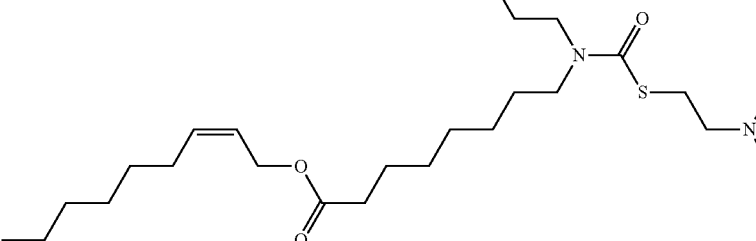 | 0107 |

TABLE 3-continued
| Compound | ATX-# |
|---|---|
| 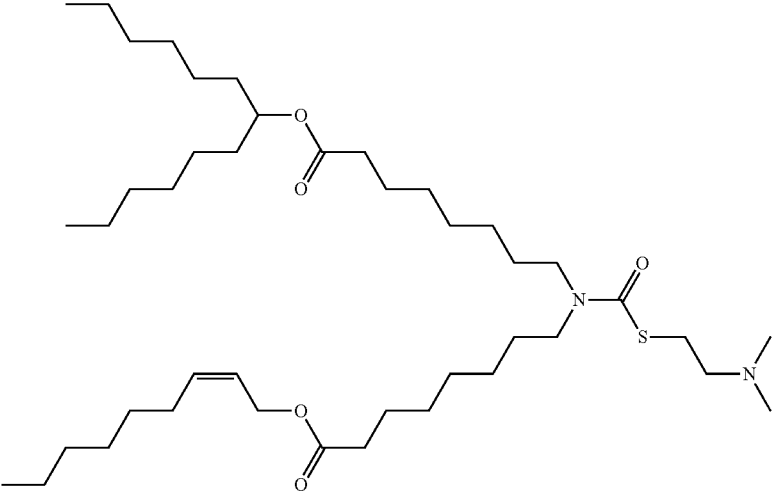 [SMILES: CCCCCC/C=C\COC(=O)CCCCCCCN(CCCCCCCC(=O)OC(CCCCCC)CCCCCC)C(=O)SCCN(C)C] | 0093 |
| 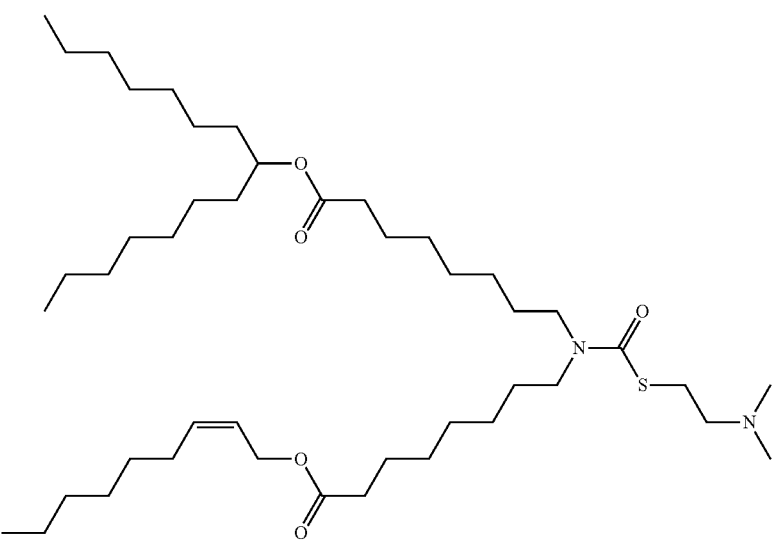 [SMILES: CCCCCC/C=C\COC(=O)CCCCCCCN(CCCCCCCC(=O)OC(CCCCCCC)CCCCCCC)C(=O)SCCN(C)C] | 0097 |
| 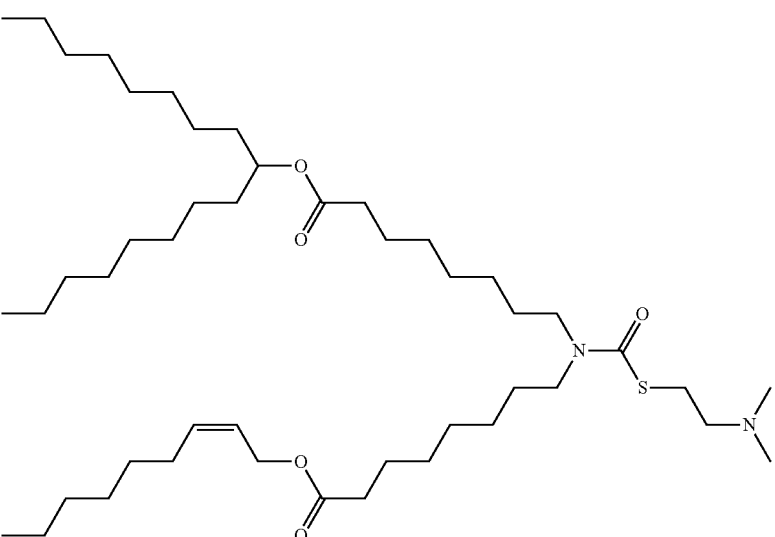 | 0096 |

TABLE 4
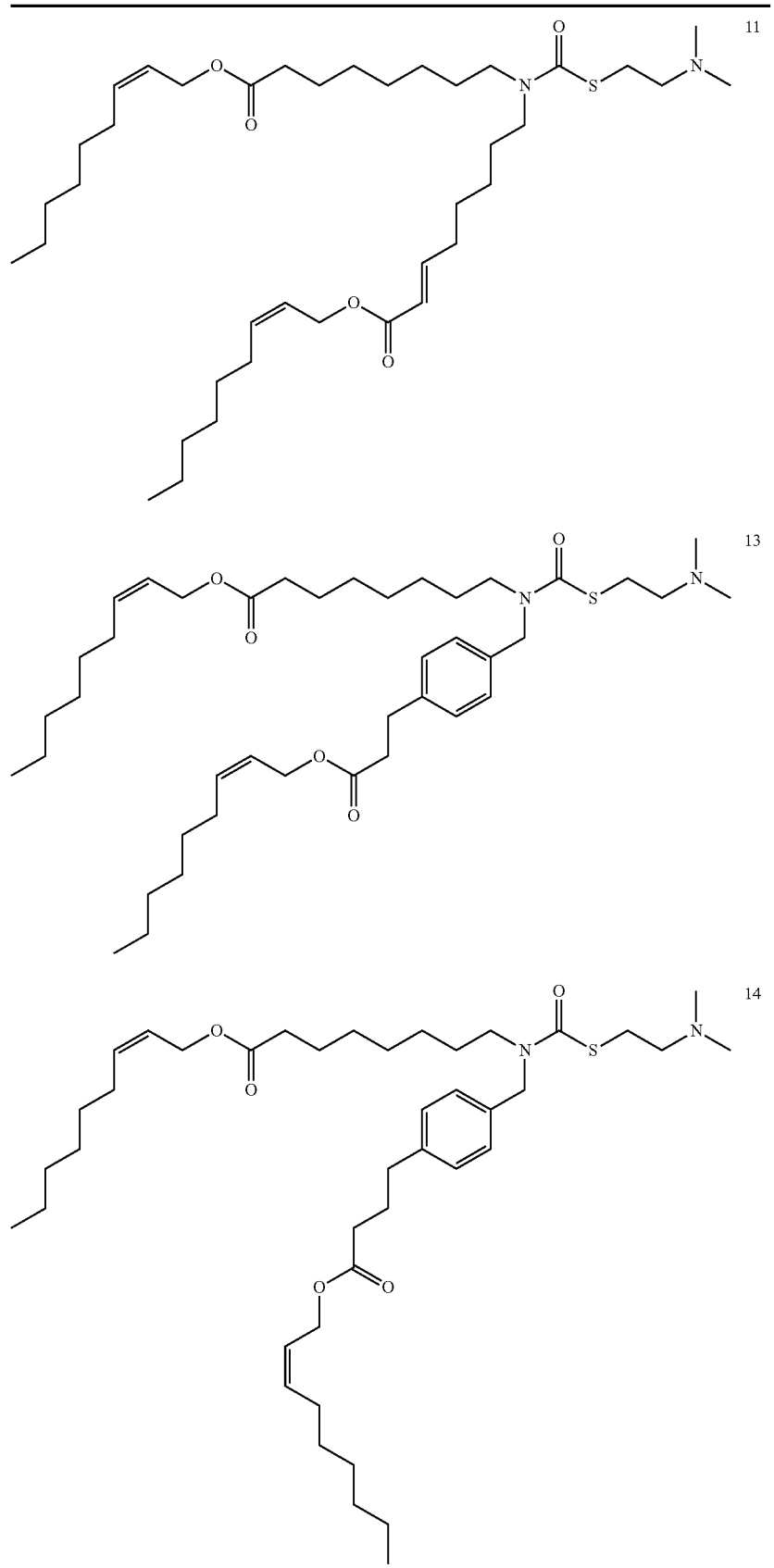

TABLE 4-continued
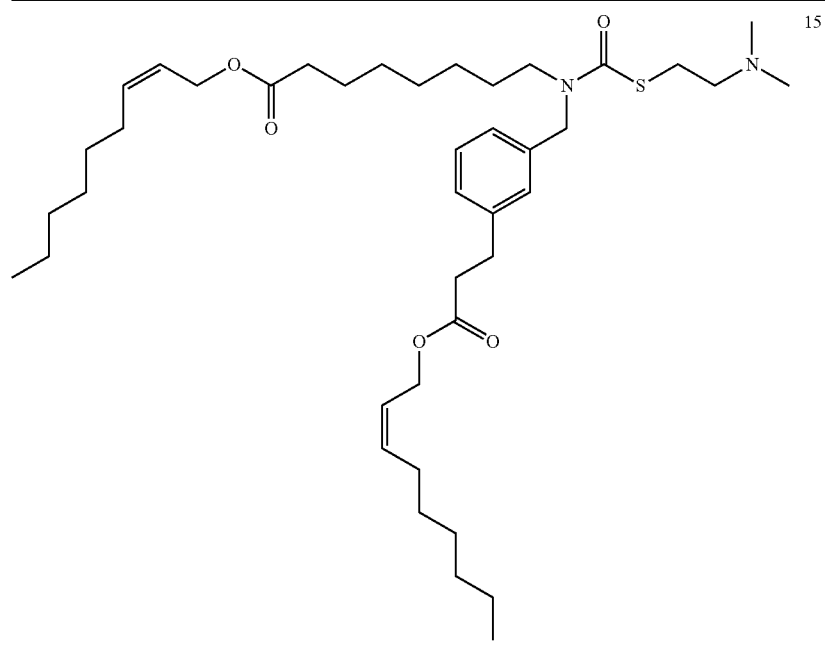
15
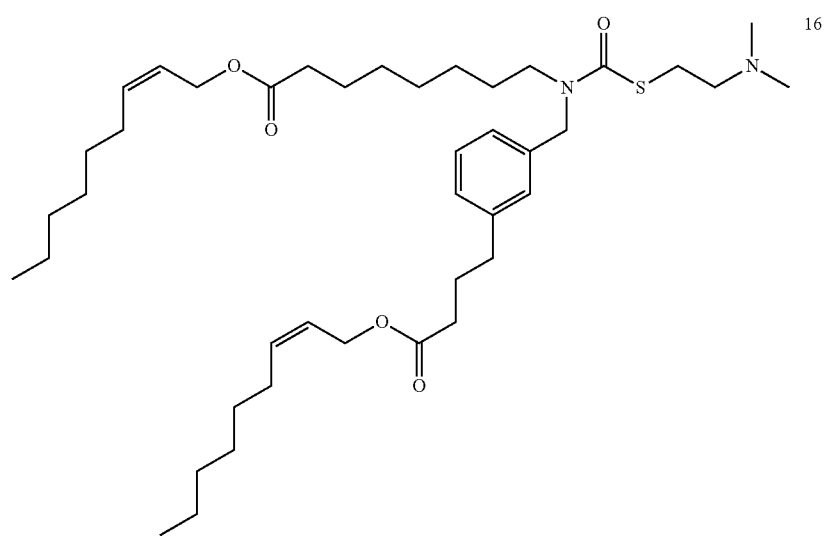
16
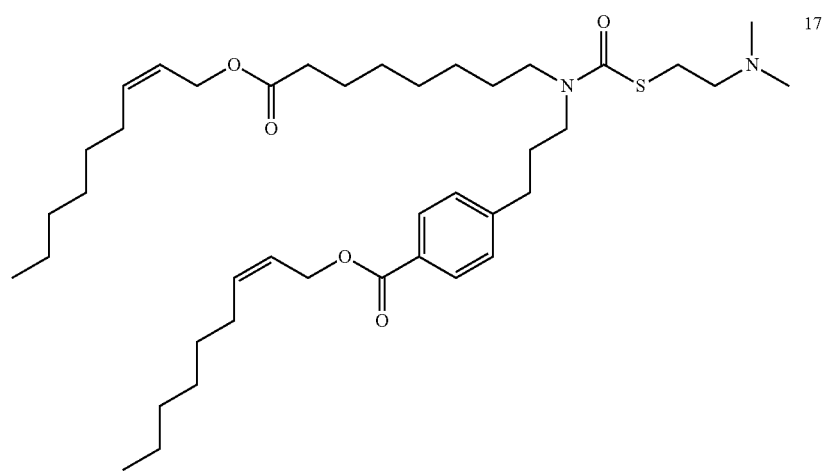
17

TABLE 4-continued
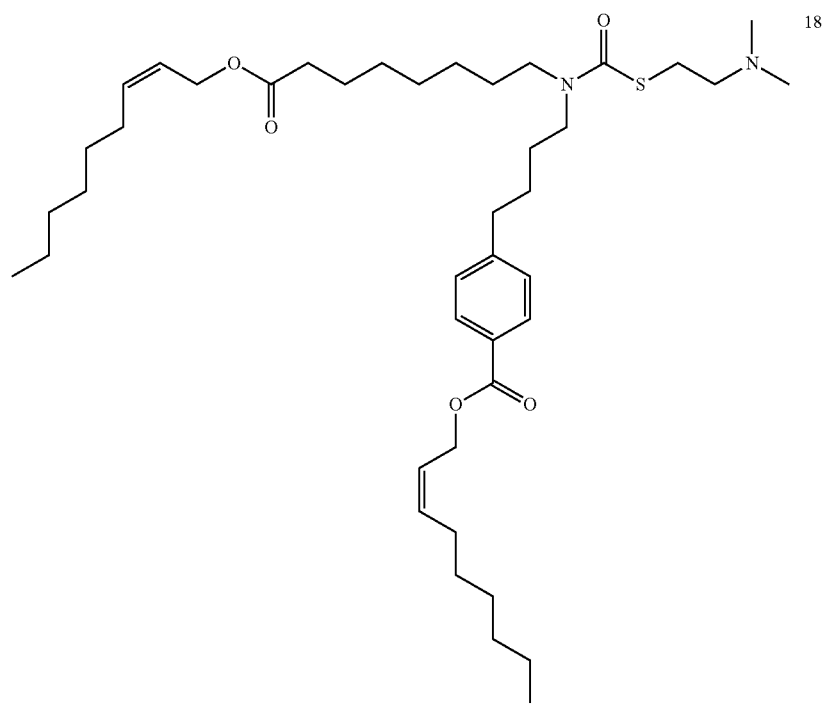
18
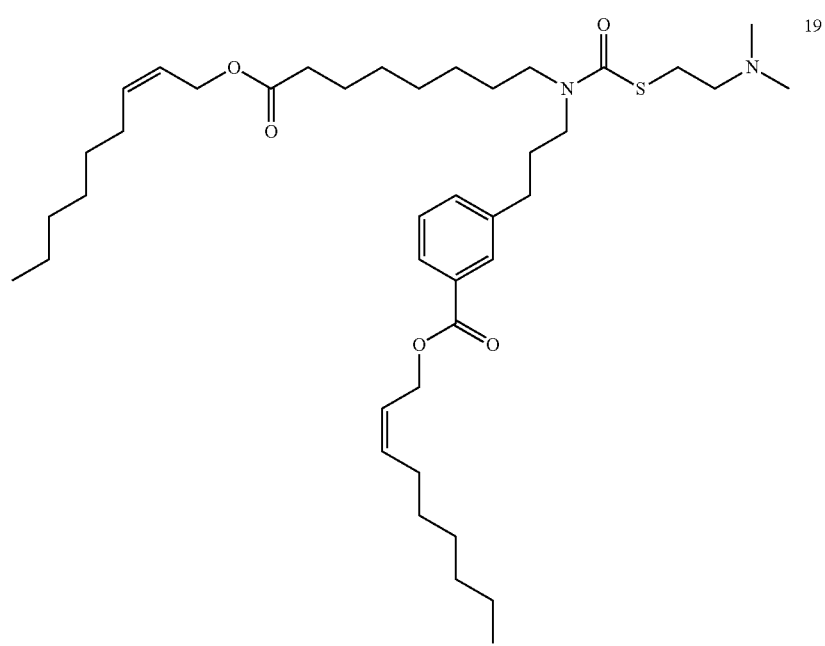
19

TABLE 4-continued

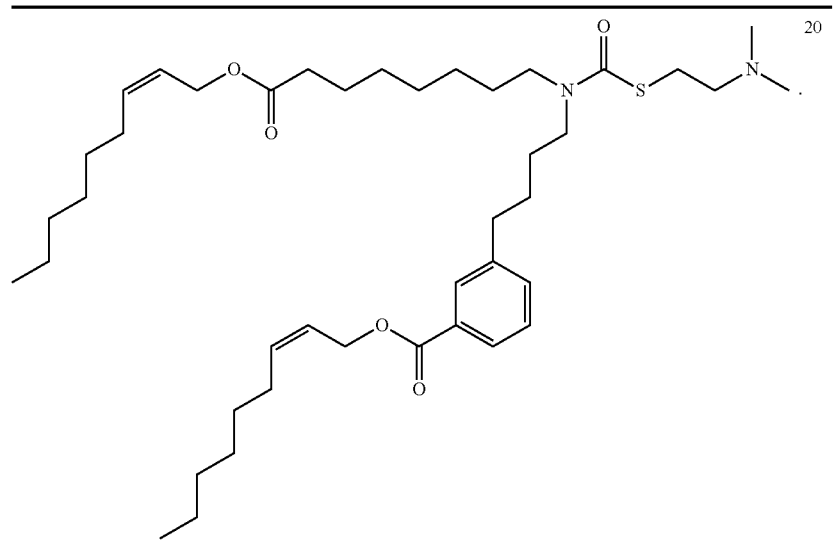

"Lipid-NA nanoparticle" is any lipid composition that can be used to deliver a compound including, but not limited to, liposomes, which comprise a lipid bilayer, either as unilamellar or multilamellar structure, in which the RNA is encapsulated at least in part by ionic pairing with cationic lipids.

"Lamellar morphology" refers to a bilayer structure. The lamellar morphology, bilayer structure of the lipid particles disclosed herein can be determined using analytical techniques, e.g., by cryo-TEM images.

"Lipid-encapsulated" can refer to a lipid formulation which provides a compound with full encapsulation, partial encapsulation, or both, in which RNA is not accessible to RNase-mediated hydrolysis or to intercalation of dyes.

Lipid-Encapsulated RNA Nanoparticle Formation

The method described herein provides an aqueous RNA solution comprising a therapeutic RNA or DNA (hereinafter NA), e.g., prepared under Good Manufacturing Practice (GMP), solubilized in an aqueous solution comprising a buffer, e.g., citrate. The present method also provides an organic solution comprising one or more lipids, e.g., clinical grade lipids synthesized under GMP, produced by solubilizing lipid in n water-miscible organic solvent. In the method described herein, the water-miscible organic solvent, preferably is a lower alkanol, e.g., ethanol. Preferably, both solutions are filter sterilized and their concentrations are adjusted.

The organic lipid solution is mixed with the aqueous solution comprising a nucleic acid to form a lipid-NA nanoparticle having a lamellar morphology, i.e., including a lipid bilayer. In one aspect, the nucleic acid is encapsulated in the lipid-NA nanoparticles with formation of the lamellar structure.

The method described herein is directed to continuously introducing a lipid solution into the aqueous solution in a mixing environment, preferably perpendicularly in a mixing module. The mixing dilutes the lipid solution with the aqueous solution to 20%, 22.5%, 25%, 27.5%, or 30% ethanol, preferably 25% ethanol, and causes formation of lipid-NA nanoparticles in a turbulent flow.

After formation of the lipid-NA nanoparticles, the mixture is continuously diluted by a buffer to 7.5%, 10%, 12.5%, or 15%, preferably to less than 12.5% ethanol, which further stabilizes the lipid-NA nanoparticles and increases encapsulation of nucleic acid.

The lipid-NA nanoparticles are concentrated by tangential flow filtration, preferably by hollow fiber filters. The concentrated lipid-NA nanoparticles are subjected to an ultrafiltration step to remove the alkanol and substitute the buffer. The nucleic acid concentration is adjusted by dilution. The resulting formulation is filter sterilized, and filled in vials. The process will now be discussed in more detail herein below using the steps as set forth in FIG. 1.

Lipid Solubilization and NA Dissolution

In one embodiment, the lipid-NA nanoparticles produced by the method described herein are in the form of multimolecular assemblies of NA and lipids, in which the NA is encapsulated at least in part by ionic pairing with cationic lipids.

The preferred size for lipid-NAnoparticles comprising siNA made by the method described herein are about 50-200 nm in diameter, preferably, with a size distribution in which the mean size (e.g., diameter) is about 70 nm to about 150 nm, and more preferably the mean size is less than about 100 nm.

In certain aspects, the lipid-NA nanoparticles of the description herein include four lipid components: a phospholipid; cholesterol; a PEG-lipid; and a cationic lipid. Preferably, the phospholipid is DSPC, the PEG-lipid is PEG-DMG and the cationic lipid is ATX-002. Most preferably, the molar composition is about 58:7:33.5:1.5 or 50:7:40:3, ATX:DSPC:Cholesterol:PEG-DMG. In certain embodiments, the organic solvent concentration wherein the lipids are solubilized is about 45% v/v to about 90% v/v. In certain preferred aspects, the organic solvent is a lower alkanol. Suitable lower alkanols include, e.g., methanol, ethanol, propanol, butanol, pentanol, their isomers and combinations thereof. The solvent is preferably ethanol with a volume of about 50-90% v/v. Preferably, the lipids occupy a volume of about 1 mL/g to about 5 mL/g.

The lipids are solubilized using for example, an overhead stirrer at a suitable temperature. In one aspect, the total lipid concentration of the solution is about 49.4 mg/mL. In certain preferred aspects, the NA is included in an aqueous solution (e.g., buffer) and is diluted to a final concentration. Preferably, the final concentration is about 0.55 mg/mL in citrate buffer, with a pH of about 3.5.

The RNA is preferably a double-stranded RNA (dsRNA) or a mRNA. The size of the dsRNA is between 10 base pairs to several hundred bases, preferably less than 30 base pairs, most preferably less than 25 base pairs. The size of the mRNA is between 10 and several thousand bases in a single strand.

Lipid-NA Nanoparticle Formation

After the organic solution and the aqueous solutions are prepared, they are mixed together using the apparatus described in detail below. Briefly, the apparatus consists of a first tube for transporting the aqueous NA solution and a second tube for transporting the organic lipid solution, in which the second tube intersects the first tube perpendicularly within the mixing module. The two solutions are pumped through the respective tubes by separate HPLC pumps and mix in the region of the first tube perpendicularly within the mixing module. Preferably, the aqueous NA solution is pumped at a rate 2.0-, 2.5-, 3.0-, 3.25-, or 3.5-fold, preferably 3.0-fold, greater than the organic lipid solution. Upon mixing the two solutions in the mixing area, lipid-NA nanoparticles are formed.

The pump speeds and the size of the first tube in the region of the mixing module provides for a mixing process that involves turbulent flow. The processes described herein for mixing of the lipid solution and the aqueous solution provides for encapsulation of NA in the lipid-NA nanoparticles formed coincident with their formation with an encapsulation efficiency of greater than 95%.

Lipid-NA nanoparticles are typically formed at room temperature, but lipid-NA nanoparticles may be formed at elevated temperatures according to the present invention. There are no general requirements for buffer composition. In fact, the processes and apparatus of the present invention can formulate a lipid vesicle by mixing lipid in ethanol with NA in an aqueous solution.

In one embodiment, lipid-NA nanoparticles form when lipids dissolved in an organic solvent, e.g., ethanol, are diluted in a stepwise manner by mixing with a buffered aqueous solution, first by mixing the aqueous and lipid streams together in the mixing module to a final concentration of organic solvent preferably between 25-40%. The resultant lipid, solvent and solute concentrations can be kept constant throughout the vesicle formation process. Following the initial formation, the initial lipid-NA mixture is further diluted by addition of buffer, preferably to about 6.0%, 6.25%, 7.0% 7.5%, 10%, 12.5%, or 15% organic solvent, most preferably 6.25% 6.25%, 7.0% 7.5%, 10%, or 12.5%.

The continuous process described herein is fully scalable. In one aspect, lipid-NA nanoparticles are formed having a mean diameter of less than about 80 nm, without mechanical-energy processes such as membrane extrusion, sonication or microfluidization.

Lipid-NA Nanoparticles

The lipid-NA nanoparticles disclosed herein comprise a nanoparticle or a bilayer of lipid molecules. In addition to the cationic lipids and ionizable cationic lipids, the lipid-NA nanoparticle comprises a neutral lipid or a polymer.

In some embodiments, the NA is fully encapsulated within the lipid portion of the lipid-NA nanoparticle such that the NA in the lipid-NA nanoparticles is resistant in aqueous solution to nuclease degradation. In other embodiments, the lipid-NA nanoparticles described herein are substantially non-toxic to mammals such as humans. The lipid-NA nanoparticles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid-NA nanoparticles described herein also typically have a lipid:NA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1.

In preferred embodiments, the lipid particles comprise a NA, a cationic lipid (e.g., one or more cationic lipids or salts thereof described herein), a phospholipid, and a conjugated lipid that inhibits aggregation of the particles (e.g., one or more PEG-lipid conjugates). The lipid-NA nanoparticles can also include cholesterol. The lipid-NA nanoparticles may comprise at least 1, 2, 3, 4, 5, 6, 7, 8, 9, 10, or more different NA that express one or more polypeptides.

In the lipid-NA nanoparticles the NA may be fully encapsulated within the lipid portion of the particle, thereby protecting the NA from nuclease degradation. In preferred embodiments, the lipid-NA nanoparticles comprise a NA that is fully encapsulated within the lipid portion of the particle, thereby protecting the NA from nuclease degradation. In certain instances, the NA in the lipid particle is not substantially degraded after exposure of the particle to a nuclease at 37° C. for at least 20, 30, 45, or 60 minutes. In certain other instances, the NA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the NA is complexed with the cationic lipid of the lipid-NA nanoparticles. One of the benefits of the formulations of the present invention is that the lipid-NA nanoparticles are substantially non-toxic to mammals such as humans.

"Fully encapsulated" means that the NA in the nucleic acid-lipid particle is not significantly degraded after exposure to serum or a nuclease assay that would significantly degrade free NA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present invention provides a nucleic acid-lipid particle composition comprising a plurality of nucleic acid-lipid particles.

The lipid particle comprises NA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the NA encapsulated therein.

Depending on the intended use of the lipid-NA nanoparticles, the proportions of the components can be varied and the delivery efficiency of a particular formulation can be measured using assays know in the art.

Cationic Lipids

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, or drugs, to a patient, tissue, organ, or cell. These novel compounds may also be used as materials for coating, additives, excipients, materials, or bioengineering.

The cationic lipid compounds of the lipid-NA nanoparticles provide for several different uses in the drug delivery art. The amine-containing portion of the cationic lipid compounds may be used to complex NA, thereby enhancing the delivery of NA and preventing their degradation. The cationic lipid compounds may also be used in the formation of lipid-NA nanoparticles containing the agent to be delivered. Preferably, the cationic lipid compounds are biocompatible and biodegradable, and the formed lipid-NA nanoparticles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have a $pK_a$ in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with NA, for buffering the pH, for causing endo-osmolysis, for protecting the agent to be delivered, they can be synthesized from commercially available starting materials; and/or they are pH responsive and can be engineered with a desired $pK_a$.

Neutral Helper Lipids

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the non-cationic lipid present in lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the non-cationic lipid comprises from 10 mol % to 60 mol %, from 20 mol % to 55 mol %, from 20 mol % to 45 mol %, 20 mol % to 40 mol %, from 25 mol % to 50 mol %, from 25 mol % to 45 mol %, from 30 mol % to 50 mol %, from 30 mol % to 45 mol %, from 30 mol % to 40 mol %, from 35 mol % to 45 mol %, from 37 mol % to 42 mol %, or 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, the phospholipid component in the mixture may comprise from 2 mol % to 20 mol %, from 2 mol % to 15 mol %, from 2 mol % to 12 mol %, from 4 mol % to 15 mol %, or from 4 mol % to 10 mol % (or any fraction thereof or range therein) of the total lipid present in the particle. In certain preferred embodiments, the phospholipid component in the mixture comprises from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

In other embodiments, the cholesterol component in the mixture may comprise from 25 mol % to 45 mol %, from 25 mol % to 40 mol %, from 30 mol % to 45 mol %, from 30 mol % to 40 mol %, from 27 mol % to 37 mol %, from 25 mol % to 30 mol %, or from 35 mol % to 40 mol % (or any fraction thereof or range therein) of the total lipid present in the particle. In certain preferred embodiments, the cholesterol component in the mixture comprises from 25 mol % to 35 mol %, from 27 mol % to 35 mol %, from 29 mol % to 35 mol %, from 30 mol % to 35 mol %, from 30 mol % to 34 mol %, from 31 mol % to 33 mol %, or 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from 25 mol % to 45 mol %, from 25 mol % to 40 mol %, from 30 mol % to 45 mol %, from 30 mol % to 40 mol %, from 31 mol % to 39 mol %, from 32 mol % to 38 mol %, from 33 mol % to 37 mol %, from 35 mol % to 45 mol %, from 30 mol % to 35 mol %, from 35 mol % to 40 mol %, or 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle.

In other embodiments, the non-cationic lipid comprises from 5 mol % to 90 mol %, from 10 mol % to 85 mol %, from 20 mol % to 80 mol %, 10 mol % (e.g., phospholipid only), or 60 mol % (e.g., phospholipid and cholesterol or derivative thereof) (or any fraction thereof or range therein) of the total lipid present in the particle.

The percentage of non-cationic lipid present in the lipid particles is a target amount, and that the actual amount of non-cationic lipid present in the formulation may vary, for example, by +5 mol %.

A composition containing a cationic lipid compound may be 30, 35, 40, 45, 50, 55, 60, 65, 70, or 70 wt % cationic lipid compound, 0, 5, 10, 15, 20, 25, 30, 35, 40, 45, 50, 55, or 60 wt % cholesterol, 0, 5, 10, 15, 20, 25, or 30 wt % phospholipid and 1-10% polyethylene glycol (PEG). Preferably, the composition is 30, 32, 34, 36, 36, 38 or 40 wt % cationic lipid compound, 40, 42, 44, 46, 48 or 50 wt % cholesterol, and 10, 11, 12, 13, 14, 15, 16, 17, 18, 19 or 20 wt % PEG-lipid. In other preferred embodiments, the composition is 50, 55, 60, 65, 70 or 75 wt % cationic lipid compound, 20, 22, 24, 26, 28, 30, 32, 34, 36, 38 or 40 wt % cholesterol, and 5, 6, 7, 8, 9, or 10 wt % phospholipid, and 1, 2, 3, 4, 5, 6, 7 8, 9, or 10 wt % PEG-lipid. The composition may contain 60, 62, 64, 66, 68, or 70 wt % cationic lipid compound, 25, 26, 27, 28, 29, 30, 31, 32, 33, 34, or 35 wt % cholesterol, and 5, 6, 7, 8, 9, or 10 wt % PEG-lipid. The composition may contain up to 5, 10, 15, 20, 25, 30, 40, 50, 60, 70, 80, or 90 wt % cationic lipid compound and 1, 2, 3, 4, 5, 6, 7, 8, 9, 10, 11, 12, 13, 14, 15, 20, 25, 30, 35, 40, 45, 50, 55, 60, 65, 70, or 75 wt % ionizable cationic lipid.

The formulation may be a lipid particle formulation, for example containing 8-30% compound, 5, 10, 15, 20, 25, 30, 35, 40, 45, 50, 55, 60, 65, 70, or 75 wt % ionizable cationic lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

In addition to cationic, the lipid particles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

In a preferred embodiment, the lipid conjugate is a PEG-lipid. PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$). Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to glycerides forming a glycol, e.g., 1,2-dimyristoyl-sn-glycerol, methoxy-PEG glycol (PEG-DMG), PEG conjugated to ceramides, PEG conjugated to cholesterol, or a derivative thereof, and mixtures thereof.

The PEG moiety of the PEG-lipid conjugates described herein may comprise an average molecular weight ranging from 550 Daltons to 10,000 Daltons. In certain instances, the PEG moiety has an average molecular weight of from 750 Daltons to 5,000 Daltons (e.g., from 1,000 Daltons to 5,000 Daltons, from 1,500 Daltons to 3,000 Daltons, from 750 Daltons to 3,000 Daltons, from 750 Daltons to 2,000 Daltons). In preferred embodiments, the PEG moiety has an average molecular weight of 2,000 Daltons or 750 Daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

The term "diacylglycerol" or "DAG" includes a compound having 2 fatty acyl chains, R' and R$_2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl).

The term "dialkyloxyalkyl" or "DAA" includes a compound having 2 alkyl chains, R and R', both of which have independently between 2 and 30 carbons. The alkyl groups can be saturated or have varying degrees of unsaturation.

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of 750 or 2,000 Daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from 0.1 mol % to 2 mol %, from 0.5 mol % to 2 mol %, from 1 mol % to 2 mol %, from 0.6 mol % to 1.9 mol %, from 0.7 mol % to 1.8 mol %, from 0.8 mol % to 1.7 mol %, from 0.9 mol % to 1.6 mol %, from 0.9 mol % to 1.8 mol %, from 1 mol % to 1.8 mol %, from 1 mol % to 1.7 mol %, from 1.2 mol % to 1.8 mol %, from 1.2 mol % to 1.7 mol %, from 1.3 mol % to 1.6 mol %, or from 1.4 mol % to 1.5 mol % (or any fraction thereof or range therein) of the total lipid present in the particle. In other embodiments, the lipid conjugate (e.g., PEG-lipid) comprises from 0 mol % to 20 mol %, from 0.5 mol % to 20 mol %, from 2 mol % to 20 mol %, from 1.5 mol % to 18 mol %, from 2 mol % to 15 mol %, from 4 mol % to 15 mol %, from 2 mol % to 12 mol %, from 5 mol % to 12 mol %, or 2 mol % (or any fraction thereof or range therein) of the total lipid present in the particle.

In further embodiments, the lipid conjugate (e.g., PEG-lipid) comprises from 4 mol % to 10 mol %, from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

The percentage of lipid conjugate (e.g., PEG-lipid) present in the lipid particles of the invention is a target amount, and the actual amount of lipid conjugate present in the formulation may vary, for example, by ±2 mol %. One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. In addition, other variables including, e.g., pH, temperature, or ionic strength, can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Lipid-NA Nanoparticle Vaccine

The lipid-NA nanoparticle includes the use of any type of expression vector, such as a viral expression vector, e.g., poxvirus (e.g., orthopoxvirus or avipoxvirus such as vaccinia vims, including Modified Vaccinia Ankara or MVA, MVA-BN, NYVAC according to WO-A-92/15672, fowipox, e.g., TROVAX, canarypox, e.g., ALVAC (WO-A-95/27780 and WO-A-92/15672) pigeonpox, swinepox and the like), adenovirus, AAV herpesvirus, and lentivirus; or a plasmid or DNA or nucleic acid molecule vector. Some vectors that are cytoplasmic, such as poxvirus vectors, may be advantageous. However, adenovirus, AAV and lentivirus can also be advantageous to use in the practice of the invention.

In a ready-for-use, especially reconstituted, vaccine or immunogenic composition, the vector, e.g., viral vector, is present in the quantities within the ambit of the skilled person from this disclosure and the knowledge in the art (such as in patent and scientific literature cited herein).

Whole antigen or vector, e.g., recombinant live vaccines generally exist in a freeze-dried form allowing their storage and are reconstituted immediately before use in a solvent or excipient, which can include an adjuvant as herein discussed.

A vaccination or immunization set or kit comprising, packaged separately, freeze-dried vaccine comprising a lipid-NA nanoparticle and a solution, advantageously including an adjuvant compound as herein discussed for the reconstitution of the freeze-dried vaccine.

A method of vaccination or immunization comprising or consisting essentially of or consisting of administering, e.g., by the parenteral, preferably subcutaneous, intramuscular or intradermal, route or by the mucosal route a vaccine or immunogenic composition comprising a lipid-NA nanoparticle at the rate of one or more administrations. Optionally this method includes a preliminary step of reconstituting the freeze-dried vaccine or immunogenic composition comprising a lipid-NA nanoparticle (e.g., if lyophilized whole antigen or vector) in a solution, advantageously also including an adjuvant.

The pharmaceutical compositions comprising lipid-NA nanoparticle for therapeutic treatment are intended preferably administered subcutaneously, intradermally, or intramuscularly. The invention provides compositions for administration that comprise a solution of the lipid-NA nanoparticle suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, e.g., sodium acetate, sodium lactate, sodium chloride, potassium chloride, calcium chloride, sorbitan monolaurate, or triethanolamine olcate.

Pharmaceutical Compositions

Lipid-NA nanoparticles described herein are useful as components in pharmaceutical compositions. These compositions will typically include a pharmaceutically acceptable carrier in addition to the liposomes. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of a lipid-NA nanoparticle or component thereof as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluene sulfonic, methane sulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenlyiacetic, alkanoic such as acetic, $HOOC—(CH2)_n—COOH$ where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Pharmaceutical compositions described herein may include the lipid-NA nanoparticles in plain water (e.g., w.f.i.) or in a buffer, e.g., a phosphate buffer, a Tris buffer, a borate buffer, a succinate buffer, a histidine buffer, or a citrate buffer. Buffer salts will typically be included in the 5-20 mM range.

Pharmaceutical compositions as described herein may have a pH between 5.0 and 9.5 e.g., between 6.0 and 8.0.

Pharmaceutical compositions as described herein may include sodium salts (e.g., sodium chloride) to give tonicity. A concentration of 10±2 mg/ml NaCl, e.g., about 9 mg/ml.

Pharmaceutical compositions as described herein may include metal ion chelators. These can prolong NA stability by removing ions which can accelerate phosphodiester hydrolysis, e.g., one or more of EDTA, EGTA, BAPTA, or pentetic acid. Such chelators are preferably at between 10-500 µM, e.g., 0.1 mM. A citrate salt, such as sodium citrate, can also act as a chelator, while advantageously also providing buffering activity.

Pharmaceutical compositions as described herein preferably have an osmolality of between 200 mOsm/kg and 400 mOsm/kg, e.g., between 240-360 mOsm/kg, or between 290-310 mOsm/kg.

Pharmaceutical compositions as described herein preferably includes one or more preservatives, such as thiomersal or 2-phenoxyethanol. Mercury-free compositions are most preferred.

Pharmaceutical compositions as described herein are preferably sterile.

Pharmaceutical compositions as described herein are preferably non-pyrogenic e.g., containing <1 EU (endotoxin unit, a standard measure) per dose, and preferably <0.1 EU per dose.

Pharmaceutical compositions as described herein are preferably gluten free.

Pharmaceutical compositions as described herein may be prepared in unit dose form. In some embodiments a unit dose may have a volume of between 0.1-1.0 ml e.g., about 0.5 ml.

The compositions may be prepared as injectables, either as solutions or suspensions. The composition may be prepared for pulmonary administration e.g., by an inhaler, using a fine spray. The composition may be prepared for nasal, aural or ocular administration e.g., as spray or drops.

Pharmaceutical compositions comprise an immunologically effective amount of lipid-NA nanoparticles, as well as any other components, as needed.

Pharmaceutical compositions as described herein are also suitable for a delivery device, e.g., syringe, nebulizer, sprayer, inhaler, or dermal patch, which can be used to administer the composition to a vertebrate subject.

Lipid-NA nanoparticles as described herein do not contain ribosomes.

EXAMPLES

Example 1 Lipid-NA Nanoparticle RNA Production Process

Lipid-NA nanoparticle mRNA formulations were prepared by mixing lipids in ethanol with mRNA dissolved in 5 mM citrate, pH 3.5. Constituent lipids in the formulation are ATX:DSPC:cholesterol:PEG-DMG at molar percentages of 50:7:40:3). The ethanolic solution containing lipids was mixed with the buffer stream containing mRNA at a flow rate ratio of 1:3 (ethanol:buffer) using a microfluidic device (Precision NanoSystems Inc., Vancouver, Canada). The flow rate of the lipid stream was 3 mL/min, and the mRNA stream was 9 ml/min. The total combined flow rate was 12 mL/min. Ethanol concentration in the lipid/RNA mix is 25% (v/v). The mixed material is instantaneously diluted with 2 volumes of 50 mM phosphate, pH 6.0, to reduce ethanol concentration to 8.3%. Diluted formulations were dialyzed against 50 mM phosphate, pH 6.0, for 12-16 h using cellulose dialysis membranes (100 Kd MWCO) and secondary dialysis was performed against 50 mM HEPES, 50 mM NaCl, 9% sucrose, pH 7.4, for 3-5 h. Dialyzed formulations were concentrated using AMICON® ULTRA CENTRIFUGAL filters (MilliporeSigma). The mRNA concentration in the formulation was measured by RIBOGREEN™ assay and the concentration was adjusted to 0.2 mg/mL by diluting with 50 mM HEPES, 50 mM NaCl, 9% sucrose, pH 7.3 containing glycerol such that the final concentration of glycerol in the formulation is 5%. The diluted formulation is then filtered through a 0.2 µm filter and aseptically filled into glass vials, stoppered, capped and placed at −70±5° C.

The formulation is characterized for its lipid content by HPLC, % encapsulation and mRNA concentration by RIBOGREEN™ assay, particle size by dynamic light scattering on a Malvern ZETASIZER NANO ZS, PH, OSMOLALITY.

Figure 12:
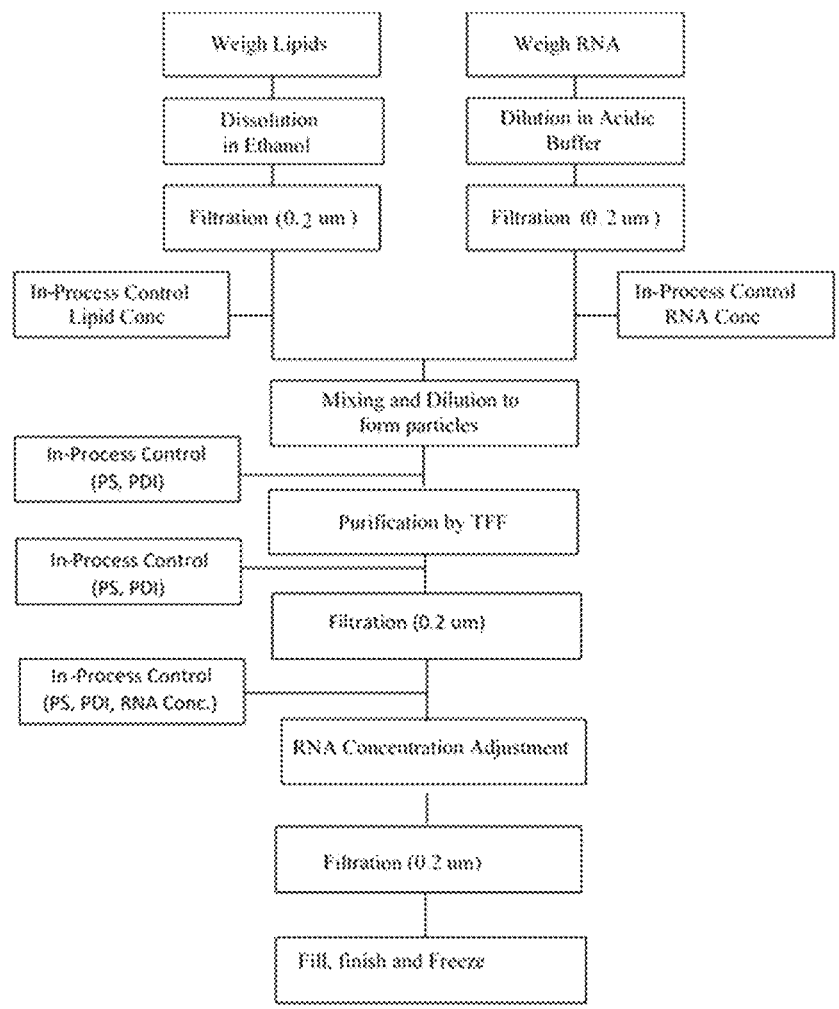
FIG. 12 shows a process of producing lipid-encapsulated RNA nanoparticles.

Lipid-NA nanoparticles were also prepared according to the method of the representative flow chart according to FIG. 12 showing steps of the process of producing lipid-encapsulated RNA nanoparticles.

The geometry of the mixing layer consists of a first tube for transporting the aqueous solution having an inner diameter (ID) of greater than 0.1", preferably an ID greater than 0.132"; and a second tube for transporting the ethanol solution consisting of a ID greater than 0.005", preferably greater than 0.01"; in which the second (organic) tube intersects the first (aqueous) tube at or near a perpendicular angle. The combined flow rate during mixing is at least 200 ml/min, preferably at least 300 min.

The method described herein provides an aqueous RNA solution comprising a therapeutic RNA, e.g., prepared under Good Manufacturing Practice (GMP), solubilized in an aqueous solution comprising a buffer, e.g., citrate. The present method also provides an organic solution comprising one or more lipids, e.g., clinical grade lipids synthesized under GMP, produced by solubilizing lipid in n water-miscible organic solvent. In the method described herein, the water-miscible organic solvent, preferably is a lower alkanol, e.g., ethanol. Preferably, both solutions are filter sterilized and their concentrations are adjusted.

The organic lipid solution is mixed with the aqueous solution comprising a nucleic acid to form a lipid-encapsulated RNA nanoparticle having a lamellar morphology, i.e., including a lipid bilayer. In one aspect, the nucleic acid is encapsulated in the lipid-encapsulated RNA nanoparticles with formation of the lamellar structure.

The method described herein is directed to continuously introducing a lipid solution into the aqueous solution in a mixing environment, preferably perpendicularly in a mixing module. The mixing dilutes the lipid solution with the aqueous solution to 20%, 22.5%, 25%, 27.5%, or 30% ethanol, preferably 25% ethanol, and causes formation of lipid-encapsulated RNA nanoparticles in a turbulent flow.

After formation of the lipid-encapsulated RNA nanoparticles, the mixture is continuously diluted by a buffer to 7.5%, 10%, 12.5%, or 15%, preferably to less than 12.5% ethanol, which further stabilizes the lipid-encapsulated RNA nanoparticles and increases encapsulation of nucleic acid.

The lipid-encapsulated RNA nanoparticles are concentrated by tangential flow filtration, preferably by hollow fiber filters. The concentrated lipid-encapsulated RNA nanoparticles are subjected to an ultrafiltration step to remove the alkanol and substitute the buffer. The nucleic acid concentration is adjusted by dilution. The resulting formulation is filter sterilized, and filled in vials. The process will now be discussed in more detail herein below using the steps as set forth in the flow chart above.

Lipid Solubilization and RNA Dissolution

In one embodiment, the lipid-encapsulated RNA nanoparticles produced by the method described herein are in the form of multimolecular assemblies of RNA and lipids, in which the RNA is encapsulated at least in part by ionic pairing with cationic lipids.

The preferred size for lipid-encapsulated nanoparticles comprising siRNA made by the method described herein are about 50-200 nm in diameter, preferably, with a size distribution in which the mean size (e.g., diameter) is about 70 nm to about 150 nm, and more preferably the mean size is less than about 100 nm.

In certain aspects, the lipid nanoparticles of the description herein include four lipid components: a phospholipid; cholesterol; a PEG-lipid; and an ionizable cationic lipid. Preferably, the phospholipid is DSPC, the PEG-lipid is PEG-DMG and the ionizable cationic lipid is an ATX lipid. Most preferably, the molar composition is about 58:7:33.5:1.5 or 50:7:40:3, ATX:DSPC:Cholesterol:PEG-DMG. In certain embodiments, the organic solvent concentration wherein the lipids are solubilized is about 45% v/v to about 90% v/v. In certain preferred aspects, the organic solvent is a lower alkanol. Suitable lower alkanols include, e.g., methanol, ethanol, propanol, butanol, pentanol, their isomers and combinations thereof. The solvent is preferably ethanol with a volume of about 50-90% v/v. Preferably, the lipids occupy a volume of about 1 mL/g to about 5 mL/g.

The lipids are solubilized using for example, an overhead stirrer at a suitable temperature. In one aspect, the total lipid concentration of the solution is about 49.4 mg/mL. In certain preferred aspects, the RNA is included in an aqueous solution (e.g., buffer) and is diluted to a final concentration. Preferably, the final concentration is about 0.55 mg/mL in citrate buffer, with a pH of about 3.5.

The RNA is preferably a double-stranded RNA (dsRNA) or a mRNA. The size of the dsRNA is between 10 base pairs to several hundred bases, preferably less than 30 base pairs, most preferably less than 25 base pairs. The size of the mRNA is between 10 and several thousand bases in a single strand.

Lipid-Encapsulated RNA Nanoparticle Formation

After the organic solution and the aqueous solutions are prepared, they are mixed together using the apparatus described in detail below. Briefly, the apparatus consists of a first tube for transporting the aqueous RNA solution and a second tube for transporting the organic lipid solution, in which the second tube intersects the first tube perpendicularly within the mixing module. The two solutions are pumped through the respective tubes by separate HPLC pumps and mix in the region of the first tube perpendicularly within the mixing module. Preferably, the aqueous RNA solution is pumped at a rate 2.0-, 2.5-, 3.0-, 3.25-, or 3.5-fold, preferably 3.0-fold, greater than the organic lipid solution. Upon mixing the two solutions in the mixing area, lipid-encapsulated RNA nanoparticles are formed.

The pump speeds and the size of the first tube in the region of the mixing module provides for a mixing process that involves turbulent flow. The processes described herein for mixing of the lipid solution and the aqueous solution provides for encapsulation of RNA in the lipid nanoparticles formed coincident with their formation with an encapsulation efficiency of greater than 95%.

Lipid nanoparticles are typically formed at room temperature, but lipid nanoparticles may be formed at elevated temperatures according to the present invention. There are no general requirements for buffer composition. In fact, the processes and apparatus of the present invention can formulate a lipid vesicle by mixing lipid in ethanol with RNA in an aqueous solution.

In one embodiment, lipid nanoparticles form when lipids dissolved in an organic solvent, e.g., ethanol, are diluted in a stepwise manner by mixing with a buffered aqueous solution, first by mixing the aqueous and lipid streams together in the mixing module to a final concentration of organic solvent preferably between 25-40%. The resultant lipid, solvent and solute concentrations can be kept constant throughout the vesicle formation process. Following the initial formation, the initial lipid-RNA mixture is further diluted by addition of buffer, preferably to about 6.0%, 6.25%, 7.0% 7.5%, 10%, 12.5%, or 15% organic solvent, most preferably 6.25% 6.25%, 7.0% 7.5%, 10%, or 12.5%.

The continuous process described herein is fully scalable. In one aspect, lipid-encapsulated RNA nanoparticles are formed having a mean diameter of less than about 80 nm, without mechanical-energy processes such as membrane extrusion, sonication or microfluidization.

Lipid-Encapsulated RNA Nanoparticles

The lipid-encapsulated RNA nanoparticles disclosed herein comprise a nanoparticle or a bilayer of lipid molecules. In addition to the cationic lipids and ionizable cationic lipids, the lipid-encapsulated RNA nanoparticle comprises a neutral lipid or a polymer.

In some embodiments, the RNA is fully encapsulated within the lipid portion of the lipid nanoparticle such that the RNA in the lipid-encapsulated RNA nanoparticles is resistant in aqueous solution to nuclease degradation. In other embodiments, the lipid-encapsulated RNA nanoparticles described herein are substantially non-toxic to mammals such as humans. The lipid-encapsulated RNA nanoparticles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid-encapsulated RNA nanoparticles described herein also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1.

In preferred embodiments, the lipid particles comprise an RNA, a cationic lipid (e.g., one or more cationic lipids or salts thereof described herein), a phospholipid, and a conjugated lipid that inhibits aggregation of the particles (e.g., one or more PEG-lipid conjugates). The lipid-encapsulated RNA nanoparticles can also include cholesterol. The lipid-encapsulated RNA nanoparticles may comprise at least 1, 2, 3, 4, 5, 6, 7, 8, 9, 10, or more different RNA that express one or more polypeptides.

In the lipid-encapsulated RNA nanoparticles the RNA may be fully encapsulated within the lipid portion of the particle, thereby protecting the RNA from nuclease degradation. In preferred embodiments, the lipid-encapsulated RNA nanoparticles comprise an RNA that is fully encapsulated within the lipid portion of the particle, thereby protecting the RNA from nuclease degradation. In certain instances, the RNA in the lipid particle is not substantially degraded after exposure of the particle to a nuclease at 37° C. for at least 20, 30, 45, or 60 minutes. In certain other instances, the RNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the RNA is complexed with the cationic lipid of the lipid-encapsulated RNA nanoparticles. One of the benefits of the formulations of the present invention is that the lipid-encapsulated RNA nanoparticles are substantially non-toxic to mammals such as humans.

"Fully encapsulated" means that the RNA in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present invention provides a nucleic acid-lipid particle composition comprising a plurality of nucleic acid-lipid particles.

The lipid particle comprises RNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the RNA encapsulated therein.

Depending on the intended use of the lipid-encapsulated RNA nanoparticles, the proportions of the components can be varied and the delivery efficiency of a particular formulation can be measured using assays know in the art.

Lipid-NA Nanoparticle pDNA Production Process

Lipid-NA nanoparticle pDNA formulations were prepared by mixing lipids in ethanol with pDNA dissolved in 20 mM citrate, pH 3.5, 10 mM NaCl). Constituent lipids in the formulation ATX:DSPC:cholesterol:PEG-DMG at molar percentages of 50:7:40:3. The ethanolic solution containing lipids was mixed with the buffer stream containing pDNA at a flow rate ratio of 1:3 (ethanol:buffer) using a microfluidic device (Precision Nanosystems Inc.). The flow rate of lipid stream was 3 mL/min while the flow rate of pDNA stream was 9 ml/min. The total combined flow rate was 12 mL/min. Ethanol concentration in the lipid/DNA mix is 25% (V/V). The mixed material is instantaneously diluted with 2 volumes of 50 mM phosphate, pH 6.0, to reduce ethanol concentration to 8.3%. Diluted formulations were dialyzed against 50 mM phosphate, pH 6.0, for 12-16 h using cellulose dialysis membranes (100 Kd MWCO) following which secondary dialysis was performed against 50 mM HEPES, 50 mM NaCl, 9% sucrose, pH 7.4, for 3-5 h. Dialyzed formulations were concentrated using followed by concentration using AMICON® ULTRA CENTRIFUGAL filters (MilliporeSigma). pDNA concentration in the formulation is then measured by RIBOGREEN™ assay following which the concentration was adjusted to 0.2 mg/mL by diluting with 50 mM HEPES, 50 mM NaCl, 9% sucrose, pH 7.3 containing glycerol such that the final concentration of glycerol in the formulation is 5%. The diluted formulation is then filtered through a 0.2 μm filter and aseptically filled into glass vials, stoppered, capped and placed at −70±5° C.

The formulation is characterized for its lipid content by HPLC, percentage encapsulation and pDNA concentration by RIBOGREEN™ assay, particle size by dynamic light scattering on a Malvern ZETASIZER NANO ZS, PH, OSMOLALITY.

Figure 4:
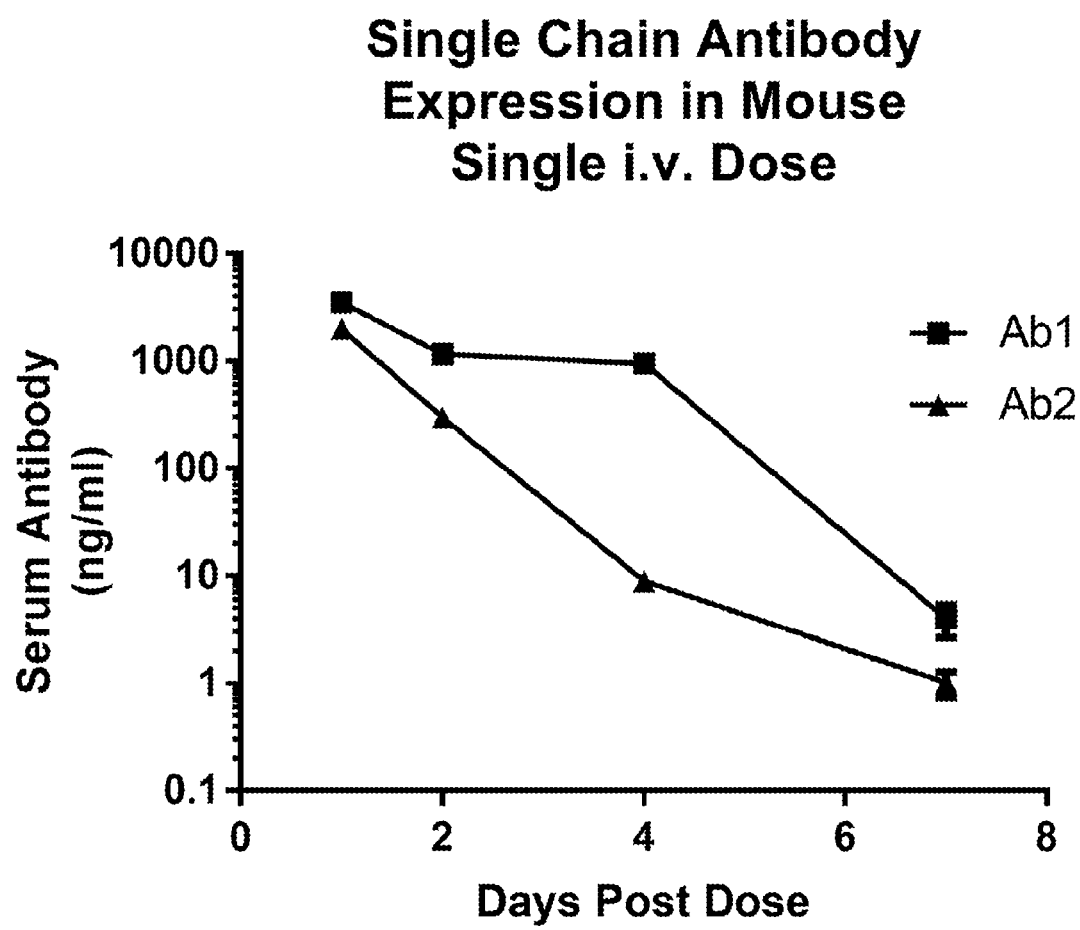
FIG. 4 shows lipid-NA nanoparticles effectively deliver mRNA encoding a single chain antibody and that the mRNA is expressed in a mouse model. Two formulations differing in mRNA (Ab 1 and Ab 2), encapsulated in lipid-NA nanoparticles was administered in a single intravenous administration to mice of mRNA at >1 μg/ml. Results show serum antibody levels in ng/ml (i.e., protective levels) measured at 1, 2, 4, and 7 days after dosing.

In Vivo Properties of Lipid-NA Nanoparticles:

Two formulations of lipid-NA nanoparticles prepared with a mRNA encoding two different antibodies were administered by a single intravenous administration and circulating antibody was measured at various times after injection. Results showed achieved serum antibody levels of >lug/ml (protective level) (FIG. 4).

TABLE

| Lipid composition | Lipid mol % | Nucleic Acid | Diameter (nm) | PDI | % Encap | Nucleic Acid Conc. (μg/mL) | % Yield from Theor | Nucleic Acid:Lipid Ratio (wt/wt) | pH |
|---|---|---|---|---|---|---|---|---|---|
| ATX_00012:DSPC:CHOL:DMG-PEG(2k) | 50:7:40:3 | mRNA | 95.7 | 0.147 | 97.7 | 239.4 | 75.2% | 0.028 | 7.3 |
| ATX_00012:DSPC:CHOL:DMG-PEG(2k) | 50:7:40:3 | Plasmid DNA | 96.9 | 0.106 | 96.5 | 254.8 | 79.6% | 0.028 | 7.2 |

Figure 5:
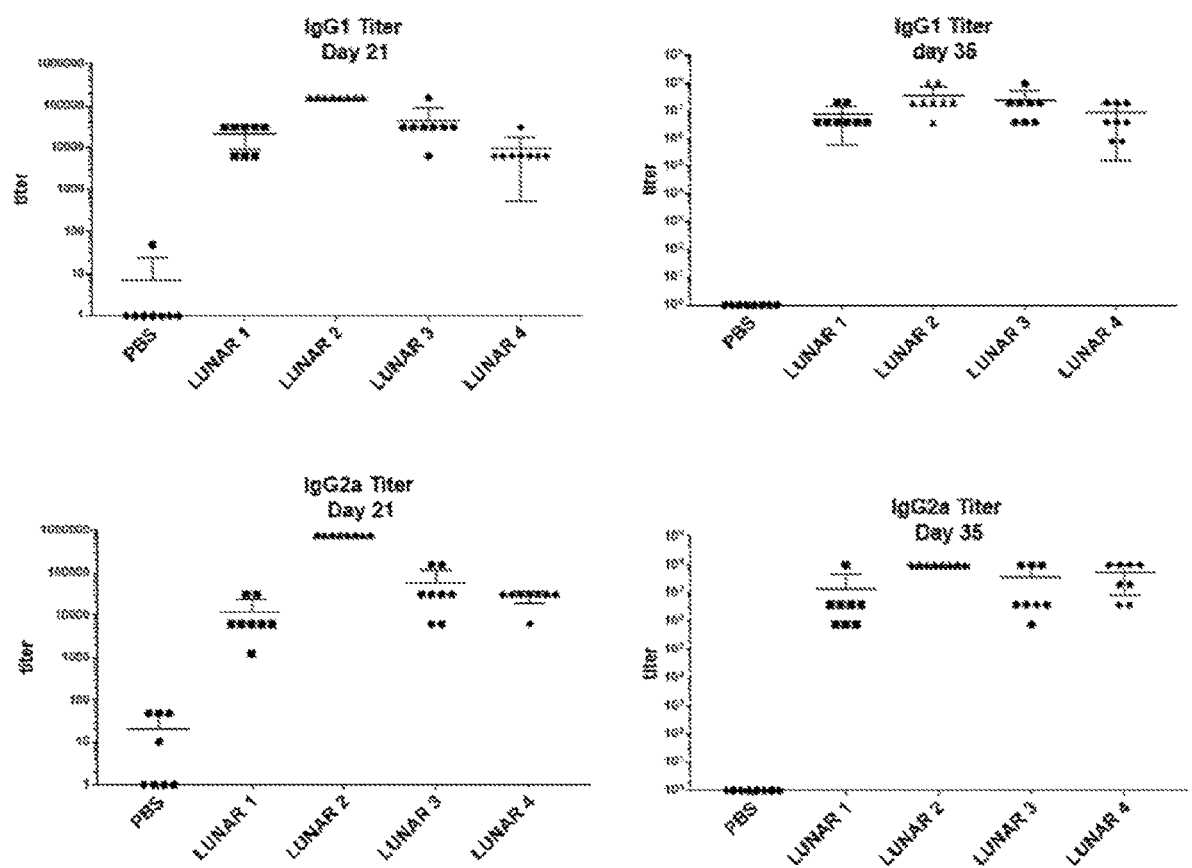
FIG. 5 shows lipid-NA nanoparticles encapsulating full-length mRNA encoding HA of influenza A/PuertoRico/8/1934 (PR8HA) H1N1 (PR8HA-mRNA) (Petsch, 2012, Nature Biotechnology 30:1210-16; doi: 10.1038/nbt.2436; incorporated by reference in its entirety) induced high neutralizing antibody titers in an animal model. The IgG1 and IgG2a titers are shown after 21 days following a 0.5 mg/kg intramuscular injection (left upper and lower panels, respectively) and at 35 days after a boost at day 20 (right upper and lower panels) for four different lipid-NA nanoparticle formulations (LUNAR™ 1, LUNAR™ 2, LUNAR™ 3, and LUNAR™ 4) compared to a PBS control. Each point represents the value obtained for a single animal.
Figure 6:
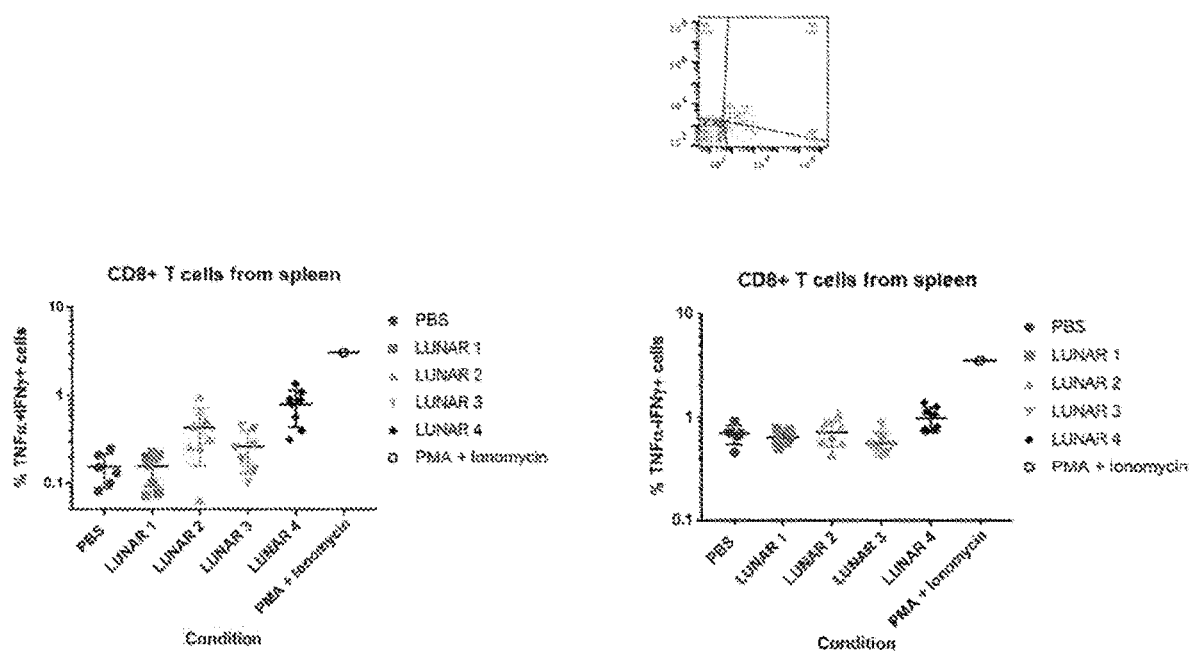
FIG. 6 shows lipid-NA nanoparticles encapsulating PR8HA-mRNA induces a CD8+ T cell response in an animal model. Flow cytometric gating provided an analysis of CD8+ T cells isolated from spleen. Four different lipid-NA nanoparticle formulations (LUNAR™ 1, LUNAR™ 2, LUNAR™ 3, and LUNAR™ 4) were administered by IM injection. Spleen T cells were treated with antigen and antigen-reactive cells were analyzed for production of cytokines tumor necrosis factor-alpha (TNFα) and interferon-gamma (IFNγ) compared to T cells treated with PBS (negative control) or PMA and ionomycin (positive control). The percentage of TNFα$^+$/IFNγ$^+$ (left panel) and TNFα$^-$/IFNγ$^+$ cells (right panel) are shown. Each point represents the value obtained for a single animal.
Figure 7:
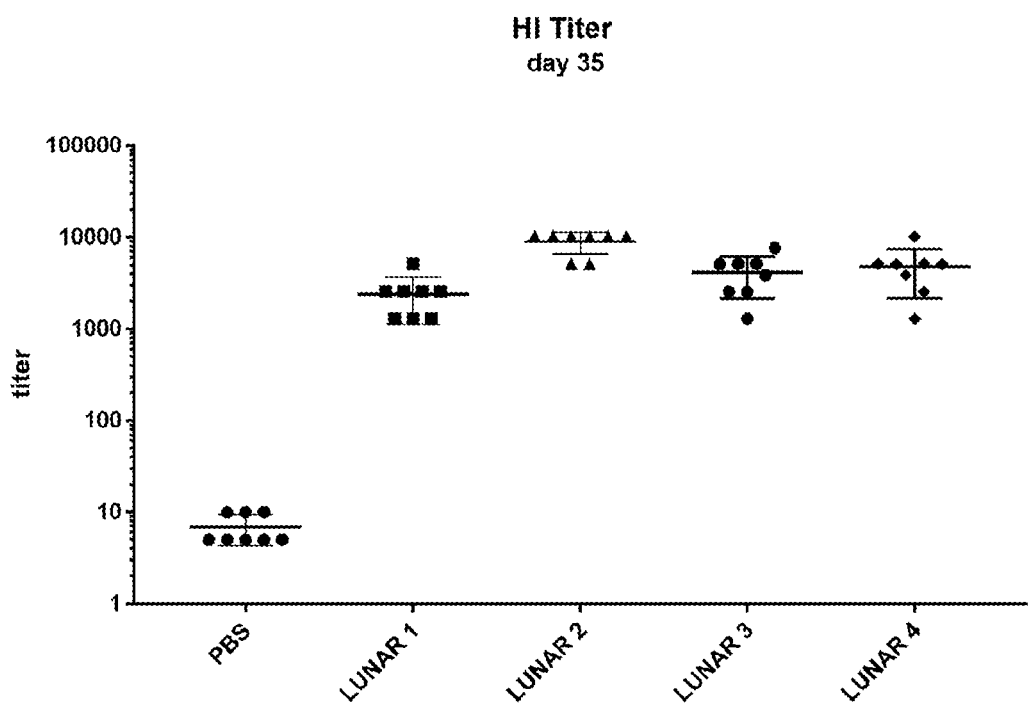
FIG. 7 shows lipid-NA nanoparticles encapsulating PR8HA-mRNA induces high titers in an hemagglutination inhibition assay. The titer measured by hemagglutinin inhibition (HI) is measured in animals treated by four different formulations of lipid-NA nanoparticles (LUNAR™ 1, LUNAR™ 2, LUNAR™ 3, and LUNAR™ 4) compared to animals administered PBS, 35 days after injection and a boost at 20 days. Each point represents the value obtained for a single animal.
Figure 8A:
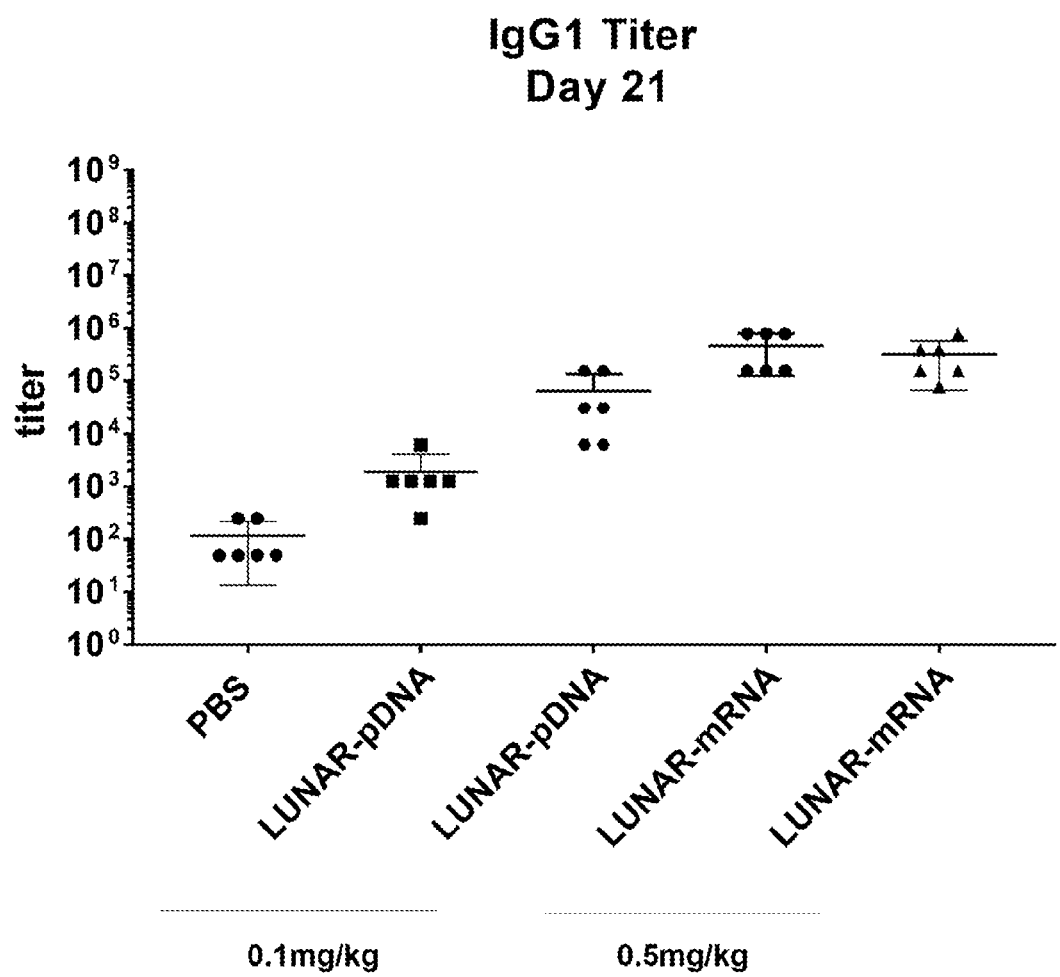
FIG. 8A and FIG. 8B show antigen-specific IgG1 response for mice vaccinated with lipid-NA nanoparticles encapsulating pDNA or mRNA. Mice were injected with 0.1 mg/kg or 0.5 mg/kg by intramuscular injection with lipid-NA nanoparticles encapsulating plasmid DNA (LUNAR™-pDNA) or mRNA (LUNAR™-mRNA), six animals per group. IgG1 serum titers are shown for animals at day 21 (FIG. 8A) and at day 35 after a boost at 21 days (FIG. 8B) compared to animals administered PBS. Each point represents the value obtained for a single animal.
Figure 8B:
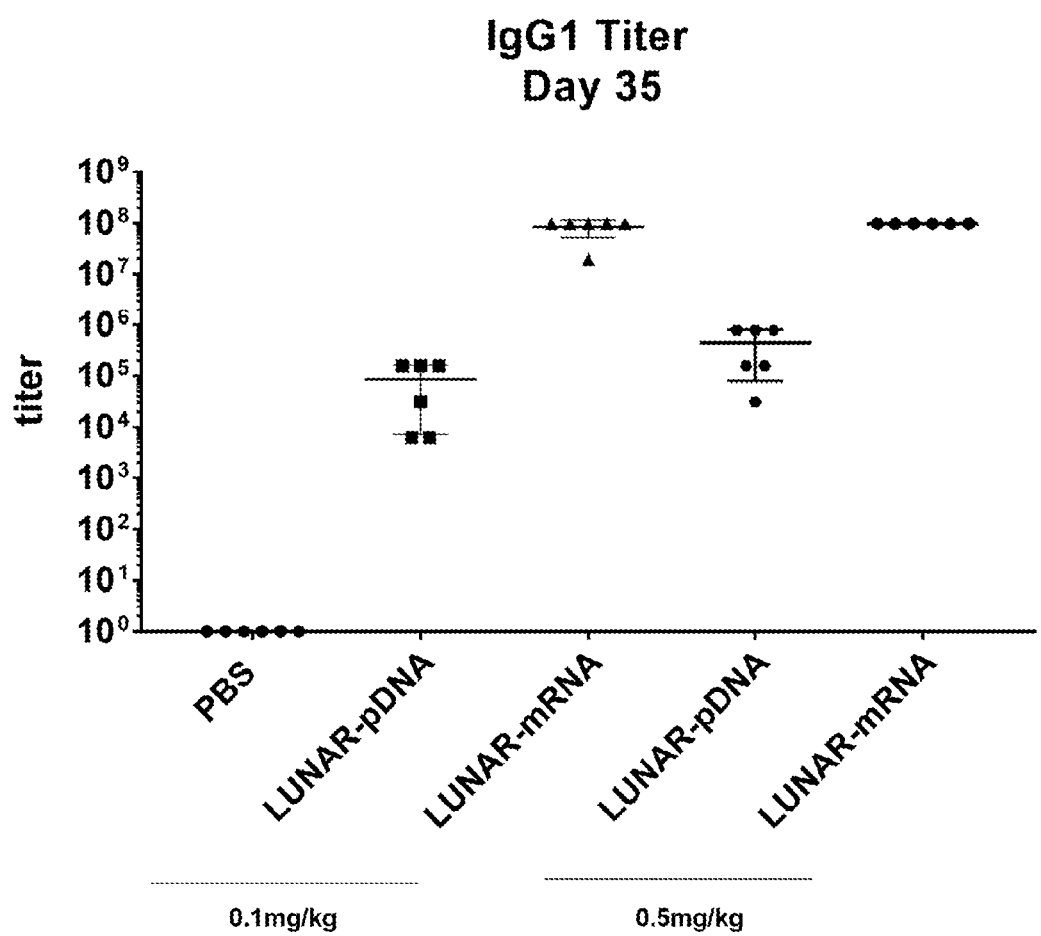
Figure 9A:
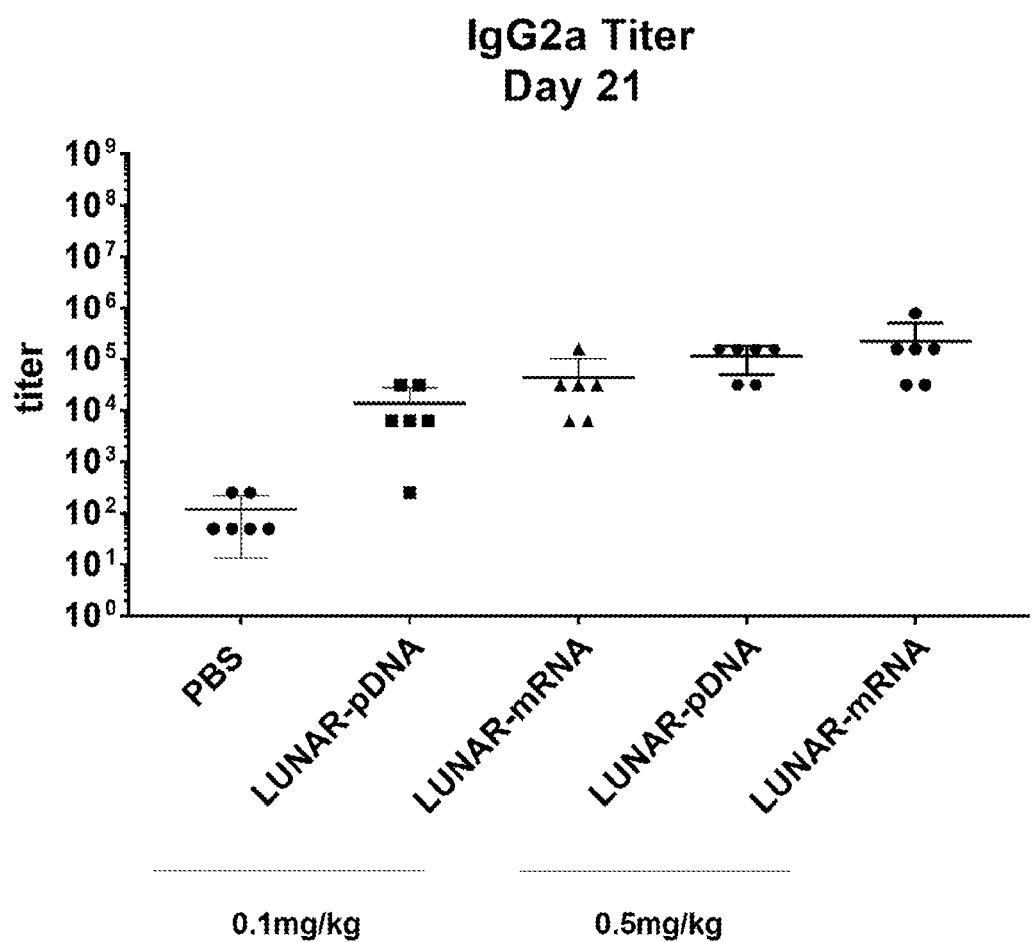
FIG. 9A and FIG. 9B show the antigen-specific IgG2 response for the mice vaccinated with lipid-NA nanoparticles encapsulating pDNA or mRNA as described in FIG. 8A and FIG. 8B. IgG2a titers are shown at day 21 (FIG. 9A) and at day 35 (FIG. 9B). Each point represents the value obtained for a single animal.
Figure 9B:
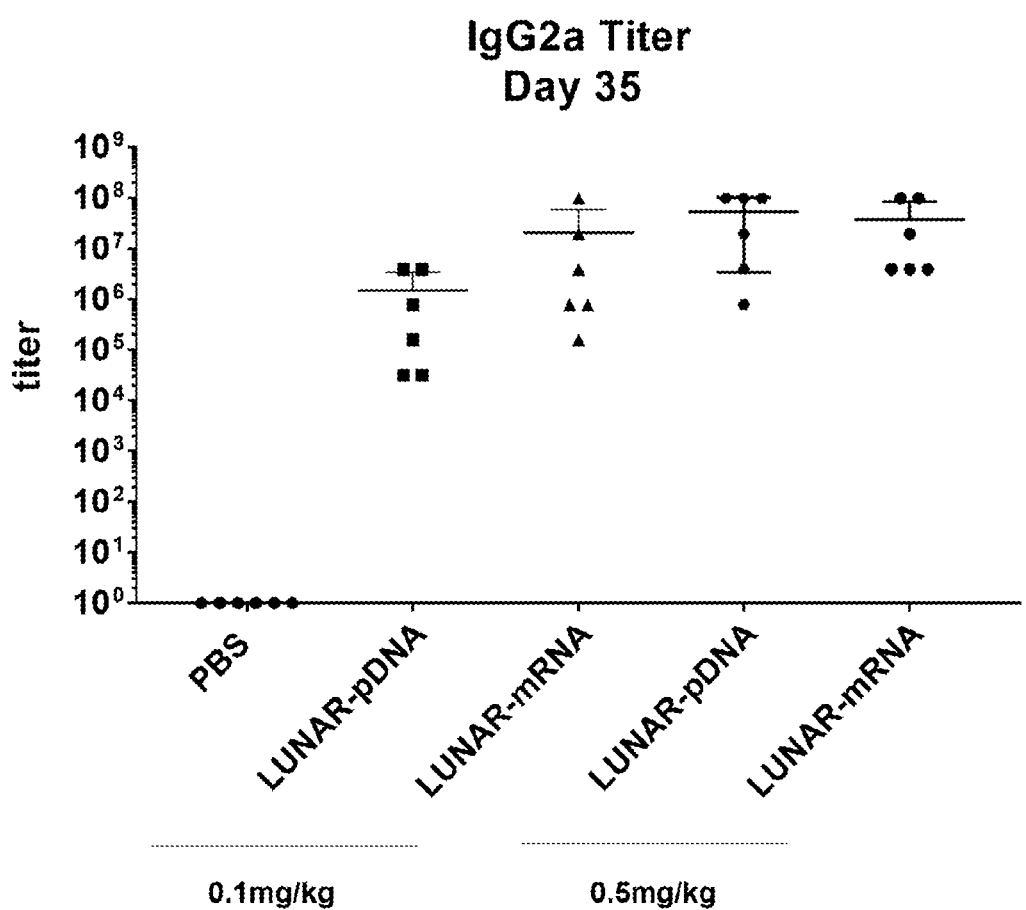

Wildtype Balb/c mice were treated with four different lipid-NA nanoparticle formulations prepared with a mRNA encoding for PR8HA (see TABLE above). Mice were dosed via intramuscular delivery at 0.5 mg/kg on Day 0 and Day 21. Serum was collected at Day 21 and Day 35 for evaluation of IgG antibody titers (FIG. 5) and hemagglutination inhibition assay (FIG. 7). On Day 35, mice were sacrificed and spleen were collected for evaluation of antigen-specific cytokine production from CD8+ T cells (FIG. 6).

The results showed antigen-specific immunity was induced by the lipid-PR8HA mRNA nanoparticles. On Day 21, antigen-specific IgG1 titers as high as $10^5$ and antigen-specific IgG2a titers as high as $10^6$ were achieved. At Day 35, IgG1 and IgG2a titers were as high as $10^8$. For LUNAR™ 1, LUNAR™ 2, and LUNAR™ 3, seven of the eight mice treated had an increase in the percentage of CD8+ T cells expressing TNFα and IFNγ. For and LUNAR™ 4, 8 of 8 mice had an increase in % CD8+ T cells expressing TNFα and IFNγ. In the hemagglutination inhibition assay, titers as high as $10^4$ were achieved.

Figure 10A:
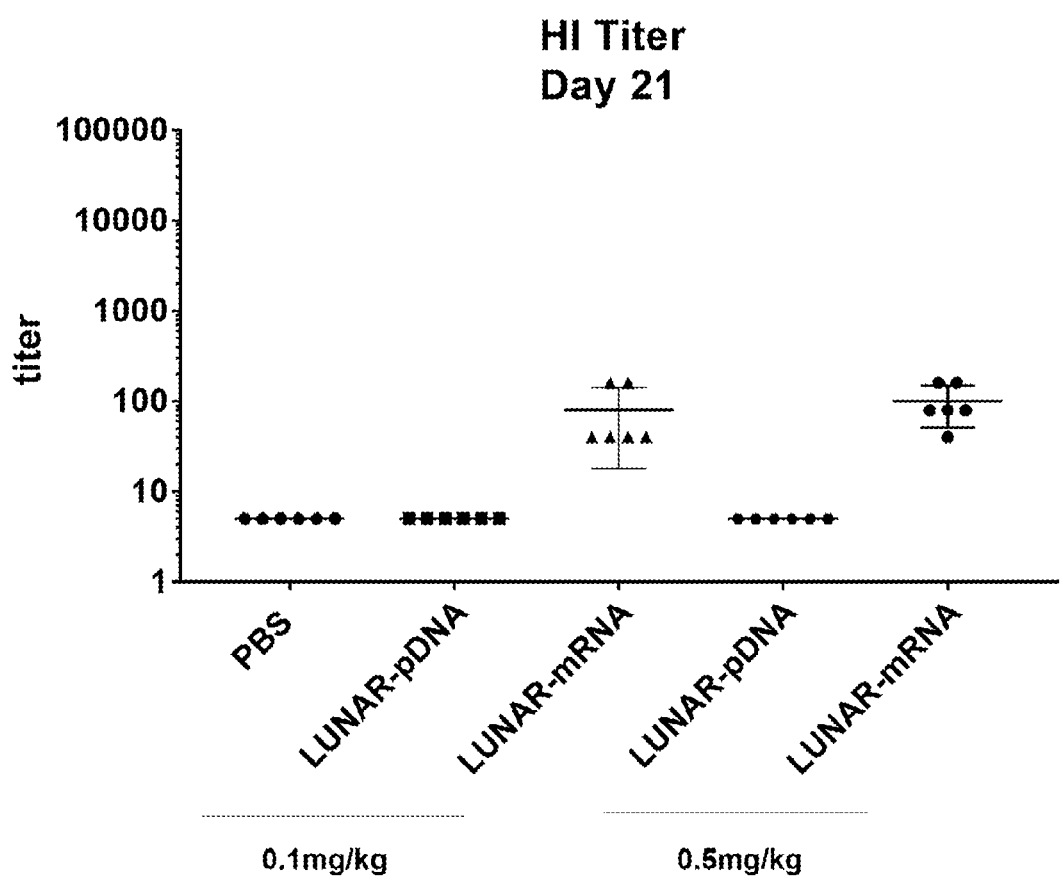
FIG. 10A and FIG. 10B show the results of hemagglutinin inhibition assay for the mice vaccinated with lipid-NA nanoparticles encapsulating pDNA or mRNA as described in FIG. 8A and FIG. 8B. HI titers are shown at day 21 (FIG. 10A) and at day 35 (FIG. 10B). Each point represents the value obtained for a single animal.
Figure 10B:
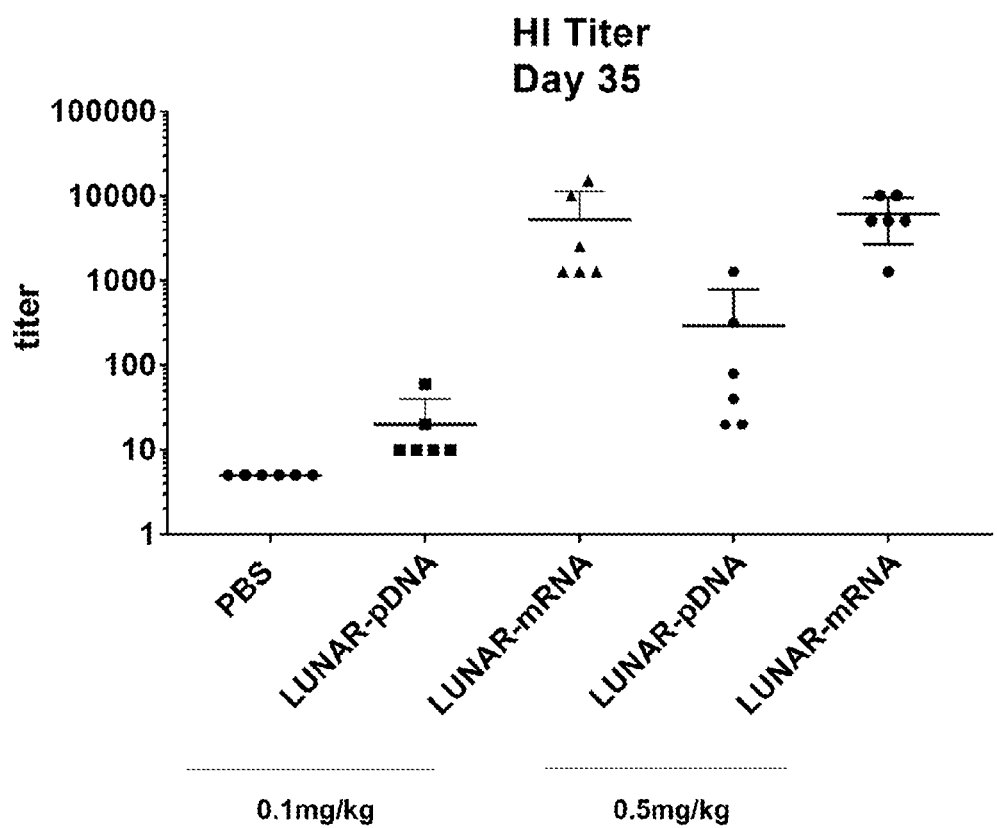
Figure 11A:
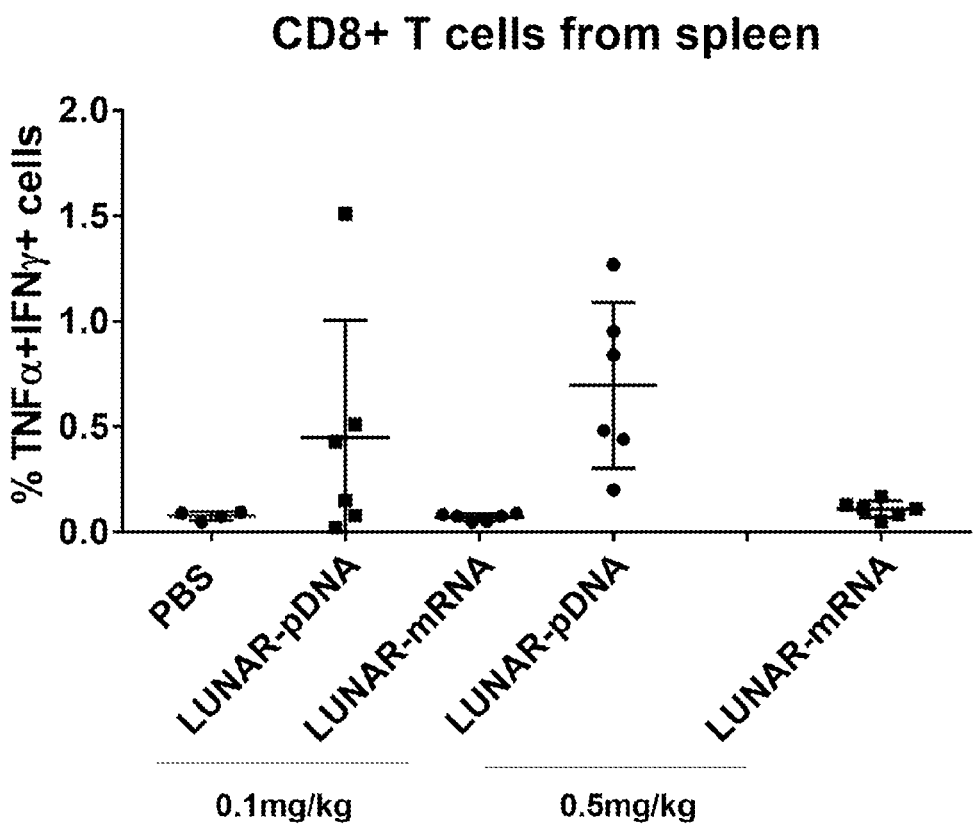
FIG. 11A and FIG. 11B show T-cell-mediated cytokine production of CD9+ T cells from spleen for the mice vaccinated with lipid-NA nanoparticles encapsulating pDNA or mRNA as described in FIG. 8A and FIG. 8B. Percentage of antigen-reactive, TNFα$^+$/IFNγ$^+$ cells are shown at day 35 for CD8+ T cells (FIG. 11A) and CD4+ T cells (FIG. 11B). Each point represents the value obtained for a single animal.
Figure 11B:
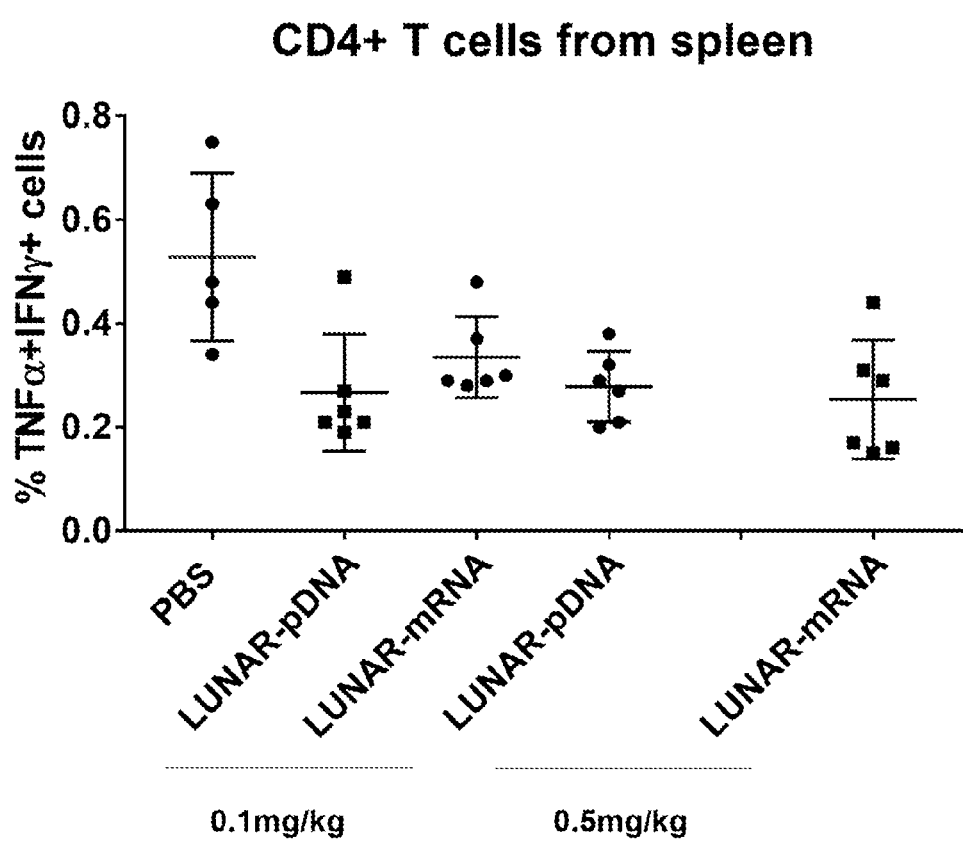

Wildtype Balb/c mice were treated with lipid-NA nanoparticle formulations prepared with a mRNA or plasmid DNA (pDNA) encoding PR8HA. Mice were dosed via intramuscular delivery at 0.1 or 0.5 mg/kg on Day 0 and Day 21. Serum was collected at Day 21 and Day 35 for evaluation of IgG antibody titers (FIGS. 8A, 8B, 9A, and 9B) and hemagglutination inhibition assay (FIG. 10A and FIG. 10B). On Day 35, mice were sacrificed and spleen were collected for evaluation of antigen-specific cytokine production from CD8+ T cells (FIG. 11A and FIG. 11B).

The results showed that on Day 21, antigen-specific IgG1 titers as high as $10^6$ were achieved and on Day 25, antigen-specific IgG1 titers as high as $10^8$ were observed. On Day 21, antigen-specific IgG2a titers as high as $10^6$ were achieved and on Day 25, antigen-specific IgG2a titers as high as $10^8$ were observed. In a hemagglutination inhibition assay, titers as high as $10^4$ were achieved. An increase in percentage of CD8+ T cells expressing antigen-specific TNFα and IFNγ was observed in LUNAR formulations prepared with plasmid DNA.

What is claimed:

1. A method of inducing an immune response in a subject comprising administering to the subject a pharmaceutical composition, the pharmaceutical composition comprising
   a lipid-NA nanoparticle comprising lipids and a nucleic acid (NA), the lipid-NA particle encapsulating the nucleic acid;
      wherein the lipids comprise a phospholipid, a cholesterol, a PEG-lipid, and a lipid of formula I

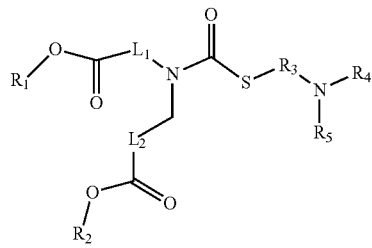

wherein
   $R_1$ and $R_2$ are the same or different, each a linear or branched alkyl or alkenyl consisting of 3 to 31 carbons, $R_3$ is a linear or branched alkylene consisting of 1 to 6 carbons, $R_4$ and $R_5$ are the same or different, each a hydrogen or a linear or branched alkyl consisting of 1 to 6 carbons;

$L_1$ is a linear alkylene of 1 to 20 carbons or a linear alkenylene of 2 to 20 carbons, $L_2$ is a linear alkylene of 1 to 20 carbons, a linear alkenylene of 2 to 20 carbons, or $L_2$ is a bond; and wherein the nucleic acid encodes an immunogenic peptide and the nucleic acid has a nucleotide (nt) length of 200 to 25,000 nt.

2. The method of claim 1, wherein the phospholipid is selected from 1,2-distearoyl-sn-glycero-3-phosphocholine (DSPC), phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine.

3. The method of claim 1, wherein the PEG-lipid is a PEG-diacylglycerol (PEG-DAG), a PEG-dialkyloxyalkyl (PEG-DAA), or a PEG-1,2-dimyristoyl-rac-glycero-3-methoxypolyethylene glycol (PEG-DMG).

4. The method of claim 1, wherein $R_3$ consists of ethylene or propylene and $R_4$ and $R_5$ separately are methyl or ethyl.

5. The method of claim 1, wherein $L_1$ and $L_2$ are each an alkylene consisting of 1, 2, 3, 4, 5, 6, 7, 8, 9, or 10 carbons.

6. The method of claim 1, wherein $R_1$ or $R_2$, or both is an alkenyl.

7. The method of claim 1 wherein $R_1$ is a branched alkyl and $R_2$ is an alkenyl consisting of 9 carbons.

8. The method of claim 1, wherein the lipid of formula I is selected from the group consisting of:

95 96
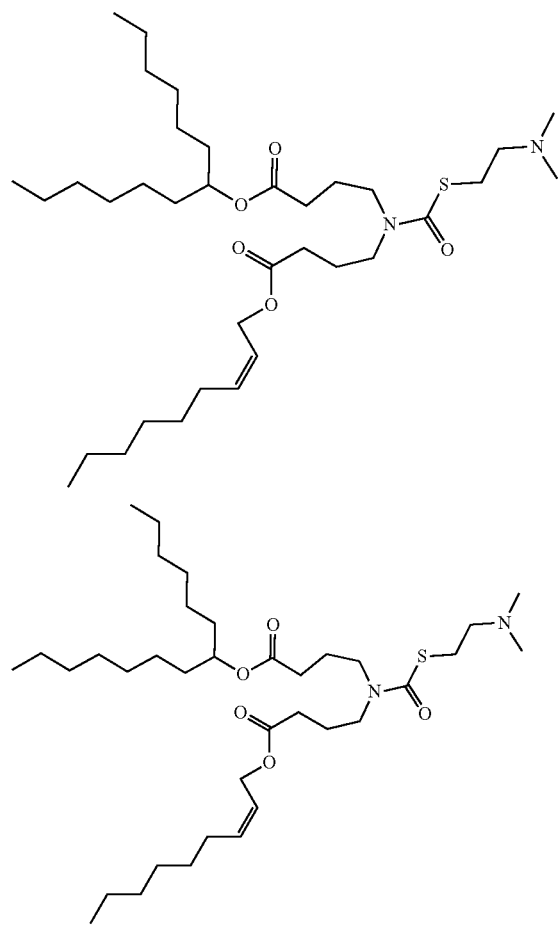
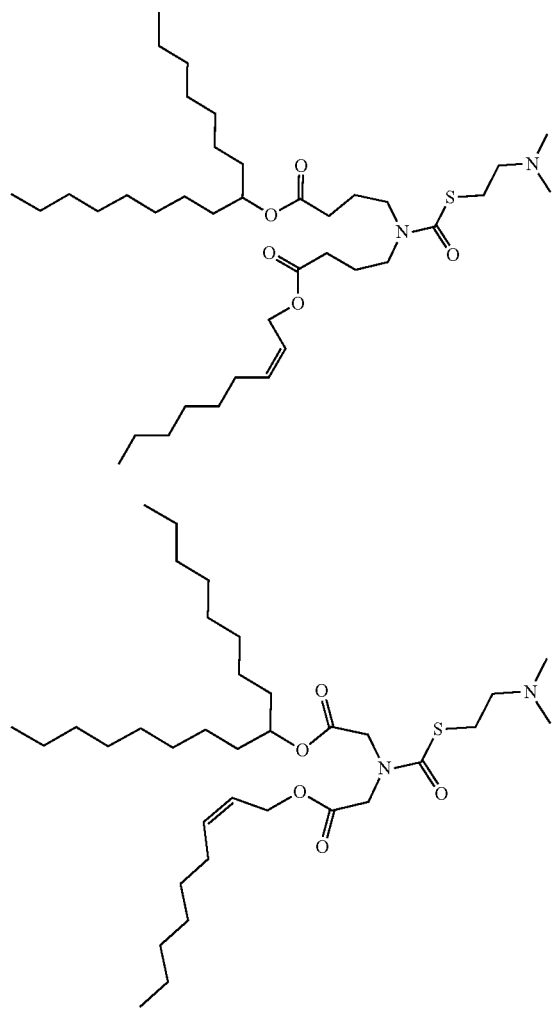
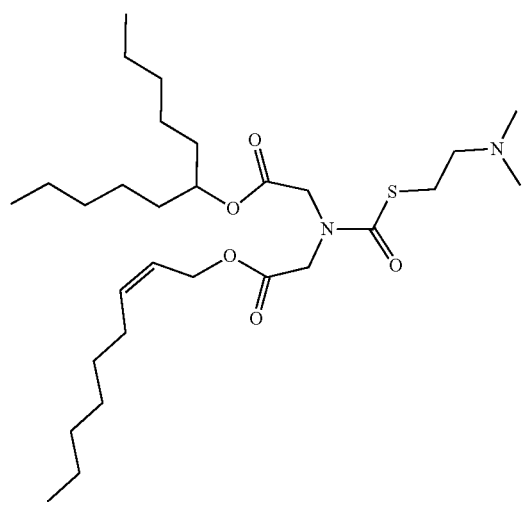
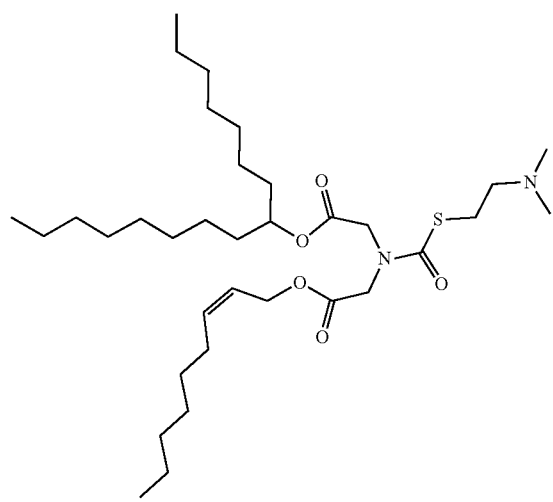

97 98
-continued
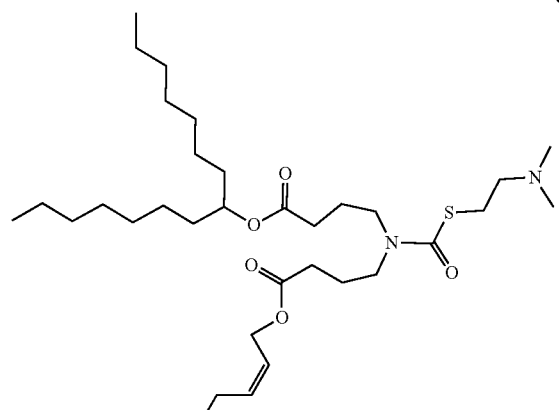
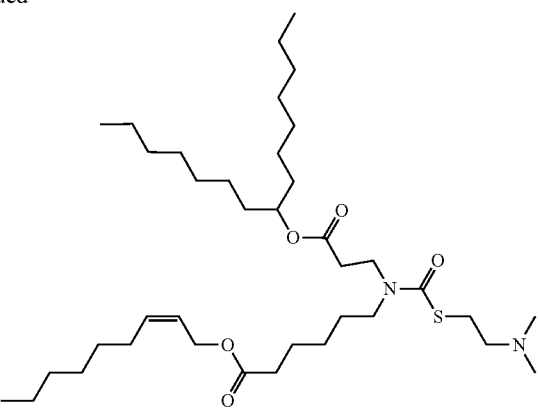
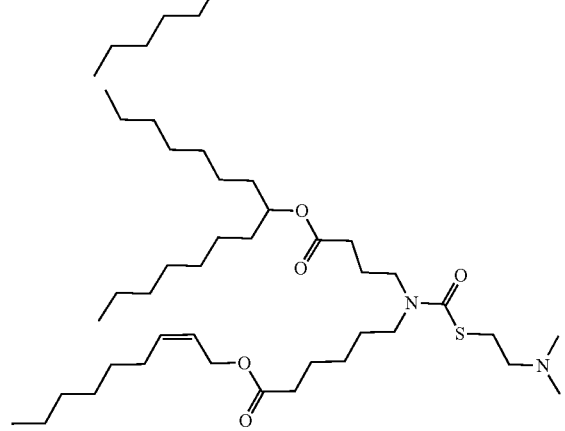
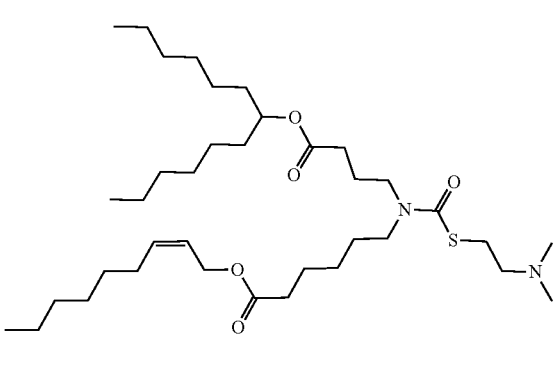
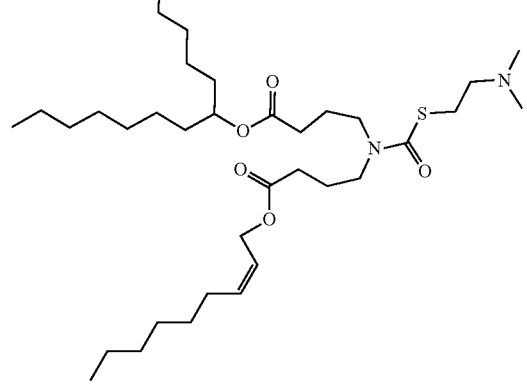
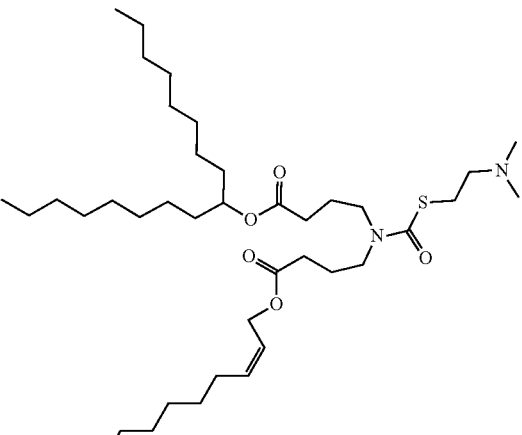
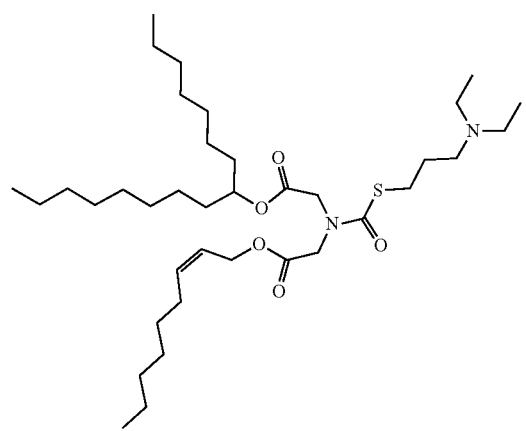 [SMILES: CCCCCC/C=C\COC(=O)CN(CC(=O)OC(CCCCCCC)CCCCCCCC)C(=O)SCCCN(CC)CC]

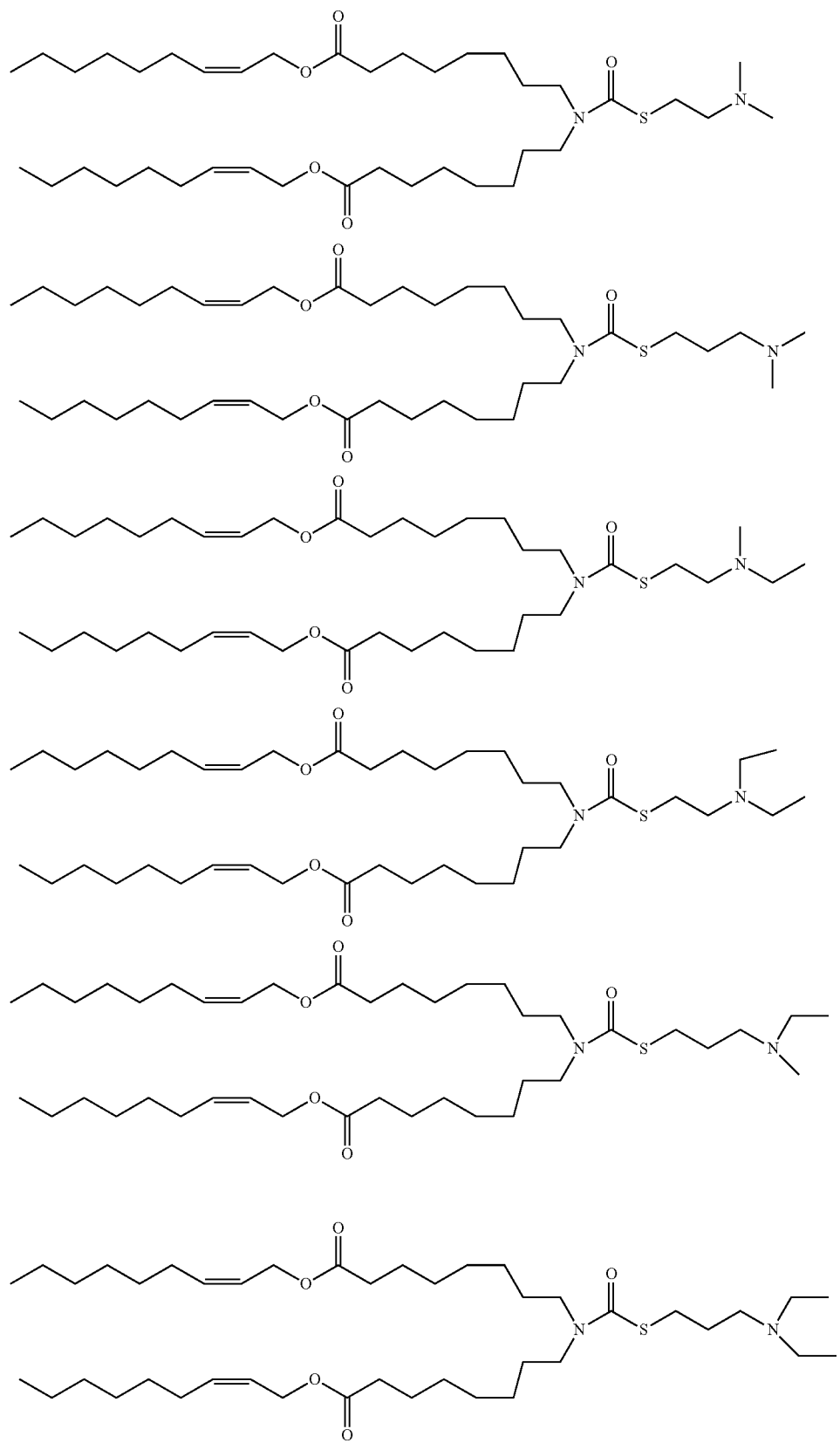

-continued

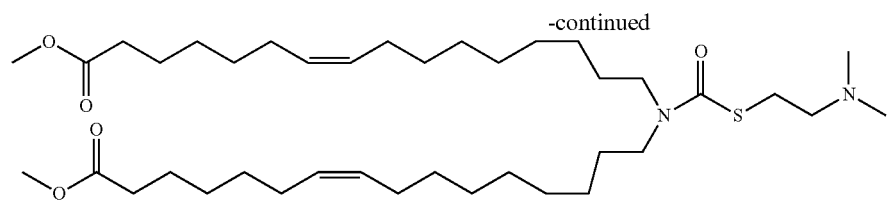

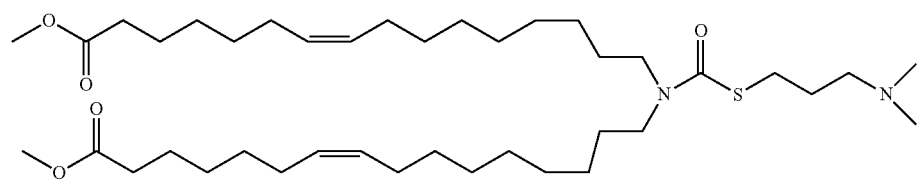

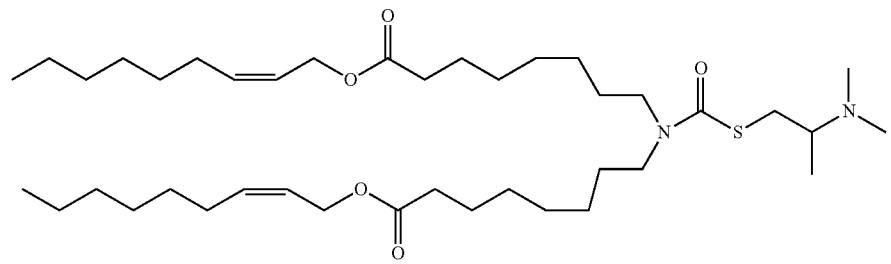

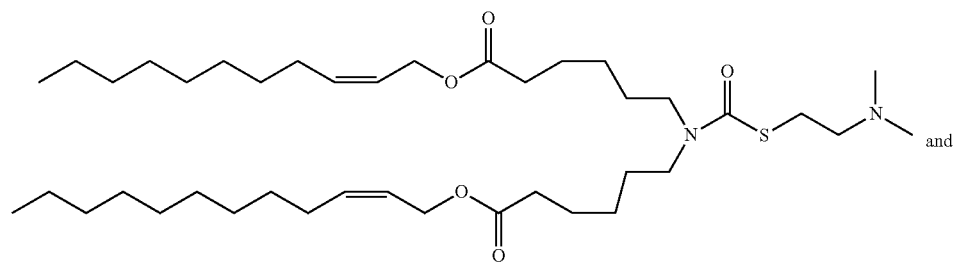

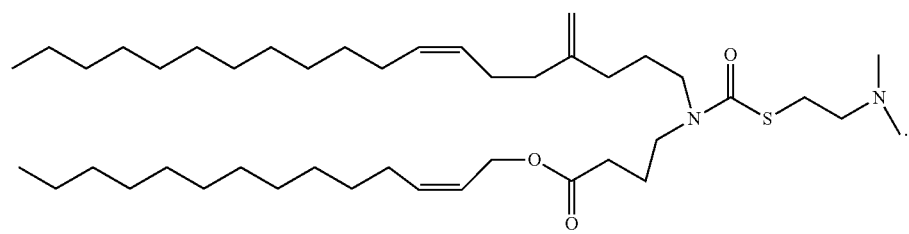

9. The method of claim 1, wherein the lipid-NA nanoparticle has a size less than 100 nm.

10. The method of claim 1, wherein the nucleic acid is an mRNA.

11. The method of claim 1, wherein the nucleic acid is an DNA.

12. The method of claim 1, wherein the immunogenic peptide is a viral protein.

13. The method of claim 12, wherein the viral protein is an antigen.

14. The method of claim 1, wherein administration is parenteral, by subcutaneous injection, by intradermal injection, or by intramuscular injection.

15. The method of claim 1, wherein the pharmaceutical composition is administered at least twice.

16. The method of claim 1, wherein the nucleic acid is self-replicating RNA.

17. The method of claim 1, wherein the lipid of Formula I is
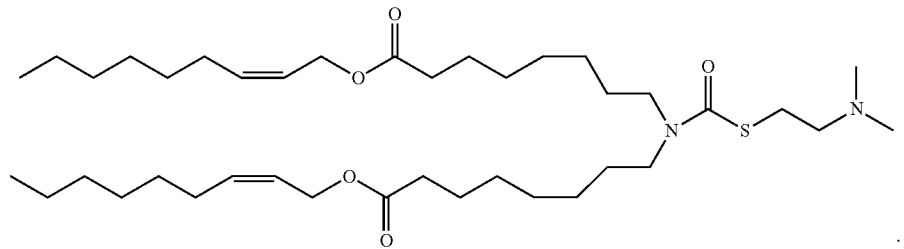 [SMILES: CCCCCC/C=C\COC(=O)CCCCCCCN(CCCCCCCC(=O)OC/C=C\CCCCCC)C(=O)SCCN(C)C]

UNITED STATES PATENT AND TRADEMARK OFFICE
CERTIFICATE OF CORRECTION

PATENT NO. : 12,083,224 B2
APPLICATION NO. : 17/042848
DATED : September 10, 2024
INVENTOR(S) : Chivukula et al.

It is certified that error appears in the above-identified patent and that said Letters Patent is hereby corrected as shown below:

On the Title Page

Item (72), under "Inventors", in Column 1, Line 6, delete "San Deigo," and insert -- San Diego, --, therefor.

In the Specification

In Column 1, Lines 55-56, delete "wherein the nucleic acid encodes an antibody or an immunogenic peptide." and insert the same on Line 56 as a new sub-point.

In Column 10, Line 54, delete "DESCRIPTION OF THE DRAWINGS" and insert -- BRIEF DESCRIPTION OF THE DRAWINGS --, therefor.

In Column 11, Line 17, delete "doi: 10.1038/nbt.2436;" and insert -- doi:10.1038/nbt.2436; --, therefor.

In Column 12, Line 37, delete "ail" and insert -- all --, therefor.

In Column 12, Line 44, delete "is meant" and insert -- it is meant --, therefor.

In Column 14, Line 32, delete "ms216A" and insert -- ms2i6A --, therefor.

In Column 14, Line 34, delete "ms2106A" and insert -- ms2io6A --, therefor.

In Column 14, Lines 39-40, delete "hn6A(N6-hydroxynorvalylcarbamoyl adenosine);" and insert -- hn6A (N6-hydroxynorvalylcarbamoyl adenosine); --, therefor.

In Column 14, Line 56, delete "(galtactosyl-queuosine);" and insert -- (galactosyl-queuosine); --, therefor.

Signed and Sealed this
Twenty-second Day of April, 2025

Coke Morgan Stewart
*Acting Director of the United States Patent and Trademark Office*

In Column 14, Lines 64-65, delete "(5-(carboxyhydroxymethyl)uridine));" and insert -- (5-(carboxyhydroxymethyl)uridine); --, therefor.

In Columns 14 & 15, Lines 67 & 1, delete "(S-methoxycarbonylmethyl-2-O-methyluridine);" and insert -- (5-methoxycarbonylmethyl-2-O-methyluridine); --, therefor.

In Column 15, Line 24, delete "(S-taurinomethyl-2-thiouridine));" and insert -- (5-taurinomethyl-2-thiouridine); --, therefor.

In Column 16, Lines 48-49, delete "N-(2,3-dioleoyloxy)propyl)-N,N,N-trimethylammonium" and insert -- N-[(2,3-dioleoyloxy)propyl]-N,N,N-trimethylammonium --, therefor.

In Column 16, Lines 51-52, delete "N-(2,3-dioleoyloxy)propyl)-N,N,N-trimethylammonium" and insert -- N-[(2,3-dioleoyloxy)propyl]-N,N,N-trimethylammonium --, therefor.

In Column 81, Line 10, delete "know" and insert -- known --, therefor.

In Column 82, Line 38, delete "polyethyloxylated" and insert -- polyethoxylated --, therefor.

In Column 83, Line 40, delete "+5" and insert -- $\pm 5$ --, therefor.

In Column 84, Line 65, delete "R' and $R_2$," and insert -- $R^1$ and $R^2$, --, therefor.

In Column 85, Line 4, delete "icosoyl" and insert -- eicosanoyl --, therefor.

In Column 86, Line 10, delete "fowipox," and insert -- fowlpox, --, therefor.

In Column 86, Line 45, delete "intended" and insert -- intended to be --, therefor.

In Column 86, Line 63, delete "olcate." and insert -- oleate. --, therefor.

In Column 87, Line 24, delete "phenlyiacetic," and insert -- phenylacetic, --, therefor.

In Column 87, Line 25, delete "HOOC—(CH2)$_n$—COOH" and insert -- HOOC—(CH$_2$)$_n$—COOH --, therefor.

In Column 88, Line 38, delete "50:7:40:3)." and insert -- 50:7:40:3. --, therefor.

In Column 92, Line 27, delete "know" and insert -- known --, therefor.

In Column 92, Line 30, delete "NaCl)." and insert -- NaCl. --, therefor.

In Column 92, Line 67, delete ">lug/ml" and insert -- >1 µg/ml --, therefor.

In Column 93, Line 23, delete "105" and insert -- $10^5$ --, therefor.

CERTIFICATE OF CORRECTION (continued)
U.S. Pat. No. 12,083,224 B2

In the Claims

In Column 93, Line 61, in Claim 1, delete "comprising" and insert -- comprising: --, therefor.

In Column 94, Line 34, in Claim 1, delete "carbons;" and insert -- carbons, --, therefor.

In Columns 101 & 102, Lines 50-55, in Claim 8, delete "

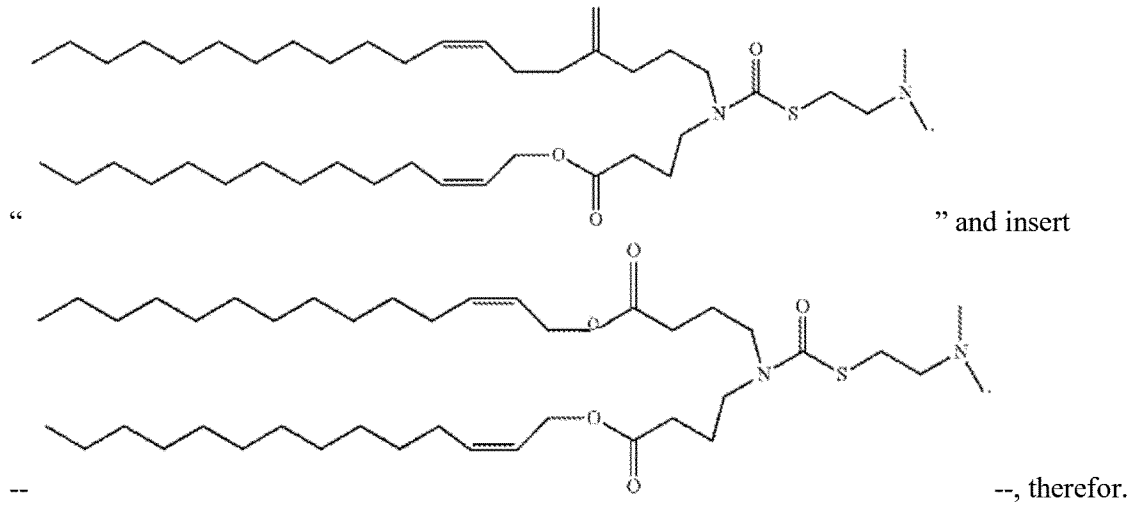

" and insert --

--, therefor.